United States Patent
Coffey

(10) Patent No.: US 7,803,385 B2
(45) Date of Patent: Sep. 28, 2010

(54) REOVIRUSES HAVING MODIFIED SEQUENCES

(75) Inventor: Matthew C. Coffey, Calgary (CA)

(73) Assignee: Oncolytics Biotech Inc., Calgary, Alberta (CA)

( * ) Notice: Subject to any disclaimer, the term of this patent is extended or adjusted under 35 U.S.C. 154(b) by 0 days.

(21) Appl. No.: 12/046,095

(22) Filed: Mar. 11, 2008

(65) Prior Publication Data

US 2008/0226602 A1    Sep. 18, 2008
US 2009/0035278 A2    Feb. 5, 2009

Related U.S. Application Data

(60) Provisional application No. 60/989,568, filed on Nov. 21, 2007, provisional application No. 60/894,425, filed on Mar. 12, 2007.

(51) Int. Cl.
*A61K 48/00* (2006.01)
*C12N 7/00* (2006.01)

(52) U.S. Cl. ............... 424/215.1; 424/186.1; 424/93.1; 435/235.1

(58) Field of Classification Search ............... None
See application file for complete search history.

(56) References Cited

U.S. PATENT DOCUMENTS

| | | | |
|---|---|---|---|
| 6,110,461 A | 8/2000 | Lee et al. | |
| 6,136,307 A | 10/2000 | Lee et al. | |
| 6,261,555 B1 | 7/2001 | Lee et al. | |
| 6,344,195 B1 | 2/2002 | Lee et al. | |
| 6,528,305 B2 | 3/2003 | Thompson et al. | |
| 6,565,831 B1 | 5/2003 | Coffey et al. | |
| 6,576,234 B2 | 6/2003 | Lee et al. | |
| 6,808,916 B2 | 10/2004 | Coffey et al. | |
| 6,811,775 B2 | 11/2004 | Lee et al. | |
| 7,014,847 B2 | 3/2006 | Coffey et al. | |
| 7,049,127 B2 * | 5/2006 | Thompson et al. | 435/235.1 |
| 7,052,832 B2 | 5/2006 | Coffey | |
| 7,163,678 B2 | 1/2007 | Norman et al. | |
| 7,186,542 B2 | 3/2007 | Coffey et al. | |
| 7,374,752 B2 * | 5/2008 | Lee et al. | 424/93.2 |
| 7,452,723 B2 * | 11/2008 | Coffey et al. | 424/131.1 |

2008/0014183 A1    1/2008  Okano et al.

FOREIGN PATENT DOCUMENTS

WO    WO 2007/099401    9/2007
WO    WO 2008/009115    1/2008

OTHER PUBLICATIONS

Nibert et al. J. Virol. 1996, vol. 70, No. 10, pp. 7295-7300.*
Wenske et al. J. Virol. 1985, vol. 56, No. 2, pp. 613-616.*
Wiener et al. Virol. 1989, vol. 169, pp. 194-203.*
Chappell et al. J. Virol. 1994, vol. 68, No. 2, pp. 750-756.*
Dermody et al., "The S2 Gene Nucleotide Sequences of Prototype Strains of the Three Reovirus Serotypes: Characterization of Reovirus Core Protein σ2," *J. Virol.*, 1991, 65(11):5721-5731.
McCutcheon et al., "Mammalian Reovirus M3 Gene Sequences and Conservation of Coiled-Coil Motifs near the Carboxyl Terminus of the μNS Protein," *Virology*, 1999, 264:16-24.
Richardson and Furuichi, "Nucleotide sequences of reovirus genome segment S3, encoding non-structural protein sigma NS," *Nucl. Acids Res.*, 1983, 11(18):6399-6408.
Wiener et al., "The Sequences of the S2 Genome Segments of Reovirus Serotype 3 and of the dsRNA-Negative Mutant ts447," *Virology*, 1989, 170:340-341.
GenBank Accession No. AF461684 dated Apr. 12, 2002.
GenBank Accession No. K02739 dated Aug. 3, 1993.
GenBank Accession No. M20161 dated Mar. 7, 1995.
GenBank Accession No. M24734 dated Jun. 16, 1994.
GenBank Accession No. NP_694684 dated May 22, 2008.
GenBank Accession No. AF129822 dated Jul. 5, 1999.
GenBank Accession No. J03488 dated Aug. 3, 1993.
GenBank Accession No. M10262 dated Aug. 3, 1993.
GenBank Accession No. X01627 dated Mar. 25, 2003.
Chappell et al., "Sequence Diversity within the Reovirus S2 Gene: Reovirus Genes Reassort in Nature, and Their Termini Are Predicted to Form a Panhandle Motif," *J. Virol.*, 1994, 68(2):750-756.
Rudd and Lemay, "Correlation between interferon sensitivity of reovirus isolates and ability to discriminate between normal and *Ras*-transformed cells," *J. Gen. Virol.*, 2005, 86:1489-1497.

* cited by examiner

*Primary Examiner*—Zachariah Lucas
*Assistant Examiner*—Bao Li
(74) *Attorney, Agent, or Firm*—McKeon Meunier Carlin & Curfman LLC

(57) ABSTRACT

The invention provides for modified reovirus nucleic acid sequences and modified reovirus polypeptide sequences as well as reoviruses containing such modified nucleic acid or polypeptide sequences. The invention also provides for pharmaceutical compositions that include reoviruses having a modified sequence as well as methods of making and using such reoviruses.

13 Claims, 12 Drawing Sheets

Figure 1

S1:
GCTATTGGTCGGATGGATCCTCGCCTACGTGAAGAAGTAGTACGGCTGATAATCGCATTAACGAGTGATAA
TGGAGCATCACTGTCAAAAGGGCTTGAATCAAGGGTCTCGGCGCTCGAGAAGACGTCTCAAATACACTCTG
ATACTATCCTCCGGATCACCCAGGGACTCGATGATGCAAACAAACGAATCATCGCTCTTGAGCAAAGTCGG
GATGACTTGGTTGCATCAGTCAGTGATGCTCAACTTGCAATCTCCAGATTGGAAAGCTCTATCGGAGCCCT
CCAAACAGTTGTCAATGGACTTGATTCGAGTGTTACCCAGTTGGGTGCTCGAGTGGGACAACTTGAGACAG
GACTTGCAGAGCTACGCGTTGATCACGACAATCTCGTTGCGAGAGTGGATACTGCAGAACGTAACATTGGA
TCATTGACCACTGAGCTATCAACTCTGACGTTACGAGTAACATCCATACAAGCGGATTTCGAATCTAGGAT
ATCCACGTTAGAGCGCACGGCGGTCACTAGCGCGGGAGCTCCCCTCTCAATCCGTAATAACCGTATGACCA
TGGGATTAAATGATGGACTCACGTTGTCAGGGAATAATCTCGCCATCCGATTGCCAGGAAATACGGGTCTG
AATATTCAAAATGGTGGACTTCAGTTTCGATTTAATACTGATCAATTCCAGATAGTTAATAATAACTTGAC
TCTCAAGACGACTGTGTTTGATTCTATCAACTCAAGGATAGGCGCAACTGAGCAAAGTTACGTGGCGTCGG
CAGTGACTCCCTTGAGATTAAACAGTAGCACGAAGGTGCTGGATATGCTAATAGACAGTTCAACACTTGAA
ATTAATTCTAGTGGACAGCTAACTGTTAGATCGACATCCCCGAATTTGAGGTATCCGATAGCTGATGTTAG
CGGCGGTATCGGAATGAGTCCAAATTATAGGTTTAGGCAGAGCATGTGGATAGGAATTGTCTCCTATTCTG
GTAGTGGGCTGAATTGGAGGGTACAGGTGAACTCCGACATTTTTATTGTAGATGATTACATACATATATGT
CTTCCAGCTTTTGACGGTTTCTCTATAGCTGACGGTGGAGATCTATCGTTGAACTTTGTTACCGGATTGTT
ACCACCGTTACTTACAGGAGACACTGAGCCCGCTTTTCATAATGACGTGGTCACATATGGAGCACAGACTG
TAGCTATAGGGTTGTCGTCGGGTGGTGCGCCTCAGTATATGAGTAAGAATCTGTGGGTGGAGCAGTGGCAG
GATGGAGTACTTCGGTTACGTGTTGAGGGGGGTGGCTCAATTACGCACTCAAACAGTAAGTGGCCTGCCAT
GACCGTTTCGTACCCGCGTAGTTTCACGTGAGGATCAGACCACCCCGCGGCACTGGGGCATTTCATC
(SEQ ID NO:1)

S2:
GCTATTCGCTGGTCAGTTATGGCTCGCGCTGCGTTCCTATTCAAGACTGTTGGGTTTGGTGGTCTGCAAAA
TGTGCCAATTAACGACGAACTATCTTCACATCTACTCCGAGCTGGTAATTCACCATGGCAGTTAACACAGT
TTTTAGACTGGATAAGCCTTGGGAGGGGTTTAGCTACATCGGCTCTCGTTCCGACGGCTGGGTCAAGATAC
TATCAAATGAGTTGCCTTCTAAGTGGCACTCTCCAGATTCCGTTCCGTCCTAACCACCGATGGGGAGACAT
TAGGTTCTTACGCTTAGTGTGGTCAGCTCCTACTCTCGATGGATTAGTCGTAGCTCCACCACAAGTTTTGG
CTCAGCCCGCTTTGCAAGCACAGGCAGATCGAGTGTACGACTGCGATGATTATCCATTTCTAGCGCGTGAT
CCAAGATTCAAACATCGGGTGTATCAGCAATTGAGTGCTGTAACTCTACTTAACTTGACAGGTTTTGGCCC
GATTTCCTACGTTCGAGTGGATGAAGATATGTGGAGTGGAGATGTGAACCAGCTTCTCATGAACTATTTCG
GGCACACGTTTGCAGAGATTGCATACACATTGTGTCAAGCCTCGGCTAATAGGCCTTGGGAATATGACGGT
ACATATGCTAGGATGACTCAGATTGTGTTATCCTTGTTCTGGCTATCGTATGTCGGTGTAATTCATCAGCA
GAATACGTATCGGACATTCTATTTTCAGTGTAATCGGCGAGGTGACGCCGCTGAGGTGTGGATTCTTTCTT
GTTCGTTGAACCATTCCGCACAAATTAGACCGGGTAATCGTAGCTTATTCGTTATGCCAACTAGCCCAGAT
TGGAACATGGACGTCAATTTGATCCTGAGTTCAACGTTGACGGGGTGTTTGTGTTCGGGTTCACAGCTGCC
ACTGATTGACAATAATTCAGTACCTGCAGTGTCGCGTAACATCCATGGCTGGACTGGTAGAGCTGGTAACC
AATTGCATGGGTTCCAGGTGAGACGAATGGTGACTGAATTTTGTGACAGGTTGAGACGCGATGGTGTCATG
ACCCAAGCTCAGCAGAATCAAGTTGAAGCGTTGGCAGATCAGACTCAACAGTTTAAGAGGGACAAGCTCGA
AACGTGGGCGAGAGAAGACGATCAATATAATCAGGCTCATCCCAACTCCACAATGTTCCGTACGAAACCAT
TTACGAATGCGCAATGGGGACGAGGTAATACGGGGCGACTAGTGCCGCGATTGCAGCCCTTATCTGATCG
TCTTGGAGTGAGGGGGTCCCCCCACACACCTCACGACTGACCACACATTCATC (SEQ ID NO:2)

S3:
GCTAAAGTCACGCCTGTCGTCGTCACTATGGCTTCCTCACTCAGAGCTGCGATCTCCAAGATCAAGAGGGA
TGACGTCGGTCAGCAAGTTTGTCCTAATTATGTCATGCTGCGGTCCTCTGTCACAACAAAGGTGGTACGAA
ATGTGGTTGAGTATCAAATTCGTACGGGCGGATTCTTTTCGTGCTTAGCTATGCTAAGGCCACTCCAGTAC
GCTAAGCGTGAGCGTTTGCTTGGTCAGAGGAATCTGGAACGTATATCGACTAGGGATATCCTTCAGACTCG
TGATTTACACTCACTATGTATGCCAACTCCTGATGCGCCAATGTCTAATCATCAAGCATCCACCATGAGAG
AGCTGATTTGCAGTTACTTCAAGGTCGATCATGCGGATGGGTTGAAATATATACCCATGGATGAGAGATAC

Figure 1-2

TCTCCGTCATCACTTGCCAGATTGTTTACCATGGGCATGGCTGGGCTGCACATTACCACTGAGCCATCTTA
TAAGCGTGTTCCGATTATGCACTTAGCTGCGGACTTGGACTGTATGACGCTGGCTCTACCTTACATGATTA
CGCTTGATGGTGATACTGTGGTTCCTGTCGCTCCAACACTGTCAGCGGAACAGCTTCTGGACGACGGACTC
AAAGGATTAGCATGCATGGATATCTCCTATGGATGTGAGGTGGACGCGAATAGCCGGCCGGCTGGTGATCA
GAGTATGGACTCTTCACGCTGCATCAACGAGTTGTATTGCGAGGAGACAGCAGAAGCCATCTGTGTGCTTA
AGACATGCCTTGTGTTAAATTGCATGCAGTTTAAACTTGAGATGGATGACCTAGCACATAACGCTGCTGAG
CTGGACAAGATACAGATGATGATACCCTTCAGTGAGCGTGTTTTTAGGATGGCCTCGTCCTTTGCGACTAT
TGATGCCCAGTGTTTTAGGTTTTGCGTGATGATGAAGGATAAAAATCTGAAAATAGATATGCGTGAAACGA
CGAGACTGTGGACTCGTTCAGCATCAGATGATTCTGTGGCCACGTCATCTTTAAGTATTTCCCTGGACCGG
GGTCGATGGGTGGCGGCTGACGCCAGTGATGCTAGACTGCTGGTTTTTCCGATTCGCGTGTAATGGGTGAG
TGAGCTGATGTGGTCGCCAAGACATGTGCCGGTGTCTTGGTGGTGGGTGACGCCTAATCATC (SEQ ID
NO:3)

S4:
GCTATTTTTGCCTCTTCCCAGACGTTGTCGCAATGGAGGTGTGCTTGCCCAACGGTCATCAGGTCGTGGAC
TTAATTAACAACGCTTTTGAAGGTCGTGTATCAATCTACAGCGCGCAAGAGGGATGGGACAAAACAATCTC
AGCACAGCCAGATATGATGGTATGTGGTGGCGCCGTCGTTTGCATGCATTGTCTAGGTGTTGTTGGATCTC
TACAACGCAAGCTGAAGCATTTGCCTCACCATAGATGTAATCAACAGATCCGTCATCAGGATTACGTCGAT
GTACAGTTCGCAGACCGTGTTACTGCTCACTGGAAGCGGGGTATGCTGTCCTTCGTTGCGCAGATGCACGA
GATGATGAATGACGTGTCGCCAGATGACCTGGATCGTGTGCGTACTGAGGGAGGTTCACTAGTGGAGCTGA
ACCGGCTTCAGGTTGACCCAAATTCAATGTTTAGATCAATACACTCAAGTTGGACAGATCCTTTGCAGGTG
GTGGACGACCTTGACACTAAGCTGGATCAGTACTGGACAGCCTTAAACCTGATGATCGACTCATCCGACTT
GATACCCAACTTTATGATGAGAGACCCATCACACGCGTTCAATGGTGTGAAACTGAAGGGAGATGCTCGTC
AAACCCAATTCTCCAGGACTTTTGATTCGAGATCGAGTTTGGAATGGGGTGTGATGGTTTATGATTACTCT
GAGCTGGATCATGATCCATCGAAGGGCCGTGCTTACAGAAAGGAATTGGTGACGCCAGCTCGAGATTTCGG
TCACTTTGGATTATCCCATTATTCTAGGGCGACTACCCCAATCCTTGGAAAGATGCCGGCCGTATTCTCAG
GAATGTTGACTGGGAACTGTAAAATGTATCCATTCATTAAAGGAACGGCTAAGCTGAAGACAGTGCGCAAG
CTAGTGGAGGCAGTCAATCATGCTTGGGGTGTCGAGAAGATTAGATATGCTCTTGGGCCAGGTGGCATGAC
GGGATGGTACAATAGGACTATGCAACAGGCCCCCATTGTGCTAACTCCTGCTGCTCTCACAATGTTCCCAG
ATACCATCAAGTTTGGGGATTTGAATTATCCAGTGATGATTGGCGATCCGATGATTCTTGGCTAAACACCC
CCATCTTCACAGCGCCGGGCTTGACCAACCTGGTGTGACGTGGACAGGCTTCATTCATC (SEQ ID
NO:4)

Figure 2-1

M1:
GCTATTCGCGGTCATGGCTTACATCGCAGTTCCTGCGGTGGTGGATTCACGTTCGAGTGAGGCTATTGGAC
TGCTAGAATCGTTTGGAGTAGACGCTGGGGCTGACGCGAATGACGTTTCATATCAAGATCATGACTATGTG
TTGGATCAGTTACAGTACATGTTAGATGGATATGAGGCTGGTGACGTTATCGATGCACTCGTCCACAAGAA
TTGGTTACATCACTCTGTCTATTGCTTGTTGCCACCCAAAAGTCAACTATTAGAGTATTGGAAAAGTAATC
CTTCAGCGATACCGGACAACGTTGATCGTCGGCTTCGTAAACGACTAATGCTAAAGAAAGATCTCAGGAAA
GATGATGAATACAATCAGCTAGCGCGTGCTTTCAAGATATCGGATGTCTACGCACCTCTCATCTCATCCAC
GACGTCACCGATGACAATGATACAGAACTTGAATCGAGGCGAGATCGTGTACACCACGACGGACAGGGTAA
TAGGGGCTAGAATCTTGTTATATGCTCCTAGAAAGTACTATGCGTCAACTCTGTCATTTACTATGACTAAG
TGCATCATTCCGTTTGGTAAAGAGGTGGGTCGTGTTCCTCACTCTCGATTTAATGTTGGCACATTTCCGTC
AATTGCTACCCCGAAATGTTTTGTCATGAGTGGGGTTGATATTGAGTCCATCCCAAATGAATTTATCAAGT
TGTTTTACCAGCGCGTCAAGAGTGTTCACGCTAACATACTAAATGACATATCTCCTCAGATCGTCTCTGAC
ATGATAAACAGAAAGCGTCTGCGCGTTCATACTCCATCAGATCGTCGAGCCGCGCAGTTGATGCATTTGCC
TTACCATGTTAAACGAGGAGCGTCTCACGTCGACGTTTACAAGGTGGATGTTGTAGACATGTTGTTCGAGG
TAGTGGATGTGGCCGATGGGTTGCGCAACGTATCTAGGAAACTAACTATGCATACCGTTCCTGTATGTATT
CTTGAAATGTTGGGTATTGAGATTGCGGACTATTGCATTCGTCAAGAGGATGGAATGCTCACAGATTGGTT
CCTACTTTTAACCATGCTATCTGATGGCTTGACTGATAGAAGGACGCATTGTCAATACTTGATTAATCCGT
CAAGTGTGCCTCCTGATGTGATACTTAACATCTCAATTACTGGATTTATAAATAGACATACAATCGATGTC
ATGCCTGACATATATGACTTCGTTAAACCCATTGGCGCTGTGCTGCCTAAGGGATCATTTAAATCAACAAT
TATGAGAGTTCTTGATTCAATATCAATATTAGGAATCCAAATCATGCCGCGCGCGCATGTAGTTGACTCAG
ATGAGGTGGGCGAGCAAATGGAGCCTACGTTTGAGCAGGCGGTTATGGAGATATACAAAGGGATTGCTGGC
GTTGACTCGCTGGATGATCTCATCAAGTGGGTGTTGAACTCGGATCTCATTCCGCATGATGACAGGCTTGG
TCAATTATTTCAAGCGTTTTTGCCTCTCGCAAAGGACTTATTAGCTCCAATGGCCAGAAAGTTTTATGATA
ACTCAATGAGTGAGGGTAGATTGCTAACATTCTCTCATGCCGACAGTGAGTTGCTGAACGCAAATTATTTT
GGTCATTTATTGCGACTAAAAATACCATATATTACAGAGGTTAATCTGATGATTCGCAAGAATCGTGAGGG
TGGAGAGCTATTTCAGCTTGTGTTATCTTATCTATATAAAATGTATGCTACTAGCGCGCAGCCTAAATGGT
TTGGATCATTATTGCGATTGTTAATATGTCCCTGGTTACATATGGAGAAATTAATAGGAGAAGCAGACCCG
GCATCTACGTCGGCTGAAATTGGGTGGCATATCCCTCGTGAACAGCTGATGCAAGATGGATGGTGTGGATG
TGAAGACGGATTCATTCCCTATGTTAGCATACGTGCGCCAAGACTGGTTATAGAGGAGTTGATGGAGAAGA
ACTGGGGCCAATATCATGCCCAAGTTATTGTCACTGATCAGCTTGTCGTAGGCGAACCGCGGAGGGTATCT
GCTAAGGCTGTGATCAAGGGTAACCACTTACCAGTTAAGTTAGTTTCACGATTTGCATGTTTCACATTGAC
GGCGAAGTATGAGATGAGGCTTTCGTGCGGCCATAGCACTGGACGTGGAGCTGCATACAGTGCGAGACTAG
CTTTCCGATCTGACTTGGCGTGATCCGTGACATGCGTAGTGTGACACCTGCTCCTAGGTCAATGGGGGTAG
GGGGCGGGCTAAGACTACGTACGCGCTTCATC (SEQ ID NO:5)

M2:
GGCTAATCTGCTGACCGTTACTCTGCAAAGATGGGGAACGCTTCCTCTATCGTTCAGACGATCAACGTCAC
TGGAGATGGCAATGTATTTAAACCATCAGCTGAAACTTCATCTACCGCTGTACCATCGTTAAGCTTATCAC
CTGGAATGCTGAATCCCGGAGGGGTACCATGGATTGCTGTTGGAGATGAGACATCTGTGACTTCACCAGGC
GCATTACGTCGAATGACGTCAAAGGACATCCCGGACACGGCAATAATCAACACAGACAATTCATCAGGCGC
CGTGCCAAGCGAATCAGCCTTGGTGCCCTACATCGATGAGCCGCTGGTAGTGGTTACAGAGCATGCTATTA
CCAACTTCACCAAAGCTGAGATGGCACTTGAATTCAATCGTGAGTTCCTTGACAAGATGCGTGTGCTGTCA
GTGTCACCAAAATATTCGGATCTTCTGACCTATGTTGACTGCTACGTCGGTGTGTCTGCTCGTCAGGCTTT
AAACAATTTTCAGAAACAAGTGCCTGTGATTACACCTACTAGGCAGACGATGTATGTCGACTCGATACAAG
CGGCCTTGAAAGCTTTAGAAAAGTGGGAGATTGATCTGAGAGTGGCTCAAACGTTGCTGCCTACGAACGTT
CCGATTGGAGAAGTCTCTTGTCCAATGCAGTCGGTAGTGAAACTGCTGGATGATCAGCTGCCAGATGACAG
CCTGATACGGAGGTATCCCAAGGAAGCCGCCGTCGCTTTGGCTAAACGAAACGGGGGAATACAATGGATGG
ACGTATCAGAAGGCACCGTGATGAACGAGGCTGTCAACGCTGTTGCAGCTAGTGCACTGGCACCTTCAGCA
TCAGCCCCACCCTTAGAAGAGAAGTCAAAGTTAACCGAACAAGCGATGGATCTCGTGACCGCGGCTGAGCC
TGAGATAATTGCCTCACTCGCGCCAGTTCCCGCACCCGTGTTTGCCATACCACCTAAACCAGCAGATTATA
ATGTGCGTACTCTGAGGATCGACGAGGCCACTTGGCTGCGAATGATTCCAAAATCAATGAACACACCTTTT
CAAATCCAGGTGACTGATAACACAGGAACTAATTGGCATCTCAATTTGAGGGGGGGGACTCGTGTAGTGAA

Figure 2-2

TCTGGACCAAATCGCTCCGATGCGGTTTGTATTAGATCTAGGGGGAAAGAGTTATAAAGAGACGAGCTGGG
ATCCAAACGGCAAGAAGGTCGGATTCATCGTTTTTCAATCGAAGATACCATTCGAACTTTGGACTGCTGCT
TCACAGATCGGTCAAGCCACGGTGGTTAACTATGTCCAACTATACGCTGAAGACAGCTCATTTACCGCGCA
GTCTATCATTGCTACTACCTCTTTGGCTTATAACTATGAGCCTGAGCAGTTGAATAAGACTGACCCTGAGA
TGAATTATTATCTTTTGGCGACCTTTATAGACTCAGCCGCTATAACGCCAACGAATATGACACAGCCTGAT
GTTTGGGATGCCTTGCTGACGATGTCCCCACTATCAGCTGGCGAGGTGACAGTGAAGGGTGCGGTAGTGAG
TGAAGTAGTCCCTGCAGACTTGATAGGTAGCTACACTCCAGAATCCCTAAACGCCTCACTTCCGAATGATG
CTGCTAGATGCATGATCGATAGAGCTTCGAAGATAGCCGAAGCAATCAAGATTGATGATGATGCTGGACCA
GATGAATATTCCCCAAACTCTGTACCAATTCAAGGTCAGCTTGCTATCTCGCAACTCGAAACTGGATATGG
TGTGCGAATATTCAACCCTAAAGGGATCCTTTCTAAAATTGCATCTAGGGCAATGCAGGCTTTCATTGGTG
ACCCGAGCACAATCATCACGCAGGCGGCGCCAGTGTTATCAGACAAGAATAATTGGATTGCATTGGCACAG
GGAGTGAAAACTAGTCTGCGTACTAAAAGTCTATCAGCGGGAGTGAAGACTGCAGTGAGTAAGCTGAGCTC
ATCTGAGTCTATCCAGAATTGGACTCAAGGATTCTTGGATAAAGTGTCAGCGCATTTTCCAGCACCAAAGC
CCGATTGTCCGACTAGCGGAGATAGTGGTGAATCGTCTAATCGCCGAGTGAAGCGCGACTCATACGCAGGA
GTGGTCAAACGTGGGTACACACGTTAGGCCGCTCGCCCTGGTGACGCGGGGTTAAGGGATGCAGGCAAATC
ATC (SEQ ID NO:6)

M3:
GCTAAAGTGACCGTGGTCATGGCTTCATTCAAGGGATTCTCCGCCAACACTGTTCCAGTTTCTAAGGCCAA
GCGTGACATATCATCTCTTGCCGCTACTCCTGGACTTCGTTCACAATCCTTCACTCCGTCTGTGGATATGT
CTCAATCGCGTGAATTCCTCACAAAGGCAATTGAGCAAGGGTCCATGTCTATACCTTATCAGCATGTGAAT
GTACCGAAAGTTGATCGTAAAGTTGTTAGCCTGGTAGTGCGACCTTTCTCTTCAGGTGCTTTCTCTATCTC
TGGAGTGATTTCGCCAGCCCATGCCTATCTACTAGAGTGTCTACCCCAGCTTGAGCAGGCGATGGCTTTTG
TTGCTTCACCTGAGTCTTTCCAGGCTTCCGACGTCGCGAAGCGCTTTGCCATAAAGCCAGGTATGAGCCTC
CAGGATGCCATCACTGCCTTTATTAACTTTGTGTCCGCGATGCTGAAAATGACGGTGACTCGTCAAAACTT
TGACGTTATTGTGGCTGAGATCGAGAGGCTTGCTTCAACCAGCGTGTCCGTCAGGACTGAAGAAGCGAAGG
TTGCTGATGAGGAGCTAATGCTATTCGGGTTAGATCATAGAGGGCCACAGCAGCTGGATGTTTCTGACGCT
AAAGGGATAATGAAGGCTGCTGATATTCAGACAACTCATGATGTCCATTTGGCACCAGGCGTTGGTAATAT
TGATCCTGAAATCTATAACGAGGGGCGGTTCATGTTCATGCAGCACAAGCCACTTGCGGCGGATCAATCGT
ATTTCACCTTGGAGACTGCGGATTATTTCAAGATTTATCCAACATACGATGAACATGATGGCAGGATGGCT
GACCAAAAGCAGTCGGGATTGATACTGTGTACTAAGGACGAGGTATTGGCTGAGCAAACTATATTTAAACT
GGACGCCCCTGATGACAAGACTGTTCATCTGTTGGATCGCGATGACGACCACGTTGTTGCCAGATTTACTA
AGGTATTTATAGAGGACGTGGCTCCCGGGCATCATGCTGCTCAAAGATCGGGACAACGCTCTGTGCTTGAT
GACCTATATGCGAATACGCAAGTGATTTCCATTACTTCTGCTGCTTTAAAGTGGGTGGTCAAGCACGGCGT
ATCTGATGGAATCGTGAACAGGAAGAATGTCAAAGTGTGTGTTGGTTTTGACCCCCTGTACACCTTGTCTA
CACATAACGGGGTGTCCTTATGTGCCCTGCTGATGGACGAAAAACTCTCTGTGCTGAACAGTGCGTGTCGT
ATGACGTTACGCTCACTCATGAAGACCGGACGCGACGTTGATGCACACAGAGCTTTTCAGCGAGTCCTCTC
TCAAGGATACACATCGCTAATGTGCTACTATCATCCTTCACGGAAGTTGGCATATGGTGAGGTGCTCTTTC
TAGAACGATCCAATGACGTGACAGATGGGATCAAGCTTCAGTTGGACGCATCTAGACAGTGTCATGAATGT
CCTGTGTTGCAGCAGAAAGTGGTTGAGTTAGAGAAACAGATTATTATGCAGAAGTCAATCCAGTCAGACCC
TACCCCAGTGGCGCTGCAACCATTGTTGTCTCAGTTGCGTGAGTTGTCTAGTGAAGTTACTAGGCTACAGA
TGGAGTTGAGTCGAGCTCAGTCCCTGAATGCTCAGTTGGAGGCGGATGTCAAGTCAGCTCAATCATGTAGC
TTGGATATGTATCTGAGACACCACACTTGCATTAATGGTCATGCTAAAGAAGATGAATTGCTTGACGCTGT
GCGTGTCGCGCCGGATGTGAGGAGAGAAATCATGGAAAAGAGGAGTGAAGTGAGACAAGGTTGGTGCGAAC
GTATTTCTAAGGAAGCAGCTGCCAAATGTCAAACTGTTATTGATGACCTGACTTTGATGAATGGAAAGCAA
GCACAAGAGATAACAGAATTACGTGATTCGGCTGAAAAATATGAGAAACAGATTGCAGAGCTGGTGAGTAC
CATCACCCAAAACCAGATAACGTATCAGCAAGAGCTACAAGCCTTGGTAGCGAAAAATGTGGAATTGGACG
CGTTGAATCAGCGTCAGGCTAAGTCTTTGCGTATTACTCCCTCTCTTCTATCAGCCACTCCTATCGATTCA
GTTGATGATGTTGCTGACTTAATTGATTTCTCTGTTCCAACTGATGAGTTGTAAATAATCCGTGATGCAGT
GTTGCCCTAATCCCTTAAGCCTTCCCGACCCCCATTCATC (SEQ ID NO:7)

Figure 3-1

L1:
GCTACACGTTCCACGACAATGTCATCCATGATACTGACTCAGTTTGGACCGTTCATTGAGAGCATTTCAGG
TATCACTGATCAATCGAATGACGTGTTTGAAGATGCAGCAAAAGCATTCTCTATGTTTACTCGCAGCGATG
TCTACAAGGCGCTGGATGAAATACCTTTCTCTGATGATGCGATGCTTCCAATCCCTCCAACTATATATACG
AAACCATCTCACGATTCATATTATTACATTGATGCTCTAAACCGTGTGCGTCGCAAAACATATCAGGGCCC
TGATGACGTGTACGTACCTAATTGTTCTATTGTTGAATTGCTGGAGCCACATGAGACTCTGACATCTTATG
GGCGGTTGTCCGAGGCCATCGAGAATCGTGCCAAGGATGGGGACAGCCAAGCCAGAATCGCCACAACGTAT
GGTAGAATCGCTGAATCTCAAGCTCGACAGATTAAGGCTCCATTGGAGAAGTTTGTGTTGGCACTATTAGT
GGCCGAAGCAGGGGGGTCTTTATATGATCCAGTTTTGCAGAAGTATGATGAGATTCCAGATCTATCGCATA
ATTGCCCTTTATGGTGTTTTAGAGAGATCTGTCGTCACATATCTGGTCCATTACCAGATCGGGCACCTTAT
CTTTACTTATCTGCAGGGGTTTTCTGGTTAATGTCACCACGAATGACGTCTGCAATCCCTCCGCTACTATC
CGATCTTGTTAATTTAGCTATTTTGCAACAAACTGCGGGTTTAGATCCATCATTAGTGAAATTGGGAGTAC
AGATATGCCTTCATGCAGCAGCTAGCTCAAGTTATGCATGGTTTATCTTAAAGACTAAGTCTATTTTTCCT
CAAAACACGTTGCACAGTATGTATGAATCTCTAGAAGGGGATACTGTCCTAATCTTGAATGGTTAGAGCC
TAGATCAGACTATAAGTTCATGTACATGGGAGTCATGCCATTGTCCGCTAAGTATGCTAGGTCGGCGCCGT
CCAATGATAAGAAAGCGCGGGAACTTGGCGAGAAATATGGACTGAGCTCAGTCGTCGGTGAGCTTCGTAAA
CGGACAAAGACGTATGTTAAACATGACTTTGCTTCAGTGAGGTACATTCGTGACGCTATGGCATGTACTAG
CGGTATTTTCTTGGTAAGAACACCCACCGAAACGGTATTGCAAGAATATACGCAGAGTCCGGAGATTAAGG
TTCCCATTCCCCAGAAAGACTGGACAGGCCCAATAGGTGAAATCAGAATTCTAAAAGATACAACAAGTTCC
ATCGCGCGTTACTTATATAGAACATGGTACTTGGCAGCGGCGAGAATGGCGGCTCAACCACGTACGTGGGA
TCCATTGTTTCAAGCGATTATGAGATCTCAATACGTGACAGCTAGGGGTGGATCTGGCGCAGCACTCCGCG
AATCTTTGTATGCAATCAATGTGTCGTTACCTGATTTCAAGGGCTTACCAGTGAAGGCAGCAACTAAGATA
TTCCAGGCGGCACAATTAGCGAACTTGCCGTTCTCCCACACATCAGTGGCTATACTAGCTGACACTTCAAT
GGGATTGCGAAATCAGGTGCAGAGGCGGCCACGATCCATTATGCCATTAAATGTGCCCCAGCAGCAGGTTT
CGGCGCCCCATACATTGACAGCGGATTACATTAACTACCACATGAATCTATCAACCACGTCTGGTAGTGCG
GTCATTGAGAAGGTGATTCCTTTAGGTGTATACGCTTCGAGCCCTCCTAACCAGTCGATCAACATTGACAT
ATCTGCGTGTGACGCTAGTATTACTTGGGATTTCTTTCTGTCAGTGATTATGGCGGCTATACACGAAGGTG
TCGCTAGTAGCTCCATTGGAAAACCATTTATGGGGGTTCCTGCATCCATTGTAAATGATGAGTCTGTCGTT
GGAGTGAGAGCTGCTAGGCCGATATCGGGAATGCAGAACATGATTCAGCATCTATCGAAACTATATAAACG
TGGATTTTCATATAGAGTAAACGATTCTTTTTCTCCAGGTAACGATTTTACTCATATGACTACCACTTTCC
CGTCAGGTTCAACAGCCACCTCTACTGAGCATACTGCTAATAATAGTACGATGATGGAAACTTTCCTGACA
GTATGGGGACCCGAACATACTGACGACCCTGACGTCTTACGTTTAATGAAGTCTTTAACTATTCAAAGGAA
TTACGTATGTCAAGGTGATGATGGATTAATGATTATCGATGGGACTACTGCTGGTAAGGTGAACAGTGAAA
CTATTCAGAAGATGCTAGAATTAATCTCAAAATATGGTGAGGAATTCGGATGGAAATATGACATAGCGTAC
GATGGGACTGCCGAATACTTAAAGCTATACTTCATATTTGGCTGTCGAATTCCAAATCTTAGTCGCCATCC
AATCGTGGGGAAAGAACGGGCGAATTCTTCAGCAGAGGAGCCATGGCCAGCAATTCTAGATCAGATTATGG
GTGTCTTCTTTAATGGTGTTCATGATGGGTTACAGTGGCAGCGGTGGATACGTTATTCATGGGCTCTATGC
TGTGCTTTCTCACGTCAAAGAACAATGATTGGTGAGAGCGTGGGTTACCTTCAATATCCTATGTGGTCTTT
TGTCTACTGGGGATTACCACTGGTTAAAGCGTTTGGGTCAGACCCATGGATATTTTCTTGGTACATGCCTA
CTGGAGATCTGGGAATGTATAGTTGGATTAGCTTGATACGCCCTCTGATGACAAGATGGATGGTGGCTAAT
GGTTACGTAACTGACAGATGCTCACCCGTATTCGGGAACGCAGATTATCGCAGGTGTTTCAATGAACTTAA
ACTATATCAAGGTTATTATATGGCACAATTGCCCAGGAATCCTAAGAAGTCTGGACGAGCGGCCCCTCGGG
AGGTAAGAGAACAATTCACTCAGGCATTATCCGACTATCTACTGCAAAATCCAGAGCTGAAGTCACGTGTG
CTACGTGGTCGTAGTGAGTGGGAGAAATATGGAGCGGGGATAATTCACAATCCTCCGTCATTATTCGATGT
GCCCCATAAATGGTATCAGGGTGCGCAAGAGGCAGCAATCGCTACGAGAGAAGAGCTGGCAGAAATGGATG
AGACATTAATGCGCGCTCGAAGGCACAGATATTCGAGCTTTTCAAAGTTATTAGAGGCGTATCTGCTCGTG
AAATGGCGAATGTGCGAGGCCCGCGAACCGTCGGTGGATTTGCGATTACCATTATGTGCGGGTATTGACCC
ATTAAACTCAGATCCTTTTCTCAAGATGGTAAGCGTTGGACCAATGCTCCAGAGTACGAGAAAGTACTTTG
CTCAGACACTATTCATGGCAAAGACGGTGTCGGGTCTTGACGTTAACGCGATTGATAGCGCGTTATTACGA
CTGCGAACATTAGGTGCTGATAAGAAAGCATTAACGGCGCAGTTATTAATGGTGGGCTTCAGGAGTCAGA
AGCGGACGCATTGGCCGGGAAGATAATGCTACAGGATGTGAATACTGTGCAATTAGCCAGAGTGGTTAACT
TAGCTGTGCCAGATACTTGGATGTCGTTAGACTTTGACTCTATGTTCAAACACCACGTCAAGCTGCTTCCC
AAAGATGGACGTCATCTAAATACTGATATTCCTCCTCGAATGGGATGGTTACGGGCCATTTTACGATTCTT

Figure 3-2

AGGTGCCGGAATGGTAATGACTGCGACTGGAGTTGCTGTCGACATCTATCTGGAGGATATACATGGCGGTG
GTCGGTCACTTGGACAGAGATTCATGACTTGGATGCGACAGGAAGGACGGTCAGCGTGAGTCTACCATGGG
TCGTGGTGCGTCAACTCATC  (SEQ ID NO:8)

L2:
GCTAAATGGCGCGATGGCGAACGTTTGGGGGGTGAGACTTGCAGACTCGTTATCTTCACCCACTATTGAGA
CACGAACGCGTCAGTATACCTTACACGATCTTTGCTCAGACCTAGATGCTAATCCGGGGAGGGAACCGTGG
AAACCTCTGCGTAATCAGCGTACTAATAATATTGTGGCTGTGCAATTATTCAGACCATTGCAGGGTTTAGT
TTTAGATACCCAGCTTTATGGATTTCCAGGAGCATTTGATGACTGGGAGCGATTCATGAGAGAGAAGCTGC
GTGTGCTAAAGTATGAAGTATTGCGCATCTATCCAATCAGCAACTATAGCAATGAACATGTCAACGTCTTC
GTGGCCAATGCTTTGGTGGGCGCTTTCCTGTCGAATCAAGCTTTCTATGACCTGCTACCGTTGTTGATAAT
TAATGACACTATGATTGGTGATCTACTTGGCACGGGGCATCGCTATCACAGTTCTTTCAATCTCATGGAG
ATGTGCTGGAAGTCGCAGCTGGTCGTAAGTATCTGCAGATGGAAAACTACTCCAACGATGACGATGATCCT
CCATTATTTGCGAAAGACCTGTCAGATTATGCTAAAGCATTCTACAGTGACACATATGAAGTGTTGGACAG
GTTCTTTTGGACGCATGACTCTTCAGCGGGGTCTTAGTGCATTATGATAAGCCAACGAATGGTCATCACT
ATCTGCTGGGTACTTTGACTCAGATGGTCAGTGCACCTCCTTATATTATTAACGCTACTGACGCAATGTTG
CTTGAATCCTGTCTAGAACAGTTCTCAGCTAATGTGCGTGCGAGACCTGCGCAACCCGTTACACGCTTAGA
CCAATGCTATCATTTAAGATGGGGAGCACAATATGTAGGAGAAGATTCACTGACATATCGGTTGGGGTGT
TATCCTTGCTGGCTACCAATGGATATCAATTAGCTAGACCGATTCCAAGACAGTTGACGAATCGATGGTTG
TCGAGCTTTGTGAGTCAAATTATGTCTGACGGCGTCAACGAGACTCCACTGTGGCCCCAAGAAAGGTATGT
GCAGATCGCTTATGATTCACCATCCGTTGTTGATGGGGCTACGCAATATGGCTATGTCAGGAAGAATCAAC
TCAGACTCGGCATGAGAATATCGGCGCTGCAATCGCTGAGTGATACGCCCTCGCCGGTACAGTGGCTTCCA
CAATACACCATCGACCAGGCAGCGATGGACGAAGGCGATCTGATGGTTAGTCGGCTTACGCAACTCCCGTT
ACGTCCTGATTATGGTAATATCTGGGTCGGCGATGCGCTATCCTATTATGTGGACTACAATCGGAGTCATC
GAGTCGTGCTTTCATCGGAACTTCCTCAGCTTCCGGACACATATTTTGATGGCGATGAACAGTATGGGCGC
AGCCTGTTCTCACTAGCTCGTAAGATTGGTGACCGCTCGTTAGTGAAAGATACGGCTGTCTTGAAGCACGC
TTACCAAGCCATCGATCCAAATACTGGTAAGGAGTATCTGAGATCTCGGCAATCTGTCGCATATTTTGGTG
CATCAGCGGGTCATTCTGGTGCCGACCAGCCGTTAGTCATAGAGCCCTGGATTCAAGGGAAAATCAGTGGT
GTGCCGCCACCCTCCTCAGTGCGACAGTTCGGCTATGATGTTGCCCGTGGCGCGATCGTCGATCTGGCGAG
ACCATTTCCTTCTGGAGATTATCAATTTGTCTATTCGGATGTTGACCAGGTGGTCGATGGCCATGACGATC
TGAGTATATCATCTGGACTGGTGGAGAGCCTTTTGTCTTCATGCATGCACGCCACAGCACCCGGGGGCTCA
TTTGTTGTTAAGATAAATTTTCCGACTAGACCCGTATGGCACTACATCGAACAGAAGATCTTGCCCAATAT
TACGTCATACATGTTGATCAAGCCTTTCGTCACCAACAACGTCGAATTGTTCTTCGTCGCTTTCGGTGTGC
ATCAACACTCATCACTTACTTGGACATCTGGAGTGTACTTCTTCTTGGTGGACCATTTTTATCGTTATGAG
ACTTTATCTACGATCTCACGACAATTGCCGTCTTTTGGGTATGTTGATGATGGGTCTTCCGTGACTGGTAT
CGAGACAATTAGTATTGAGAACCCTGGCTTCTCGAATATGACCCAGGCCGCTCGCATTGGTATCTCAGGAT
TGTGTGCTAATGTAGGTAACGCGCGTAAGTCCATTGCCATTTACGAATCTCATGGGGCCAGAGTATTAACT
ATCACATCAAGGAGATCTCCGGCATCAGCTAGAAGAAAGTCTAGGTTGCGATATTTGCCATTAATAGACCC
TAGGTCGTTAGAGGTACAGGCGCGCACTATTCTGCCAGCTGATCCAGTGTTATTTGAAAACGTGAGCGGAG
CGTCACCCCATGTTTGTCTGACAATGATGTACAACTTCGAAGTGTCGTCAGCGGTATATGATGGAGACGTT
GTGCTAGATCTTGGGACGGGACCAGAGGCTAAAATCCTTGAACTGATACCCGCAACCTCTCCAGTCACATG
CGTGGACATACGGCCTACAGCGCAGCCTAGTGGATGTTGGAACGTTCGTACCACGTTCCTTGAGTTAGATT
ATTTGAGCGATGGATGGATCACTGGGGTGCGTGGGACATAGTTACTTGTATGTTATCTTTGGGGCCGCT
GCCGCTGGAAAATCAATGACTTTTGACGCTGCGTTTCAGCAATTAATCAAAGTATTATCCAAGAGTACGGC
TAATGTTGTGCTGGTGCAGGTTAACTGCCCTACAGACGTGGTGAGGAGCATTAAGGGCTACCTAGAGATAG
ATTCGACTAACAAGAGGTATAGGTTCCCCAAATTTGGTCGAGACGAGCCGTACTCTGACATGGATGCGCTG
GAGAAAATATGTCGTACCGCCTGGCCAAACTGCTCAATTACCTGGGTTCCATTGTCATACGACTTGCGGTG
GACTAGACTGGCATTATTAGAGTCCACGACATTGAGTAGCGCGTCGATTAGAATTGCTGAGCTGATGTATA
AATACATGCCTATTATGAGGATTGATATTCATGGACTACCCATGGAAAAGCGAGGTAACTTCATAGTGGGG
CAGAACTGCTCATTAGTAATCCCTGGTTTTAATGCGCAGGATGTCTTTAACTGTTATTTCAATTCCGCCCT
CGCTTTCTCGACTGAAGATGTCAATGCTGCGATGATTCCCCAAGTGTCTGCGCAGTTTGATGCGACTAAGG
GTGAGTGGACGTTGGATATGGTCTTCTCCGACGCAGGAATCTATACCATGCAGGCTCTAGTGGGATCTAAT

Figure 3-3

GCTAATCCAGTCTCTTTGGGTTCCTTTGTAGTTGATTCTCCAGATGTAGATATAACTGACGCTTGGCCAGC
TCAGTTAGACTTTACGATCGCGGGAACTGATGTCGATATAACAGTTAATCCTTATTACCGTCTGATGACCT
TTGTAAGGATCGATGGACAGTGGCAGATTGCCAATCCAGACAAATTTCAATTCTTTTCGTCGGCGTCTGGG
ACGTTAGTGATGAACGTCAAATTAGATATCGCAGATAAATATCTACTATACTATATACGAGATGTCCAGTC
TCGAGATGTTGGCTTTTACATTCAGCATCCACTTCAACTTTTGAATACGATCACATTGCCAACCAACGAGG
ACCTTTTTCTGAGCGCACCTGACATGCGAGAGTGGGCAGTTAAGGAAAGCGGTAACACGATATGTATACTC
AATAGTCAAGGGTTTGTGCTACCTCAAGATTGGGATGTGTTAACAGATACCATAAGTTGGTCCCCATCGAT
ACCCACATACATTGTGCCACCGGGTGATTATACCTTGACTCCTCTGTAACTCACTGTCCCTCGTGAGCGCG
CCTAATTCATC (SEQ ID NO:9)

L3:
GCTAATCGTCAGGATGAAGCGGATTCCAAGGAAGACAAAGGGCAAATCCAGCGGAAAGGGCAATGACTCAA
CAGAGAGAGCGGACGATGGCTCGAGCCAATTAAGAGACAAGCAAAACAATAAGGCTGGCCCCGCCACTACG
GAGCCTGGCACATCCAACCGAGAGCAATACAAAGCTCGACCAGGTATTGCATCTGTGCAGAGGGCCACTGA
AAGTGCAGAAATGCCCATGAAGAATAATGACGAAGGGACGCCAGATAAGAAAGGAAATACTAAGGGCGACC
TAGTTAATGAGCATAGTGAGGCTAAAGACGAGGCGGATGAAGCGACGAAGAAGCAGGCAAAGGATACAGAC
AAAAGTAAAGCGCAAGTCACATATTCAGACACTGGTATCAATAATGCTAATGAACTGTCAAGATCTGGGAA
TGTGGATAATGAGGGTGGAAGTAATCAGAAGCCGATGTCTACCAGAATAGCTGAGGCAACGTCTGCTATAG
TGTCGAAACATCCTGCGCGTGTTGGGCTGCCACCTACCGCTAGCAGTGGTCATGGGTATCAGTGCCATGTC
TGTTCTGCAGTCCTGTTTAGTCCTTTAGACCTAGATGCCCACGTCGCCTCACATGGTTTGCATGGTAACAT
GACATTAACATCGAGTGATATCCAGCGACATATAACTGAGTTCATCAGCTCATGGCAAAATCATCCTATTG
TTCAAGTTTCGGCTGATGTCGAAAATAAGAAAACTGCTCAATTGCTTCACGCTGACACTCCTCGACTCGTC
ACTTGGGATGCTGGTTTGTGTACTTCATTCAAAATCGTCCCGATTGTGCCAGCTCAGGTGCCGCAGGATGT
ACTGGCCTATACGTTTTTCACCTCTTCATACGCTATCCAATCACCGTTTCCAGAGGCGGCAGTGTCTAGGA
TTGTGGTGCATACGAGATGGGCATCTAATGTTGACTTTGACCGAGACTCGTCTGTCATCATGGCGCCACCT
ACAGAAAACAATATCCATTTGTTTAAACAGTTACTAAATACTGAAACCCTGTCTGTAAGGGGGGCTAATCC
GCTAATGTTCAGGGCGAATGTGTTGCATATGTTGCTAGAGTTCGTATTAGATAACTTGTATCTGAACAGAC
ATACGGGATTCTCTCAAGACCACACGCCATTTACTGAGGGTGCTAATTTGCGTTCACTTCCTGGCCCCGAT
GCTGAGAAATGGTACTCGATTATGTATCCAACGCGCATGGGAACGCCGAATGTATCCAAAATATGTAATTT
CGTCGCCTCTTGTGTGCGAAATCGGGTTGGACGGTTTGATCGAGCACAGATGATGAACGGAGCTATGTCAG
AGTGGGTGGATGTCTTCGAGACTTCAGACGCGCTAACCGTCTCCATTCGAGGTCGATGGATGGCTAGACTA
GCTCGCATGAACATAAATCCAACAGAGATCGAATGGGCATTGACTGAATGTGCACAAGGATATGTGACTGT
CACAAGTCCTTACGCTCCTAGCGTAAATAGATTGATGCCCTATCGTATCTCCAACGCTGAGCGGCAAATAT
CACAGATAATCAGGATCATGAACATTGGCAATAACGCGACGGTGATACAACCTGTTCTGCAAGATATTTCG
GTACTCCTTCAACGCATATCACCACTCCAAATAGATCCAACTATTATTTCCAACACTATGTCAACAGTCTC
GGAGTCTACTACTCAGACCCTCAGCCCCGCGTCCTCAATTTTGGGTAAACTACGACCAAGCAACTCAGATT
TTTCTAGTTTTAGAGTCGCGTTGGCTGGATGGCTTTATAATGGGGTTGTGACGACGGTGATTGATGATAGT
TCATATCCAAAAGACGGCGGCAGCGTGACCTCACTTGAAAATCTGTGGGATTTCTTCATCCTTGCGCTTGC
TCTACCACTGACAACTGACCCCTGTGCACCTGTGAAAGCATTCATGACCCTAGCCAACATGATGGTTGGTT
TCGAGACAATCCCTATGGATAATCAGATCTATACTCAATCGAGACGCGCGAGTGCTTTCTCAACGCCTCAC
ACGTGGCCACGATGCTTTATGAACATCCAGTTAATTTCTCCAATCGACGCTCCCATCTTGCGACAGTGGGC
TGAAATTATTCATAGATACTGGCCTAACCCTTCACAGATTCGTTATGGTGCACCGAACGTTTTCGGCTCGG
CAAATTTGTTCACTCCACCTGAGGTGCTGTTATTGCCAATCGATCATCAACCAGCTAATGTAACAACGCCA
ACGCTGGACTTCACCAATGAGTTAACTAATTGGCGCGCTCGTGTCTGTGAGCTTATGAAGAATCTCGTTGA
TAACCAAAGATATCAACCTGGATGGACACAAAGTCTAGTCTCGTCAATGCGCGGAACGCTAGACAAATTGA
AGTTGATTAAATCGATGACACCAATGTATCTGCAACAGCTGGCTCCGGTAGAGTTAGCAGTGATAGCTCCC
ATGTTGCCTTTTCCACCTTTCCAGGTGCCATACGTCCGTCTCGATCGTGACAGAGTTCCAACAATGGTTGG
AGTAACACGACATTCACGAGATACTATTACTCAGCCGGCGCTATCGCTGTCGACAACCAATACTACTGTTG
GCGTGCCACTAGCTCTAGACGCGAGGGCTATCACCGTTGCGCTGTTGTCAGGGAAATATCCGCCGGATTTG
GTGACAAATGTATGGTACGCTGATGCCATTTACCCAATGTATGCAGACACGGAGGTGTTCTCTAATCTTCA
GAGAGACATGATTACCTGCGAGGCCGTGCAGACATTAGTGACTCTGGTGGCGCAAATATCAGAGACCCAGT
ATCCTGTAGATAGGTATCTTGATTGGATCCCATCACTGAGAGCATCGGCGGCGACGGCGGCGACATTTGCT

Figure 3-4

```
GAGTGGGTTAATACTTCAATGAAGACGGCGTTTGATTTGTCTGATATGCTGTTAGAGCCTCTCCTAAGCGG
TGATCCGAGGATGACTCAACTAGCGATTCAGTATCAGCAGTACAATGGCAGAACGTTTAATATCATACCTG
AAATGCCAGGTTCAGTAATTGCTGACTGCGTTCAATTAACAGCAGAAGTCTTTAATCACGAATATAACCTG
TTTGGGATTGCGCGGGGTGATATCATCATTGGCCGTGTTCAGTCGACACATTTGTGGTCACCGCTGGCTCC
TCCACCTGACCTGGTGTTTGATCGTGATACCCCTGGTGTTCACATCTTCGGACGAGATTGCCGTATATCGT
TTGGAATGAATGGCGCCGCGCCAATGATTAGAGATGAGACTGGACTGATGGTGCCTTTTGAAGGAAATTGG
ATTTTCCCACTGGCGCTTTGGCAAATGAATACACGATATTTTAATCAACAGTTCGACGCGTGGATTAAGAC
AGGAGAGTTGCGAATCCGCATTGAGATGGGCGCGTATCCATATATGTTGCATTACTATGATCCACGTCAGT
ACGCTAATGCATGGAATTTAACATCCGCCTGGCTTGAAGAAATTACGCCGACGAGCATCCCATCCGTGCCT
TTCATGGTGCCCATTTCAAGTGATCATGACATTTCCTCTGCCCCAGCTGTCCAATATATCATTTCAACTGA
ATATAATGATCGGTCTCTGTTCTGCACTAACTCATCATCTCCCCAAACCATCGCTGGACCAGACAAACACA
TTCCAGTTGAGAGATATAACATTCTGACCAACCCCGACGCTCCACCCACGCAGATACAACTGCCTGAAGTC
GTTGACTTGTACAACGTCGTCACACGCTATGCGTATGAGACTCCGCCTATTACCGCTGTTGTTATGGGTGT
TCCTTGATCCTCATCCTCCCAACAGGTGCTAGAGCATTGCGCTCAATGCTAGTTGGGCCGATTCATC
(SEQ ID NO:10)
```

Figure 4

σ1:
MDPRLREEVVRLIIALTSDNGASLSKGLESRVSALEKTSQIHSDTILRITQGLDDANKRIIALEQSRDDLVASVSDA
QLAISRLESSIGALQTVVNGLDSSVTQLGARVGQLETGLAELRVDHDNLVARVDTAERNIGSLTTELSTLTLRVTSI
QADFESRISTLERTAVTSAGAPLSIRNNRMTMGLNDGLTLSGNNLAIRLPGNTGLNIQNGGLQFRFNTDQFQIVNNN
LTLKTTVFDSINSRIGATEQSYVASAVTPLRLNSSTKVLDMLIDSSTLEINSSGQLTVRSTSPNLRYPIADVSGGIG
MSPNYRFRQSMWIGIVSYSGSGLNWRVQVNSDIFIVDDYIHICLPAFDGFSIADGGDLSLNFVTGLLPPLLTGDTEP
AFHNDVVTYGAQTVAIGLSSGGAPQYMSKNLWVEQWQDGVLRLRVEGGGSITHSNSKWPAMTVSYPRSFT (SEQ
ID NO:11)

σ2:
MARAAFLFKTVGFGGLQNVPINDELSSHLLRAGNSPWQLTQFLDWISLGRGLATSALVPTAGSRYYQMSCLLSGTLQ
IPFRPNHRWGDIRFLRLVWSAPTLDGLVVAPPQVLAQPALQAQADRVYDCDDYPFLARDPRFKHRVYQQLSAVTLLN
LTGFGPISYVRVDEDMWSGDVNQLLMNYFGHTFAEIAYTLCQASANRPWEYDGTYARMTQIVLSLFWLSYVGVIHQQ
NTYRTFYFQCNRRGDAAEVWILSCSLNHSAQIRPGNRSLFVMPTSPDWNMDVNLILSSTLTGCLCSGSQLPLIDNNS
VPAVSRNIHGWTGRAGNQLHGFQVRRMVTEFCDRLRRDGVMTQAQQNQVEALADQTQQFKRDKLETWAREDDQYNQA
HPNSTMFRTKPFTNAQWGRGNTGATSAAIAALI (SEQ ID NO:12)

σNS:
MASSLRAAISKIKRDDVGQQVCPNYVMLRSSVTTKVVRNVVEYQIRTGGFFSCLAMLRPLQYAKRERLLGQRNLERI
STRDILQTRDLHSLCMPTPDAPMSNHQASTMRELICSYFKVDHADGLKYIPMDERYSPSSLARLFTMGMAGLHITTE
PSYKRVPIMHLAADLDCMTLALPYMITLDGDTVVPVAPTLSAEQLLDDGLKGLACMDMDVRWTRIAGRLVIRVWTLH
AASTSCIARRQQKPSVCLRHALC (SEQ ID NO:13)

MASSLRAAISKIKRDDVGQQVCPNYVMLRSSVTTKVVRNVVEYQIRTGGFFSCLAMLRPLQYAKRERLLGQRNLERI
STRDILQTRDLHSLCMPTPDAPMSNHQASTMRELICSYFKVDHADGLKYIPMDERYSPSSLARLFTMGMAGLHITTE
PSYKRVPIMHLAADLDCMTLALPYMITLDGDTVVPVAPTLSAEQLLDDGLKGLACMDISYGCEVDANSRPAGDQSMD
SSRCINELYCEETAEAICVLKTCLVLNCMQFKLEMDDLAHNAAELDKIQMMIPFSERVFRMASSFATIDAQCFRFCV
MMKDKNLKIDMRETTRLWTRSASDDSVATSSLSISLDRGRWVAADASDARLLVFPIRV (SEQ ID NO:14)

σ3:
MEVCLPNGHQVVDLINNAFEGRVSIYSAQEGWDKTISAQPDMMVCGGAVVCMHCLGVVGSLQRKLKHLPHHRCNQQI
RHQDYVDVQFADRVTAHWKRGMLSFVAQMHEMMNDVSPDDLDRVRTEGGSLVELNRLQVDPNSMFRSIHSSWTDPLQ
VVDDLDTKLDQYWTALNLMIDSSDLIPNFMMRDPSHAFNGVKLKGDARQTQFSRTFDSRSSLEWGVMVYDYSELDHD
PSKGRAYRKELVTPARDFGHFGLSHYSRATTPILGKMPAVFSGMLTGNCKMYPFIKGTAKLKTVRKLVEAVNHAWGV
EKIRYALGPGGMTGWYNRTMQQAPIVLTPAALTMFPDTIKFGDLNYPVMIGDPMILG (SEQ ID NO:15)

Figure 5

μ2:
MAYIAVPAVVDSRSSEAIGLLESFGVDAGADANDVSYQDHDYVLDQLQYMLDGYEAGDVIDALVHKNWLHHSVYCLL
PPKSQLLEYWKSNPSAIPDNVDRRLRKRLMLKKDLRKDDEYNQLARAFKISDVYAPLISSTTSPMTMIQNLNRGEIV
YTTTDRVIGARILLYAPRKYYASTLSFTMTKCIIPFGKEVGRVPHSRFNVGTFPSIATPKCFVMSGVDIESIPNEFI
KLFYQRVKSVHANILNDISPQIVSDMINRKRLRVHTPSDRRAAQLMHLPYHVKRGASHVDVYKVDVVDMLFEVVDVA
DGLRNVSRKLTMHTVPVCILEMLGIEIADYCIRQEDGMLTDWFLLLTMLSDGLTDRRTHCQYLINPSSVPPDVILNI
SITGFINRHTIDVMPDIYDFVKPIGAVLPKGSFKSTIMRVLDSISILGIQIMPRAHVVDSDEVGEQMEPTFEQAVME
IYKGIAGVDSLDDLIKWVLNSDLIPHDDRLGQLFQAFLPLAKDLLAPMARKFYDNSMSEGRLLTFSHADSELLNANY
FGHLLRLKIPYITEVNLMIRKNREGGELFQLVLSYLYKMYATSAQPKWFGSLLRLLICPWLHMEKLIGEADPASTSA
EIGWHIPREQLMQDGWCGCEDGFIPYVSIRAPRLVIEELMEKNWGQYHAQVIVTDQLVVGEPRRVSAKAVIKGNHLP
VKLVSRFACFTLTAKYEMRLSCGHSTGRGAAYSARLAFRSDLA (SEQ ID NO:16)

μ1:
MGNASSIVQTINVTGDGNVFKPSAETSSTAVPSLSLSPGMLNPGGVPWIAVGDETSVTSPGALRRMTSKDIPDTAII
NTDNSSGAVPSESALVPYIDEPLVVVTEHAITNFTKAEMALEFNREFLDKMRVLSVSPKYSDLLTYVDCYVGVSARQ
ALNNFQKQVPVITPTRQTMYVDSIQAALKALEKWEIDLRVAQTLLPTNVPIGEVSCPMQSVVKLLDDQLPDDSLIRR
YPKEAAVALAKRNGGIQWMDVSEGTVMNEAVNAVAASALAPSASAPPLEEKSKLTEQAMDLVTAAEPEIIASLAPVP
APVFAIPPKPADYNVRTLRIDEATWLRMIPKSMNTPFQIQVTDNTGTNWHLNLRGGTRVVNLDQIAPMRFVLDLGGK
SYKETSWDPNGKKVGFIVFQSKIPFELWTAASQIGQATVVNYVQLYAEDSSFTAQSIIATTSLAYNYEPEQLNKTDP
EMNYYLLATFIDSAAITPTNMTQPDVWDALLTMSPLSAGEVTVKGAVVSEVVPADLIGSYTPESLNASLPNDAARCM
IDRASKIAEAIKIDDDAGPDEYSPNSVPIQGQLAISQLETGYGVRIFNPKGILSKIASRAMQAFIGDPSTIITQAAP
VLSDKNNWIALAQGVKTSLRTKSLSAGVKTAVSKLSSSESIQNWTQGFLDKVSAHFPAPKPDCPTSGDSGESSNRRV
KRDSYAGVVKRGYTR (SEQ ID NO:17)

μNS:
MASFKGFSANTVPVSKAKRDISSLAATPGLRSQSFTPSVDMSQSREFLTKAIEQGSMSIPYQHVNVPKVDRKVVSLV
VRPFSSGAFSISGVISPAHAYLLECLPQLEQAMAFVASPESFQASDVAKRFAIKPGMSLQDAITAFINFVSAMLKMT
VTRQNFDVIVAEIERLASTSVSVRTEEAKVADEELMLFGLDHRGPQQLDVSDAKGIMKAADIQTTHDVHLAPGVGNI
DPEIYNEGRFMFMQHKPLAADQSYFTLETADYFKIYPTYDEHDGRMADQKQSGLILCTKDEVLAEQTIFKLDAPDDK
TVHLLDRDDDHVVARFTKVFIEDVAPGHHAAQRSGQRSVLDDLYANTQVISITSAALKWVVKHGVSDGIVNRKNVKV
CVGFDPLYTLSTHNGVSLCALLMDEKLSVLNSACRMTLRSLMKTGRDVDAHRAFQRVLSQGYTSLMCYYHPSRKLAY
GEVLFLERSNDVTDGIKLQLDASRQCHECPVLQQKVVELEKQIIMQKSIQSDPTPVALQPLLSQLRELSSEVTRLQM
ELSRAQSLNAQLEADVKSAQSCSLDMYLRHHTCINGHAKEDELLDAVRVAPDVRREIMEKRSEVRQGWCERISKEAA
AKCQTVIDDLTLMNGKQAQEITELRDSAEKYEKQIAELVSTITQNQITYQQELQALVAKNVELDALNQRQAKSLRIT
PSLLSATPIDSVDDVADLIDFSVPTDEL (SEQ ID NO:18)

Figure 6-1

λ3:
MSSMILTQFGPFIESISGITDQSNDVFEDAAKAFSMFTRSDVYKALDEIPFSDDAMLPIPPTIYTKPSHDSYYYIDA
LNRVRRKTYQGPDDVYVPNCSIVELLEPHETLTSYGRLSEAIENRAKDGDSQARIATTYGRIAESQARQIKAPLEKF
VLALLVAEAGGSLYDPVLQKYDEIPDLSHNCPLWCFREICRHISGPLPDRAPYLYLSAGVFWLMSPRMTSAIPPLLS
DLVNLAILQQTAGLDPSLVKLGVQICLHAAASSSYAWFILKTKSIFPQNTLHSMYESLEGGYCPNLEWLEPRSDYKF
MYMGVMPLSAKYARSAPSNDKKARELGEKYGLSSVVGELRKRTKTYVKHDFASVRYIRDAMACTSGIFLVRTPTETV
LQEYTQSPEIKVPIPQKDWTGPIGEIRILKDTTSSIARYLYRTWYLAAARMAAQPRTWDPLFQAIMRSQYVTARGGS
GAALRESLYAINVSLPDFKGLPVKAATKIFQAAQLANLPFSHTSVAILADTSMGLRNQVQRRPRSIMPLNVPQQQVS
APHTLTADYINYHMNLSTTSGSAVIEKVIPLGVYASSPPNQSINIDISACDASITWDFFLSVIMAAIHEGVASSSIG
KPFMGVPASIVNDESVVGVRAARPISGMQNMIQHLSKLYKRGFSYRVNDSFSPGNDFTHMTTTFPSGSTATSTEHTA
NNSTMMETFLTVWGPEHTDDPDVLRLMKSLTIQRNYVCQGDDGLMIIDGTTAGKVNSETIQKMLELISKYGEEFGWK
YDIAYDGTAEYLKLYFIFGCRIPNLSRHPIVGKERANSSAEEPWPAILDQIMGVFFNGVHDGLQWQRWIRYSWALCC
AFSRQRTMIGESVGYLQYPMWSFVYWGLPLVKAFGSDPWIFSWYMPTGDLGMYSWISLIRPLMTRWMVANGYVTDRC
SPVFGNADYRRCFNELKLYQGYYMAQLPRNPKKSGRAAPREVREQFTQALSDYLLQNPELKSRVLRGRSEWEKYGAG
IIHNPPSLFDVPHKWYQGAQEAAIATREELAEMDETLMRARRHRYSSFSKLLEAYLLVKWRMCEAREPSVDLRLPLC
AGIDPLNSDPFLKMVSVGPMLQSTRKYFAQTLFMAKTVSGLDVNAIDSALLRLRTLGADKKALTAQLLMVGLQESEA
DALAGKIMLQDVNTVQLARVVNLAVPDTWMSLDFDSMFKHHVKLLPKDGRHLNTDIPPRMGWLRAILRFLGAGMVMT
ATGVAVDIYLEDIHGGGRSLGQRFMTWMRQEGRSA (SEQ ID NO:19)

λ2:
MANVWGVRLADSLSSPTIETRTRQYTLHDLCSDLDANPGREPWKPLRNQRTNNIVAVQLFRPLQGLVLDTQLYGFPG
AFDDWERFMREKLRVLKYEVLRIYPISNYSNEHVNVFVANALVGAFLSNQAFYDLLPLLIINDTMIGDLLGTGASLS
QFFQSHGDVLEVAAGRKYLQMENYSNDDDDPPLFAKDLSDYAKAFYSDTYEVLDRFFWTHDSSAGVLVHYDKPTNGH
HYLLGTLTQMVSAPPYIINATDAMLLESCLEQFSANVRARPAQPVTRLDQCYHLRWGAQYVGEDSLTYRLGVLSLLA
TNGYQLARPIPRQLTNRWLSSFVSQIMSDGVNETPLWPQERYVQIAYDSPSVVDGATQYGYVRKNQLRLGMRISALQ
SLSDTPSPVQWLPQYTIDQAAMDEGDLMVSRLTQLPLRPDYGNIWVGDALSYYVDYNRSHRVVLSSELPQLPDTYFD
GDEQYGRSLFSLARKIGDRSLVKDTAVLKHAYQAIDPNTGKEYLRSRQSVAYFGASAGHSGADQPLVIEPWIQGKIS
GVPPPSSVRQFGYDVARGAIVDLARPFPSGDYQFVYSDVDQVVDGHDDLSISSGLVESLLSSCMHATAPGGSFVVKI
NFPTRPVWHYIEQKILPNITSYMLIKPFVTNNVELFFVAFGVHQHSSLTWTSGVYFFLVDHFYRYETLSTISRQLPS
FGYVDDGSSVTGIETISIENPGFSNMTQAARIGISGLCANVGNARKSIAIYESHGARVLTITSRRSPASARRKSRLR
YLPLIDPRSLEVQARTILPADPVLFENVSGASPHVCLTMMYNFEVSSAVYDGDVVLDLGTGPEAKILELIPATSPVT
CVDIRPTAQPSGCWNVRTTFLELDYLSDGWITGVRGDIVTCMLSLGAAAAGKSMTFDAAFQQLIKVLSKSTANVVLV
QVNCPTDVVRSIKGYLEIDSTNKRYRFPKFGRDEPYSDMDALEKICRTAWPNCSITWVPLSYDLRWTRLALLESTTL
SSASIRIAELMYKYMPIMRIDIHGLPMEKRGNFIVGQNCSLVIPGFNAQDVFNCYFNSALAFSTEDVNAAMIPQVSA
QFDATKGEWTLDMVFSDAGIYTMQALVGSNANPVSLGSFVVDSPDVDITDAWPAQLDFTIAGTDVDITVNPYYRLMT
FVRIDGQWQIANPDKFQFFSSASGTLVMNVKLDIADKYLLYYIRDVQSRDVGFYIQHPLQLLNTITLPTNEDLFLSA
PDMREWAVKESGNTICILNSQGFVLPQDWDVLTDTISWSPSIPTYIVPPGDYTLTPL (SEQ ID NO:20)

λ1:
MKRIPRKTKGKSSGKGNDSTERADDGSSQLRDKQNNKAGPATTEPGTSNREQYKARPGIASVQRATESAEMPMKNND
EGTPDKKGNTKGDLVNEHSEAKDEADEATKKQAKDTDKSKAQVTYSDTGINNANELSRSGNVDNEGGSNQKPMSTRI
AEATSAIVSKHPARVGLPPTASSGHGYQCHVCSAVLFSPLDLDAHVASHGLHGNMTLTSSDIQRHITEFISSWQNHP
IVQVSADVENKKTAQLLHADTPRLVTWDAGLCTSFKIVPIVPAQVPQDVLAYTFFTSSYAIQSPFPEAAVSRIVVHT
RWASNVDFDRDSSVIMAPPTENNIHLFKQLLNTETLSVRGANPLMFRANVLHMLLEFVLDNLYLNRHTGFSQDHTPF
TEGANLRSLPGPDAEKWYSIMYPTRMGTPNVSKICNFVASCVRNRVGRFDRAQMMNGAMSEWVDVFETSDALTVSIR
GRWMARLARMNINPTEIEWALTECAQGYVTVTSPYAPSVNRLMPYRISNAERQISQIIRIMNIGNNATVIQPVLQDI
SVLLQRISPLQIDPTIISNTMSTVSESTTQTLSPASSILGKLRPSNSDFSSFRVALAGWLYNGVVTTVIDDSSYPKD
GGSVTSLENLWDFFILALALPLTTDPCAPVKAFMTLANMMVGFETIPMDNQIYTQSRRASAFSTPHTWPRCFMNIQL
ISPIDAPILRQWAEIIHRYWPNPSQIRYGAPNVFGSANLFTPPEVLLLPIDHQPANVTTPTLDFTNELTNWRARVCE
LMKNLVDNQRYQPGWTQSLVSSMRGTLDKLKLIKSMTPMYLQQLAPVELAVIAPMLPFPPFQVPYVRLDRDRVPTMV
GVTRHSRDTITQPALSLSTTNTTVGVPLALDARAITVALLSGKYPPDLVTNVWYADAIYPMYADTEVFSNLQRDMIT
CEAVQTLVTLVAQISETQYPVDRYLDWIPSLRASAATAATFAEWVNTSMKTAFDLSDMLLEPLLSGDPRMTQLAIQY

Figure 6-2

```
QQYNGRTFNIIPEMPGSVIADCVQLTAEVFNHEYNLFGIARGDIIIGRVQSTHLWSPLAPPPDLVFDRDTPGVHIFG
RDCRISFGMNGAAPMIRDETGLMVPFEGNWIFPLALWQMNTRYFNQQFDAWIKTGELRIRIEMGAYPYMLHYYDPRQ
YANAWNLTSAWLEEITPTSIPSVPFMVPISSDHDISSAPAVQYIISTEYNDRSLFCTNSSSPQTIAGPDKHIPVERY
NILTNPDAPPTQIQLPEVVDLYNVVTRYAYETPPITAVVMGVP (SEQ ID NO:21)
```

REOVIRUSES HAVING MODIFIED SEQUENCES

CROSS-REFERENCE TO RELATED APPLICATIONS

This application claims priority under 35 U.S.C. 119(e) to U.S. Application No. 60/894,425 filed on Mar. 12, 2007 and U.S. Application No. 60/989,568 filed on Nov. 21, 2007, both of which are incorporated herein by reference.

TECHNICAL FIELD

This invention relates to viruses, and more particularly to reoviruses having modified sequences.

BACKGROUND

The name reovirus derives from an acronym for respiratory and enteric orphan virus, reflecting that the initial isolates came from human respiratory and enteric tracts but were not associated with serious disease. Reoviruses have a double-stranded, segmented RNA genome. The virions measure 60-80 nm in diameter and possess two concentric capsid shells, each of which is icosahedral. The mammalian reovirus genome consists of double-stranded RNA in 10 discrete segments with a total genome size of ~23.5 kbp. The individual RNA segments vary in size.

Three serologically distinct but related types of reovirus have been recovered from mammalian species: type 1 (representative strains include, for example, Lang (T1L)), type 2 (representative strains include, for example, Jones (T2J)) and type 3 (representative strains include, for example, Dearing or Abney (T3D or T3A, respectively)). The three serotypes are easily identifiable on the basis of neutralization and hemagglutinin-inhibition assays (see, for example, Sabin, 1959, *Science*, 130:966; Fields, et al., 1996, *Fundamental Virology*, 3rd Ed., Lippincott-Raven; Rosen, 1960, *Am. J. Hyg.*, 71:242; and Stanley, 1967, *Br. Med. Bull.*, 23:150).

SUMMARY

Provided herein are reoviruses having modified nucleic acid and polypeptide sequences. Sequence modifications include, for example, modifications in one or more of the reovirus genome segments. Also provided are pharmaceutical compositions that include reoviruses having a modified sequence as well as methods of using such reoviruses.

In one aspect, the invention provides a reovirus that has a lambda-3 polypeptide having one or more amino acid modifications; a sigma-3 polypeptide having one or more amino acid modifications; a mu-1 polypeptide having one or more amino acid modifications; and/or a mu-2 polypeptide having one or more amino acid modifications. Such a reovirus can be, for example, non-naturally occurring. In another aspect, the invention provides a reovirus lambda-3 polypeptide having one or more amino acid modifications; a reovirus sigma-3 polypeptide having one or more amino acid modifications; a reovirus mu-1 polypeptide having one or more amino acid modifications; and/or a reovirus mu-2 polypeptide having one or more amino acid modifications.

By way of example, the one or more amino acid modifications in the lambda-3 polypeptide can be a Val at residue 214, an Ala at residue 267, a Thr at residue 557, a Lys at residue 755, a Met at residue 756, a Pro at residue 926, a Pro at residue 963, a Leu at residue 979, an Arg at residue 1045, a Val at residue 1071, or any combination thereof, numbered relative to GenBank Accession No. M24734.1. It is noted that, when the amino acid sequence is a Val at residue 214 or a Val at residue 1071, the amino acid sequence further includes at least one additional change in the amino acid sequence. In one embodiment, the lambda-3 polypeptide includes the sequence shown in SEQ ID NO:19.

Further by way of example, the one or more amino acid modifications in the sigma-3 polypeptide can be a Leu at residue 14, a Lys at residue 198, or any combination thereof, numbered relative to GenBank Accession No. K02739. It is noted that, when the amino acid sequence is a Leu at residue 14, the amino acid sequence further includes at least one additional change in the amino acid sequence. In one embodiment, the sigma-3 polypeptide includes the sequence shown in SEQ ID NO:15.

Further by way of example, the one or more amino acid modifications in the mu-1 polypeptide can be an Asp at residue 73 numbered relative to GenBank Accession No. M20161.1. In one embodiment, the mu-1 polypeptide includes the sequence shown in SEQ ID NO:17.

Also by way of example, the amino acid modification mu-2 polypeptide can be a Ser at residue 528 numbered relative to GenBank Accession No. AF461684.1. In one embodiment, the mu-4-2 polypeptide includes the sequence shown in SEQ ID NO:16.

A reovirus as described herein having one or more modifications can further include a reovirus sigma-2 polypeptide. Such a sigma-2 polypeptide can have a Cys at one or more of position 70, 127, 195, 241, 255, 294, 296, or 340, numbered relative to GenBank Accession No. NP 694684.1. In one embodiment, the sigma-2 polypeptide includes the sequence shown in SEQ ID NO:12.

In another aspect, the invention provides a reovirus that has a L1 genome segment having one or more nucleic acid modifications; a S4 genome segment having one or more nucleic acid modifications; a M1 genome segment having one or more nucleic acid modifications; and/or a M2 genome segment having one or more nucleic acid modifications. Such a reovirus can be, for example, non-naturally occurring. In another aspect, the invention provides a L1 genome segment having one or more nucleic acid modifications; a S4 genome segment having one or more nucleic acid modifications; a M1 genome segment having one or more nucleic acid modifications; and/or a M2 genome segment having one or more nucleic acid modifications.

By way of example, the one or more nucleic acid modifications in the L1 genome segment can be a T at position 660, a G at position 817, an A at position 1687, a G at position 2283, an ATG at positions 2284-2286, a C at position 2794, a C at position 2905, a C at position 2953, an A at position 3153, or a G at position 3231, numbered relative to GenBank Accession No. M24734.1. In one embodiment, the L1 genome segment includes the sequence shown in SEQ ID NO:8.

Further by way of example, the one or more nucleic acid modifications in the S4 genome segment can be an A at position 74 and an A at position 624, numbered relative to GenBank Accession No. K02739. In one embodiment, the S4 genome segment includes the sequence shown in SEQ ID NO:4.

Further by way of example, the nucleic acid modification in the M2 genome segment can be a C at position 248, numbered relative to GenBank Accession No. M20161.1. In one embodiment, the M2 genome segment includes the sequence shown in SEQ ID NO:6.

Also by way of example, the nucleic acid modification in the M1 genome segment can be a T at position 1595, numbered relative to GenBank Accession No. AF461684.1. In one embodiment, the M1 genome segment includes the sequence shown in SEQ ID NO:5.

A reovirus as described herein can include any modification or combination of modifications disclosed herein. In some embodiments, a reovirus as described herein is a reassortant. In certain embodiments, a reovirus as described herein includes genomic segments having the sequences shown in SEQ ID NOs:1-10 or the polypeptides shown in SEQ ID NOs:11, 12, and 16-21, and either or both SEQ ID NO:13 or 14. In one embodiment, a reovirus as disclosed herein is identified as IDAC Accession No. 190907-01.

A reovirus as disclosed herein generally exhibits a growth advantage over a reovirus that does not contain a corresponding modification. Representative growth advantages include, but are not limited to, an increased rate of lysis; an increased size of plaque formation; an increased rate of RNA replication; an increased rate of RNA transcription; an increased rate of translation; an increased rate of virus assembly and/or packaging; an increased number of viral progeny; an increased ability of a reovirus to be taken up by a host cell; an increased or enhanced ability to uncoat; enhanced cell lysis or inducement to cell death including apoptosis, necrosis or autophagy; an enhanced ability to infect, lyse and kill human neoplastic cells lines; decreased immunogenicity in mammalian cells; differential susceptibility to interferon sensitivity; decreased toxicity toward the host; enhanced drug interaction; enhanced radiotherapy interaction; or the ability to release effective tumor epitopes.

A reovirus as described herein can be included, along with a pharmaceutically acceptable carrier, in a pharmaceutical composition. Such pharmaceutical compositions can include, for example, one or more chemotherapeutic agents and/or one or more immunosuppressive agents.

In still another aspect, the invention provides for methods of making an improved reovirus. Such methods generally include the steps of modifying the nucleic acid sequence of the reovirus, and selecting one or more improved reoviruses. In some embodiments, the modifying step includes, for example, mutagenizing the reovirus. Representative types of mutagenesis include, without limitation, site-directed mutagenesis and chemical mutagenesis. In other embodiments, the modifying step includes culturing the reovirus in a human cell line.

An improved reovirus made according to the methods disclosed herein can be selected for an increased rate of lysis; an increased size of plaque formation; an increased rate of RNA replication; an increased rate of RNA transcription; an increased rate of translation; an increased rate of virus assembly and/or packaging; an increased number of viral progeny; an increased ability of a reovirus to be taken up by a host cell; an increased or enhanced ability to uncoat; enhanced cell lysis or inducement to cell death including apoptosis, necrosis or autophagy; an enhanced ability to infect, lyse and kill human neoplastic cells lines; decreased immunogenicity in mammalian cells; differential susceptibility to interferon sensitivity; decreased toxicity toward the host; enhanced drug interaction; enhanced radiotherapy interaction; or the ability to release effective tumor epitopes.

In yet another aspect, the invention provides methods of treating a proliferative disorder in a patient. Such methods generally include administering a modified reovirus as described herein or a pharmaceutical composition containing such a modified reovirus to the patient. Typically, the reovirus is administered in an amount effective to cause oncolysis, and can be administered more than once. Representative routes of administration include, for example, direct injection, intravenously, intravascularly, intrathecally, intramuscularly, subcutaneously, intraperitoneally, topically, orally, rectally, vaginally, nasally, or by inhalation. The methods of treating a proliferative disorder as described herein can be accompanied by one or more procedures such as surgery, chemotherapy, radiation therapy, and immunosuppressive therapy.

In another aspect, the invention provides a kit (or article of manufacture) that includes a reovirus having a modified sequence or any combination of genome segments having a modified sequence as disclosed herein. A kit also can include one or more agents as disclosed herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 1 is the nucleotide sequence of a representative S1 segment (SEQ ID NO:1), S2 segment (SEQ ID NO:2), S3 segment (SEQ ID NO:3) and S4 segment (SEQ ID NO:4).

FIG. 2 is the nucleotide sequence of a representative M1 segment (SEQ ID NO:5), M2 segment (SEQ ID NO:6) and M3 segment (SEQ ID NO:7).

FIG. 3 is the nucleotide sequence of a representative L1 segment (SEQ ID NO:8), L2 segment (SEQ ID NO:9) and L3 segment (SEQ ID NO:10).

FIG. 4 is the amino acid sequence of a representative sigma-1 polypeptide (SEQ ID NO:11), sigma-2 polypeptide (SEQ ID NO:12), sigma-NS polypeptide (putative coding sequence 1, SEQ ID NO:13; putative coding sequence 2, SEQ ID NO:14) and sigma-3 polypeptide (SEQ ID NO:15).

FIG. 5 is the amino acid sequence of a representative mu-2 polypeptide (SEQ ID NO:16), mu-1 polypeptide (SEQ ID NO:17) and mu-NS polypeptide (SEQ ID NO:18).

FIG. 6 is the amino acid sequence of a representative lambda-3 polypeptide (SEQ ID NO:19), lambda-2 polypeptide (SEQ ID NO:20) and lambda-1 polypeptide (SEQ ID NO:21).

Like reference symbols in the various drawings indicate like elements.

DETAILED DESCRIPTION

This disclosure describes modifications in the nucleotide and amino acid sequence of a reovirus. Such modifications are optionally selected to affect the virus's ability to replicate and/or package itself and, therefore, alter the infectivity and/or rate of replication of a reovirus.

Reovirus Having Modified Sequences and Methods of Making

Any of the genomic segments from any type 3 mammalian orthoreovirus (referred to herein simply as "reovirus") can be modified as disclosed herein. Representative type 3 mammalian orthoreoviruses include, without limitation, Dearing and Abney strains. See, for example, ATCC Accession Nos. VR-232 and VR-824. Reoviruses that can be modified as disclosed herein include naturally-occurring reoviruses (e.g., isolated from a source in nature such as from a patient) and reassortant reoviruses (see, e.g., U.S. Pat. No. 7,163,678).

Representative modifications to the different genomic segments of a reovirus and their manifestations in the encoded polypeptide are shown in Table 1. The modifications shown in Table 1 show modifications (both in the number of modifications and in the non-conservative nature of many of the modifications) in the sequence of segments encoding polypeptides associated with RNA-dependent RNA polymerase, transcriptional activities and/or RNA binding. For example, many of the novel modifications disclosed herein are located in the L1 genome segment. The wild-type L1 genome segment encodes a 1,267 amino acid (142 kDa) protein designated lambda-3. Lambda-3 represents the catalytic subunit of the reovirus RNA-dependent RNA polymerase, which mediates both plus- and minus-strand RNA synthesis within reovirus particles. Further modifications were observed in the M2 genome segment. The wild-type M2 genome segment encodes a 708 amino acid (76 kDa) protein designated mu-1, which is involved in the regulation of particle-bound transcription. In addition, modifications also were observed in the S4 and M1 genomic segments, which encode sigma-3 and mu-2, respectively, and play a role in transcription or single-stranded or double-stranded RNA binding.

Thus, this disclosure provides for L1, S4, M1, M2 or any combination of such genome segments that contain one or more nucleic acid modifications in the respective genome segment. Provided herein is a reovirus L1 genome segment having one or more nucleic acid modifications; a reovirus S4 genome segment having one or more nucleic acid modifications; a reovirus M1 genome segment having one or more nucleic acid modifications; and/or a M2 genome segment having one or more nucleic acid modifications.

A reovirus L1 genome segment has, for example, any combination of one or more of the following nucleotides: a T at position 660, a G at position 817, an A at position 1687, a G at position 2283, an ATG at positions 2284-2286, a C at position 2794, a C at position 2905, a C at position 2953, an A at position 3153, or a G at position 3231 (numbered relative to GenBank Accession No. M24734.1). A reovirus S4 genome segment has, for example, any combination of one or more of the following nucleotides: an A at position 74 or an A at position 624 (numbered relative to GenBank Accession No. K02739). A reovirus M1 genome segment has, for example, a T nucleotide at position 1595 (numbered relative to GenBank Accession No. AF461684.1). A reovirus M2 genome segment has, for example, a C nucleotide at position 248 (numbered relative to GenBank Accession No. M20161.1). The indicated nucleotide at the indicated position represents modifications when compared to other corresponding sequences available in public databases (e.g., GenBank Accession Nos. M24734.1, K02739, AF461684.1, and M20161.1).

A reovirus lambda-3 polypeptide has, for example, any combination of one or more amino acid residues: a Val at residue 214, an Ala at residue 267, a Thr at residue 557, a Lys at residue 755, a Met at residue 756, a Pro at residue 926, a Pro at residue 963, a Leu at residue 979, an Arg at residue 1045, or a Val at residue 1071 (numbered relative to GenBank Accession No. M24734.1). It is noted that, when the polypeptide sequence comprises a Val at residue 214 or a Val at residue 1071, the polypeptide sequence further comprises at least one additional change in the amino acid sequence. A reovirus sigma-3 polypeptide has, for example, any combination of one or more amino acid residues: a Leu at residue 14 or a Lys at residue 198 (numbered relative to GenBank Accession No. K02739). It is noted that, when the polypeptide sequence comprises a Leu at residue 14, the polypeptide sequence further comprises at least one additional change in the amino acid sequence. A reovirus mu-1 polypeptide has, for example, an Asp at residue 73 (numbered relative to GenBank Accession No. AF461684.1). A reovirus mu-2 polypeptide has, for example, a Ser at residue 528 (numbered relative to GenBank Accession No. M20161.1). The indicated amino acid at the indicated position represents modifications when compared to other corresponding sequences in public databases (e.g., GenBank Accession Nos. M24734.1, K02739, AF461684.1, and M20161.1).

As used herein, a "non-naturally occurring" reovirus is a reovirus that has at least one nucleic acid or amino acid modification as compared to wild type sequences derived from, for example, a field isolate (e.g., a patient). "Non-naturally occurring" reovirus refers to a virus which has been manipulated or modified in the laboratory. Such manipulated or modified reoviruses include laboratory strains or mutagenized versions. These versions are distinguishable, in nucleic acid and/or amino acid sequence, from, for example, Dearing and Abney strains (e.g., ATCC VR-824 and VF-232, respectively). Representative modifications to one or more of the genome segments, the encoded polypeptide, or both are disclosed herein. In addition to a genome segment or polypeptide containing one or more of the modifications described herein, a reovirus optionally contains an S2 genome segment, which encodes the sigma-2 polypeptide. A sigma-2 polypeptide, for example, has a Cys at one or more or all of the following positions: 70, 127, 195, 241, 255, 294, 296 or 340 (numbered relative to GenBank Accession No. NP_694684.1).

A modification generally occurs at the nucleic acid level, which may or may not manifest itself in the encoded polypeptide. Modifications to a nucleic acid include, without limitation, single or multiple nucleotide transitions (purine to purine or pyrimidine to pyrimidine) or transversions (purine to pyrimidine or vice versa) and single- or multiple-nucleotide deletions or insertions. A modification in a nucleic acid can result in one or more conservative or non-conservative amino acid substitutions in the encoded polypeptide, a shift in the reading frame of translation ("frame-shift) resulting in an entirely different polypeptide encoded from that point on, a premature stop codon resulting in a truncated polypeptide ("truncation"), or a modification in a reovirus nucleic acid may not change the encoded polypeptide at all ("silent" or "nonsense"). See, for example, Johnson & Overington, 1993, *J. Mol. Biol.*, 233:716-38; Henikoff & Henikoff, 1992, *Proc. Natl. Acad. Sci. USA*, 89:10915-19; and U.S. Pat. No. 4,554, 101 for disclosure on conservative and non-conservative amino acid substitutions.

Nucleic acids from reovirus particles are isolated, for example, using standard methodologies, which are commercially available. See also, for example, Schiff et al., "Orthoreoviruses and Their Replication," Ch 52, in *Fields Virology*, Knipe & Howley, eds., 2006, Lippincott Williams & Wilkins. As used herein, "isolated" nucleic acids refer to nucleic acids that are substantially separated from other nucleic acids with which they are usually associated. Thus, an "isolated" nucleic acid includes, without limitation, reoviral nucleic acid that is essentially free of non-reoviral (e.g., host cell) nucleic acid, or a reoviral genomic segment that is essentially free of nucleic acid corresponding to other genomic segments. In addition, an isolated nucleic acid includes an engineered nucleic acid such as recombinant or synthetic nucleic acids.

Modifications are generated in the nucleic acid of a reovirus using any number of methods known in the art. For example, site directed mutagenesis can be used to modify a reovirus nucleic acid sequence. One of the most common methods of site-directed mutagenesis is oligonucleotide-directed mutagenesis. In oligonucleotide-directed mutagenesis, an oligonucleotide encoding the desired change(s) in sequence is annealed to one strand of the DNA of interest and serves as a primer for initiation of DNA synthesis. In this manner, the oligonucleotide containing the sequence change is incorporated into the newly synthesized strand. See, for example, Kunkel, 1985, *Proc. Natl. Acad. Sci. USA*, 82:488; Kunkel et al., 1987, *Meth. Enzymol.*, 154:367; Lewis & Thompson, 1990, *Nucl. Acids Res.*, 18:3439; Bohnsack, 1996, *Meth. Mol. Biol.*, 57:1; Deng & Nickoloff, 1992, *Anal. Biochem.*, 200:81; and Shimada, 1996, *Meth. Mol. Biol.*, 57:157.

Other methods are routinely used in the art to introduce a modification into a sequence. For example, modified nucleic acids are generated using PCR or chemical synthesis, or polypeptides having the desired change in amino acid sequence can be chemically synthesized. See, for example, Bang & Kent, 2005, *Proc. Natl. Acad. Sci. USA*, 102:5014-9 and references therein. Selection on a cell type on which reovirus is not usually grown (e.g., human cells) and/or chemical mutagenesis (see, for example, Rudd & Lemay, 2005, *J. Gen. Virology*, 86:1489-97) also can be used to generate modifications in the nucleic acid of a reovirus. For example, the modifications shown in Table 1 were generated by culturing reovirus on human cells (e.g., human embryonic kidney (HEK) 293 cells), which are not typically used in the art of culturing reovirus. In contrast, cells that are commonly used to culture reovirus are described in, for example, Tyler, "Mammalian Reoviruses," Ch 53, page 1731-2, in *Fields Virology*, Knipe & Howley, eds., 2006, Lippincott Williams & Wilkins. The modifications described herein represent an adaptation by the reovirus to human cells. There was also a selection step at each of these plaque purification steps by selection the largest plaque (triple plaque purification), thus a growth or virulence advantage in these cells.

After one or more modifications have been introduced into a reovirus nucleic acid or polypeptide, virus particles are reconstituted using methods known in the art. See, for example, Schiff et al., "Orthoreoviruses and Their Replication," Ch 52, in *Fields Virology*, Knipe & Howley, eds., 2006, Lippincott Williams & Wilkins; Smith et al., 1969, Virology, 39(4):791-810; and U.S. Pat. Nos. 7,186,542; 7,049,127; 6,808,916; and 6,528,305. Reoviruses having one or more modifications in their sequence are cultured in, for example, mouse L929 cells or neoplastic cells (e.g., MCF7 (ATCC Accession No. HTB-22), SKBR3 (ATCC Accession No. HTB-30), or MDA MB 468 (ATCC Accession No. HTB 132) cells), and selected based on any number of characteristics that may indicate, for example, a growth advantage over a reovirus that does not contain one or more modifications. Reoviruses are selected following culturing in a cell line (neoplastic or otherwise) and/or following infection of an animal model system.

Such characteristics include, without limitation, an increased rate of lysis; an increased size of plaque formation; an increased rate of RNA replication; an increased rate of RNA transcription; an increased rate of translation; an increased rate of virus assembly and/or packaging; an increased number of viral progeny; an increased ability of a reovirus to be taken up by a host cell; an increased or enhanced ability to uncoat; enhanced cell lysis or inducement to cell death including apoptosis, necrosis or autophagy; an enhanced ability to infect, lyse and kill human neoplastic cells lines; decreased immunogenicity in mammalian cells; differential susceptibility to interferon sensitivity; decreased toxicity toward the host; enhanced drug interaction; enhanced radiotherapy interaction; or the ability to release effective tumor epitopes. Additionally, reoviruses having a modified sequence are selected, for example, for the ability to lytically infect a mammalian cell having an active Ras pathway. See, for example, U.S. Pat. No. 7,052,832.

Reovirus particles are obtained using any number of methods known in the art. For example, reoviruses are cultured in L929 mouse fibroblast cells or human cells (e.g., HEK 293), and the viral particles purified using standard methodology. See, for example, Schiff et al., "Orthoreoviruses and Their Replication," Ch 52, in *Fields Virology*, Knipe & Howley, eds., 2006, Lippincott Williams & Wilkins; Smith et al., 1969, Virology, 39(4):791-810; and U.S. Pat. Nos. 7,186,542; 7,049,127; 6,808,916; and 6,528,305. As used herein, "purified" viral particles refers to virus particles that have been substantially separated from cellular components that naturally accompany it. Typically, virus particles are considered "purified" when they are at least 70% (e.g., at least 75%, 80%, 85%, 90%, 95%, or 99%) by dry weight, free from the proteins and other cellular components with which the viruses are naturally associated.

A reovirus having the nucleic acid sequence shown in FIGS. 1, 2 and 3 (SEQ ID NOs: 1-10) and the amino acid sequence shown in FIGS. 4, 5, and 6 (SEQ ID NOs:11-21), which contain the nucleotide and amino acid modifications shown in Table 1, was deposited with the International Depositary Authority of Canada (IDAC, National Microbiology Laboratory, Public Health Agency of Canada, 1015 Arlington St., Winnipeg, Manitoba Canada R3E 3R2) on Sep. 19, 2007, and assigned Accession No. 190907-01. This deposit will be maintained under the terms of the Budapest Treaty on the International Recognition of the Deposit of Microorganisms for the Purposes of Patent Procedure. This deposit is exemplary and was made merely as a convenience for those of skill in the art and is not an admission that a deposit is required for patentability (e.g., under 35 U.S.C. §112).

Methods of Using Reoviruses Having Modified Sequences

As described previously (see, for example, U.S. Pat. Nos. 6,110,461; 6,136,307; 6,261,555; 6,344,195; 6,576,234; and 6,811,775), reoviruses use a host cell's Ras pathway machinery to downregulate double-stranded RNA-activated protein kinase (PKR) and thus replicate in the cell. Based upon these discoveries, methods have been developed for using reovirus to treat proliferative disorders in mammals. Representative mammals include mice, dogs, cats, sheep, goats, cows, horses, pigs, non-human primates, and humans. As used herein, a "patient" includes any mammal with a proliferative disorder.

A "proliferative disorder" is any cellular disorder in which the cells proliferate more rapidly than normal tissue growth. Thus a "proliferating cell" is a cell that is proliferating more rapidly than normal cells. A proliferative disorder includes, but is not limited to, neoplasms, which are also referred to as tumors. A neoplasm includes, but is not limited to, pancreatic cancer, breast cancer, brain cancer (e.g., glioblastoma), lung cancer, prostate cancer, colorectal cancer, thyroid cancer, renal cancer, adrenal cancer, liver cancer, neurofibromatosis, and leukemia. A neoplasm includes a solid neoplasm (e.g. sarcoma or carcinoma) or a cancerous growth affecting the hematopoietic system (e.g., lymphoma or leukemia). Other proliferative disorders include, but are not limited to neurofibromatosis.

Generally, in proliferative disorders for which reovirus is used as a treatment, at least some of the proliferating cells have a mutation in which the Ras gene (or an element of the Ras signaling pathway) is activated, either directly (e.g., by an activating mutation in Ras) or indirectly (e.g., by activation of an upstream or downstream element in the Ras pathway). Activation of an upstream element in the Ras pathway includes, for example, transformation with epidermal growth factor receptor (EGFR) or Sos. See, for example, Wiessmuller & Wittinghofer, 1994, *Cellular Signaling*, 6(3): 247-267; and Barbacid, 1987, *Ann. Rev. Biochem.*, 56, 779-827. Activation of a downstream element in the Ras pathway includes, for example, a mutation within B-Raf. See, for example, Brose et al., 2002, *Cancer Res.*, 62:6997-7000. In addition, reovirus is useful for treating proliferative disorders caused by mutations or dysregulation of PKR. See, for example, Strong et al., 1998, *EMBO J.*, 17:3351-662.

A reovirus having a modified sequence as disclosed herein is administered to a mammal that has a proliferative disorder. As used herein, administration refers to delivery of a reovirus such that the reovirus contacts the proliferating cells. The route by which a reovirus is administered depends on the type of disorder and the location of the proliferating cells. A wide variety of administration routes can be employed. For example, for a solid neoplasm that is accessible, a reovirus is administered by direct injection. For a hematopoietic neoplasm, for example, a reovirus is administered intravenously or intravascularly. For certain neoplasms, e.g., those not easily accessible within the body such as metastases or brain tumors, a reovirus is administered in a manner such that it is transported systemically through the body of the mammal to thereby reach the neoplasm (e.g., intrathecally, intravenously, intramuscularly, subcutaneously, or intra-peritoneally). A reovirus also is administered locally including, for example, topically (e.g., for melanoma), orally (e.g., for oral or esophageal neoplasm), rectally (e.g., for colorectal neoplasm), vaginally (e.g., for cervical or vaginal neoplasm), nasally or by inhalation (e.g., for lung neoplasm). A reovirus is optionally administered by more than one route and/or to more than one location in an individual.

Targeted administration may be used to administer a reovirus. For example, dendritic cells containing a reovirus may be administered to a subject. See, for example, US Publication No. 2008/0014183. In another example of targeted delivery, carrier cells may be used to target cells of a proliferative disorder and prevent immune recognition of a reovirus which they carry. See, for example, Qiao et al., 2008, *Nature Med.*, 14:37-44; and WO 2008/009115.

A reovirus having a modified sequence as disclosed herein is administered in an amount that is sufficient to treat the proliferative disorder (e.g., an "effective amount"). A proliferative disorder is "treated" when administration of a reovirus having a modified sequence to proliferating cells affects one or more symptoms or clinical signs of the disorder including, e.g., increasing lysis (e.g., "oncolysis") of the cells, reducing the number of proliferating cells, reducing the size or progression of a neoplasm, reducing pain associated with the neoplasm, as compared to the signs or symptoms in the absence of the treatment. As used herein, the term "oncolysis" means at least 10% of the proliferating cells are lysed (e.g., at least 20%, 30%, 40%, 50%, or 75% of the cells are lysed). The percentage of lysis can be determined, for example, by measuring the reduction in the size of a neoplasm or in the number of proliferating cells in a mammal, or by measuring the amount of lysis of cells in vitro (e.g., from a biopsy of the proliferating cells).

An effective amount of a reovirus having a modified sequence is determined on an individual basis and is based, at least in part, on the particular reovirus used; the individual's size, age, gender; and the size and other characteristics of the proliferating cells. For example, for treatment of a human, approximately $10^3$ to $10^{12}$ plaque forming units (PFU) of a reovirus is used, depending on the type, size and number of proliferating cells or neoplasms present. The effective amount can be from about 1.0 PFU/kg body weight to about $10^{15}$ PFU/kg body weight (e.g., from about $10^2$ PFU/kg body weight to about $10^{13}$ PFU/kg body weight). A reovirus is administered in a single dose or in multiple doses (e.g., two, three, four, six, or more doses). Multiple doses are administered concurrently or consecutively (e.g., over a period of days or weeks). Treatment with a reovirus having a modified sequence lasts from several days to several months or until diminution of the disease is achieved.

It is contemplated that a reovirus having a modified sequence as disclosed herein is optionally administered in conjunction with surgery or removal of proliferating cells (e.g., a neoplasm). It also is contemplated that a reovirus having a modified sequence is optionally administered in conjunction with or in addition to radiation therapy. It is further contemplated that a reovirus having a modified sequence is optionally administered in conjunction with or in addition to known anticancer compounds, chemotherapeutic agents, and/or immunosuppressive agents. Such agents, include, but are not limited to, 5-fluorouracil, mitomycin C, methotrexate, hydroxyurea, gemcitabine, cyclophosphamide, dacarbazine, mitoxantrone, anthracycline (Epirubicin, Irinotecan, and Doxurubicin), antibodies to receptors such as herceptin, topoisomerase inhibitors such as etoposide or camptothecin, pregnasome, platinum compounds such as carboplatin and cisplatin, taxanes such as taxol and taxotere, hormone therapies such as tamoxifen and anti-estrogens, interleukins, interferons, aromatase inhibitors, progestational agents, LHRH analogs, mTOR inhibitors (e.g., rapamycin and derivatives thereof; see, for example, Homicsko et al., 2005, *Cancer Res.*, 65:6882-90; and Rao et al., 2004, *Curr. Cancer Drug Targets*, 4:621-35), and combinations thereof.

It is further contemplated that a reovirus having a modified sequence is administered in conjunction with an agent that can increase endothelial permeability and/or decrease interstitial fluid pressure. Such agents include, for example, TNF-α. See, for example, Sacchi et al., 2006, *Clin. Cancer Res.*, 12:175-182. It is contemplated that a reovirus having a modified sequence can be administered in conjunction with any combination of the therapies and agents described herein.

Pharmaceutical Compositions

Pharmaceutical compositions that include one or more reoviruses, at least one of which has a modified sequence as described herein, are provided. See, for example, U.S. Pat. No. 6,576,234. In addition to one or more reoviruses, at least one of which has a modified sequence, a pharmaceutical composition typically includes a pharmaceutically acceptable carrier. A pharmaceutically acceptable carrier includes a solid, semi-solid, or liquid material that acts as a vehicle, carrier or medium for the reovirus. Thus, for example, compositions containing a reovirus having a modified sequence are in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable carriers include phosphate-buffered saline or another physiologically acceptable buffer, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. A pharmaceutical composition additionally can include, without limitation, lubricating agents such as talc, magnesium stearate, and mineral oil; wetting agents; emulsifying and suspending agents; preserving agents such as methyl- and propylhydroxy-benzoates; sweetening agents; and flavoring agents. Pharmaceutical compositions of the invention can be formulated to provide quick, sustained or delayed release of a reovirus having a modified sequence after administration by employing procedures known in the art. In addition to the representative formulations described below, other suitable formulations for use in a pharmaceutical composition are found in *Remington: The Science and Practice of Pharmacy* (2003, Gennaro & Gennaro, eds., Lippincott Williams & Wilkens).

For preparing solid compositions such as tablets, a reovirus having a modified sequence is mixed with a pharmaceutical carrier to form a solid composition. Optionally, tablets or pills are coated or otherwise compounded to provide a dosage form affording the advantage of prolonged action. For example, a tablet or pill comprises an inner dosage and an outer dosage component, the latter being in the form of an envelope over the former. The two components, for example, are separated by an enteric layer which serves to resist disintegration in the stomach and permit the inner component to pass intact into the duodenum or to be delayed in release. A variety of materials are used for such enteric layers or coatings, such materials including a number of polymeric acids and mixtures of polymeric acids with such materials as shellac, cetyl alcohol, and cellulose acetate.

Liquid formulations that include a reovirus having a modified sequence for oral administration or for injection generally include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. These liquid or solid compositions optionally contain suitable pharmaceutically acceptable excipients as described herein. Such compositions are administered, for example, by the oral or nasal respiratory route for local or systemic effect. Compositions in pharmaceutically acceptable solvents are nebulized by use of inert gases. Nebulized solutions are inhaled, for example, directly from the nebulizing device, from an attached face mask tent, or from an intermittent positive pressure breathing machine. Solution, suspension, or powder compositions are administered, orally or nasally, for example, from devices which deliver the formulation in an appropriate manner.

Another formulation that is employed in the methods taught herein employs transdermal delivery devices ("patches"). Such transdermal patches are used to provide continuous or discontinuous infusion of a reovirus having a modified sequence. The construction and use of transdermal patches for the delivery of pharmaceutical agents are performed according to methods known in the art. See, for example, U.S. Pat. No. 5,023,252. Such patches are constructed for continuous, pulsatile, or on-demand delivery of a reovirus having a modified sequence.

A reovirus having a modified sequence is optionally chemically or biochemically pretreated (e.g., by treatment with a protease such as chymotrypsin or trypsin) prior to administration (e.g., prior to inclusion in the pharmaceutical composition). Pretreatment with a protease removes the outer coat or capsid of the virus and can be used to increase the infectivity of the virus. Additionally or alternatively, a reovirus having a modified sequence is coated in a liposome or micelle to reduce or prevent an immune response in a mammal that has developed immunity toward a reovirus. Such reoviruses are referred to as "immunoprotected reoviruses." See, for example, U.S. Pat. Nos. 6,565,831 and 7,014,847.

A reovirus having a modified sequence or a pharmaceutical composition comprising such a reovirus can be packaged into a kit. It is contemplated that a kit optionally includes one or more chemotherapeutic agents and/or immunosuppressive agents (e.g., anti-antireovirus antibodies). A pharmaceutical composition, for example, is formulated in a unit dosage form. The term "unit dosage forms" refers to physically discrete units suitable as unitary dosages for human subjects and other mammals, each unit containing a predetermined quantity of a reovirus having a modified sequence calculated to produce the desired therapeutic effect in association with a suitable pharmaceutically acceptable carrier.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the invention described in the claims.

EXAMPLES

Example 1

Sequencing and Analysis

Cultures for production of reovirus were initiated from a suspension-adapted HEK 293 S Master Cell Bank (MCB). HEK 293 cells were maintained in Serum Free Medium (HEK 293 SFM II) supplemented with L-glutamine. HEK 293 cells were expanded and seeded into three 15 L spinner flasks, and further expanded until there was 12 L in each of the three flasks. Infection of the HEK 293 cells by reovirus was performed by direct inoculation of the virus into the cell culture. The virus was harvested when the viability of the HEK 293 S cells had decreased by 20-50% post-infection. The virus material from all three spinners was pooled in a single sterile container and agitated to create a homogeneous mixture. Three liters of the pooled cell suspension was removed, transferred to conical tubes, and centrifuged at ~3000 rpm for 15 minutes. The cells were then resuspended with 100 mL of clarified conditioned medium, snap frozen in an alcohol-dry ice bath three times, and then filled into sterile, labeled cryovials for use as a seed stock.

A viral stock was prepared by performing a three-time plaque purification. Adherent HEK 293 S cells were plated onto 6-well tissue culture plates, infected with the seed stock described above, and two of the largest plaques were picked. These two plaques were separately amplified and harvested and two of the largest plaques were picked again. This procedure was repeated again for a total of three times. Of the two plaques, one was selected as seed stock for subsequent expansions.

Cultures were initiated from the same suspension adapted HEK 293 S MCB described above and were maintained in the same HEK 293 Serum Free Medium (HEK 293 SFM II) supplemented with L-glutamine. Cells were expanded from T-flasks up to multiple 3 L spinner flasks. The infection was performed by first diluting the plaque-purified virus in HEK 293 SFM media and then adding 8 to 12 mL of the diluted virus into the cell culture. The virus was harvested when the viability of the HEK 293 S cells had decreased by 20-50% following infection, and microscopic examination of each of the spinners confirmed the lack of microbial contamination and that a cytopathic effect (CPE) was present in the cells. CPE was indicated by cells having a swollen and granular appearance. The material from the spinners was pooled in a single sterile container, agitated to create a homogeneous mixture, and a bulk harvest sample removed. The remaining pooled cell suspension was transferred to conical tubes and centrifuged at ~3000 rpm for 15 minutes. The cells were then resuspended with 400 mL of clarified conditioned medium, and the concentrated cell suspension was snap-frozen in an alcohol-dry ice bath three times to lyse the cells and then filled into sterile, labeled cryovials for use in sequencing reactions.

Both RNA strands were sequenced from both directions, and the sequence of each of the 10 genomic segments was assembled from the overlapping contigs. The assembled sequence of each genomic segment was used in a BLAST search of the NCBI database the World Wide Web. Alignments with three or four different reovirus sequences found in the NCBI database were examined and the alignment having the highest amount of homology was used for further analysis. The polymorphisms or modifications compared to other reported sequences are shown in Table 1. Those modifications that are unique to the selected reovirus strain are indicated with an asterisk in Table 1.

TABLE 1

Modifications Identified

| Genomic Segment | Position (nucleotide; amino acid) | Published Sequence (nucleotide; amino acid) | Novel Polymorphism (nucleotide; amino acid) |
|---|---|---|---|
| S1 | | GenBank Accession No. M10262.1 | SEQ ID NO: 1 |
| | 499; 163 | A; Thr | T; Ser |
| S3 | | GenBank Accession No. X01627.1 | SEQ ID NO: 3 |
| | 1057; 344 | T; Leu | C; Leu |
| S4 | | GenBank Accesion No. K02739 | SEQ ID NO: 4 |
| * | 74; 14 | G; Leu | A; Leu |
| * | 624; 198 | G; Glu | A; Lys |
| | 719; 229 | G; Glu | T; Asp |
| M1 | | GenBank Accession No. AF461684.1 | SEQ ID NO: 5 |
| | 1129; 372 | G; Met | T; Ile |
| * | 1595; 528 | G; Ala | T; Ser |

TABLE 1-continued

Modifications Identified

| Genomic Segment | Position (nucleotide; amino acid) | Published Sequence (nucleotide; amino acid) | Novel Polymorphism (nucleotide; amino acid) |
|---|---|---|---|
| M2 | | GenBank Accession No. M20161.1 | SEQ ID NO: 6 |
| * | 248; 73 | A; Glu | C; Asp |
| | 302; 91 | G; Ala | C; Ala |
| | 303; 92 | C; Leu | T; Leu |
| | 305; 92 | T; Leu | G; Leu |
| | 709-10; 227 | CG; Thr | GC; Ser |
| | 1173; 382 | T; Leu | C; Leu |
| L1 | | GenBank Accession No. M24734.1 | SEQ ID NO: 8 |
| * | 660; 214 | A; Val | T; Val |
| * | 817; 267 | T; Ser | G; Ala |
| * | 1687; 557 | C; Pro | A; Thr |
| * | 2283; 755 | C; Asn | G; Lys |
| * | 2284-6; 756 | GAT; Asp | ATG; Met |
| * | 2794; 926 | A; Thr | C; Pro |
| * | 2905; 963 | T; Ser | C; Pro |
| * | 2953; 979 | A; Met | C; Leu |
| * | 3153; 1045 | C; Ser | A; Arg |
| * | 3231; 1071 | T; Val | G; Val |
| L2 | | GenBank Accession No. J03488.1 | SEQ ID NO: 9 |
| | 1838-40; 609 | TTT; Phe | GGG; Gly |
| | 3703; 1230 | A; Leu | G; Leu |
| L3 | | GenBank Accession No. AF129822 | SEQ ID NO: 10 |
| | 1512; 500 | T; Ile | G; Ser |
| | 2569; 852 | G; Gln | T; His |

* designates unique modifications; italicized residues indicate silent modifications; position numbers are with respect to the indicated GenBank Accession No.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular modification of a reovirus or treatment regime is disclosed and discussed and a number of modifications that can be made to the reovirus or regime are discussed, each and every combination and permutation of the reovirus and the regime are specifically contemplated unless specifically indicated to the contrary. Likewise, any subset or combination of these is also specifically contemplated and disclosed.

What is claimed is:

1. An isolated reovirus comprising a lambda-3 polypeptide, wherein the lambda-3 polypeptide comprises SEQ ID NO:19.

2. An isolated reovirus, said reovirus having IDAC Accession No. 190907-01.

3. An isolated polypeptide comprising the amino acid sequence of SEQ ID NO:19.

4. A pharmaceutical composition comprising the isolated reovirus of claim 1 and a pharmaceutically acceptable carrier.

5. The pharmaceutical composition of claim 4, further comprising one or more chemotherapeutic agents and/or one or more immunosuppressive agents.

6. A kit comprising the isolated reovirus of claim 1.

7. The kit of claim 6, further comprising one or more chemotherapeutic agents and/or one or more immunosuppressive agents.

8. A kit comprising the pharmaceutical composition of claim 4.

9. The kit of claim 8, further comprising one or more chemotherapeutic agents and/or one or more immunosuppressive agents.

10. A kit comprising the isolated reovirus of claim 2.

11. The kit of claim 10, further comprising one or more chemotherapeutic agents and/or one or more immunosuppressive agents.

12. A pharmaceutical composition comprising the isolated reovirus of claim 1 and a pharmaceutically acceptable carrier.

13. The pharmaceutical composition of claim 12, further comprising one or more chemotherapeutic agents and/or one or more immunosuppressive agents.

* * * * *

UNITED STATES PATENT AND TRADEMARK OFFICE
CERTIFICATE OF CORRECTION

PATENT NO.      : 7,803,385 B2                        Page 1 of 1
APPLICATION NO. : 12/046095
DATED           : September 28, 2010
INVENTOR(S)     : Matthew C. Coffey It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 122 days.

Signed and Sealed this
Twenty-eighth Day of August, 2012

David J. Kappos
*Director of the United States Patent and Trademark Office*

SEQUENCE LISTING

<160> NUMBER OF SEQ ID NOS: 30

<210> SEQ ID NO 1
<211> LENGTH: 1416

-continued

<212> TYPE: DNA
<213> ORGANISM: Reovirus

<400> SEQUENCE: 1

```
gctattggtc ggatggatcc tcgcctacgt gaagaagtag tacggctgat aatcgcatta      60
acgagtgata atggagcatc actgtcaaaa gggcttgaat caagggtctc ggcgctcgag     120
aagacgtctc aaatacactc tgatactatc ctccggatca cccagggact cgatgatgca     180
aacaaacgaa tcatcgctct tgagcaaagt cgggatgact tggttgcatc agtcagtgat     240
gctcaacttg caatctccag attggaaagc tctatcggag ccctccaaac agttgtcaat     300
ggacttgatt cgagtgttac ccagttgggt gctcgagtgg acaacttga  dacaggactt     360
gcagagctac gcgttgatca cgacaatctc gttgcgagag tggatactgc agaacgtaac     420
attggatcat tgaccactga gctatcaact ctgacgttac gagtaacatc catacaagcg     480
gatttcgaat ctaggatatc cacgttagag cgcacggcgg tcactagcgc gggagctccc     540
ctctcaatcc gtaataaccg tatgaccatg ggattaaatg atggactcac gttgtcaggg     600
aataatctcg ccatccgatt gccaggaaat acgggtctga atattcaaaa tggtggactt     660
cagtttcgat ttaatactga tcaattccag atagttaata ataacttgac tctcaagacg     720
actgtgtttg attctatcaa ctcaaggata ggcgcaactg agcaaagtta cgtggcgtcg     780
gcagtgactc ccttgagatt aaacagtagc acgaaggtgc tggatatgct aatagacagt     840
tcaacacttg aaattaattc tagtggacag ctaactgtta gatcgacatc cccgaatttg     900
aggtatccga tagctgatgt tagcggcggt atcggaatga gtccaaatta taggtttagg     960
cagagcatgt ggataggaat tgtctcctat tctggtagtg ggctgaattg gagggtacag    1020
gtgaactccg acatttttat tgtagatgat tacatacata tatgtcttcc agcttttgac    1080
ggtttctcta tagctgacgg tggagatcta tcgttgaact tgttaccgg attgttacca     1140
ccgttactta caggagacac tgagcccgct tttcataatg acgtggtcac atatggagca    1200
cagactgtag ctatagggtt gtcgtcgggt ggtgcgcctc agtatatgag taagaatctg    1260
tgggtggagc agtggcagga tggagtactt cggttacgtg ttgagggggg tggctcaatt    1320
acgcactcaa acagtaagtg gcctgccatg accgtttcgt acccgcgtag tttcacgtga    1380
ggatcagacc accccgcggc actggggcat ttcatc                              1416
```

<210> SEQ ID NO 2
<211> LENGTH: 1331
<212> TYPE: DNA
<213> ORGANISM: Reovirus

<400> SEQUENCE: 2

```
gctattcgct ggtcagttat ggctcgcgct gcgttcctat tcaagactgt tgggtttggt      60
ggtctgcaaa atgtgccaat taacgacgaa ctatcttcac atctactccg agctggtaat     120
tcaccatggc agttaacaca gttttttagac tggataagcc ttgggagggg tttagctaca     180
tcggctctcg ttccgacggc tgggtcaaga tactatcaaa tgagttgcct tctaagtggc     240
actctccaga ttccgttccg tcctaaccac cgatggggag acattaggtt cttacgctta     300
gtgtggtcag ctcctactct cgatggatta gtcgtagctc caccacaagt tttggctcag     360
cccgctttgc aagcacaggc agatcgagtg tacgactgcg atgattatcc atttctagcg     420
cgtgatccaa gattcaaaca tcgggtgtat cagcaattga gtgctgtaac tctacttaac     480
ttgacaggtt ttggcccgat ttcctacgtt cgagtggatg aagatatgtg gagtggagat     540
```

-continued

```
gtgaaccagc ttctcatgaa ctatttcggg cacacgtttg cagagattgc atacacattg    600
tgtcaagcct cggctaatag gccttgggaa tatgacggta catatgctag gatgactcag    660
attgtgttat ccttgttctg ctatcgtat gtcggtgtaa ttcatcagca gaatacgtat    720
cggacattct attttcagtg taatcggcga ggtgacgccg ctgaggtgtg gattctttct    780
tgttcgttga accattccgc acaaattaga ccgggtaatc gtagcttatt cgttatgcca    840
actagcccag attggaacat ggacgtcaat ttgatcctga gttcaacgtt gacggggtgt    900
ttgtgttcgg gttcacagct gccactgatt gacaataatt cagtacctgc agtgtcgcgt    960
aacatccatg gctggactgg tagagctggt aaccaattgc atgggttcca ggtgagacga   1020
atggtgactg aattttgtga caggttgaga cgcgatggtg tcatgaccca agctcagcag   1080
aatcaagttg aagcgttggc agatcagact caacagttta agaggacaa gctcgaaacg   1140 tgggcgagag aagacgatca atataatcag gctcatccca actccacaat gttccgtacg   1200
aaaccattta cgaatgcgca atggggacga ggtaatacgg gggcgactag tgccgcgatt   1260
gcagccctta tctgatcgtc ttggagtgag ggggtccccc cacacacctc acgactgacc   1320
acacattcat c                                                        1331
```

<210> SEQ ID NO 3
<211> LENGTH: 1198
<212> TYPE: DNA
<213> ORGANISM: Reovirus

<400> SEQUENCE: 3

```
gctaaagtca cgcctgtcgt cgtcactatg gcttcctcac tcagagctgc gatctccaag     60
atcaagaggg atgacgtcgg tcagcaagtt tgtcctaatt atgtcatgct gcggtcctct    120
gtcacaacaa aggtggtacg aaatgtggtt gagtatcaaa ttcgtacggg cggattcttt    180
tcgtgcttag ctatgctaag gccactccag tacgctaagc gtgagcgttt gcttggtcag    240
aggaatctgg aacgtatatc gactagggat atccttcaga ctcgtgattt acactcacta    300
tgtatgccaa ctcctgatgc gccaatgtct aatcatcaag catccaccat gagagagctg    360
atttgcagtt acttcaaggt cgatcatgcg gatgggttga atatatacc catggatgag    420 agatactctc cgtcatcact tgccagattg tttaccatgg gcatggctgg gctgcacatt    480
accactgagc atcttataa gcgtgttccg attatgcact agctgcgga cttggactgt    540 atgacgctgg ctctacctta catgattacg cttgatggtg atactgtggt tcctgtcgct    600
ccaacactgt cagcggaaca gcttctggac gacggactca aaggattagc atgcatggat    660
atctcctatg gatgtgaggt ggacgcgaat agccggccgg ctggtgatca gagtatggac    720
tcttcacgct gcatcaacga gttgtattgc gaggagacag cagaagccat ctgtgtgctt    780
aagacatgcc ttgtgttaaa ttgcatgcag tttaaacttg agatggatga cctagcacat    840
aacgctgcta agctggacaa gatacagatg atgatacccct tcagtgagcg tgtttttagg    900
atggcctcgt cctttgcgac tattgatgcc cagtgtttta ggttttgcgt gatgatgaag    960
gataaaaatc tgaaaataga tatgcgtgaa acgacgagac tgtggactcg ttcagcatca   1020
gatgattctg tggccacgtc atctttaagt atttccctgg accggggtcg atgggtggcg   1080
gctgacgcca gtgatgctag actgctggtt tttccgattc gcgtgtaatg ggtgagtgag   1140
ctgatgtggt cgccaagaca tgtgccggtg tcttggtggt gggtgacgcc taatcatc    1198
```

<210> SEQ ID NO 4
<211> LENGTH: 1196

<212> TYPE: DNA
<213> ORGANISM: Reovirus

<400> SEQUENCE: 4

```
gctattttg cctcttccca gacgttgtcg caatggaggt gtgcttgccc aacggtcatc    60
aggtcgtgga cttaattaac aacgcttttg aaggtcgtgt atcaatctac agcgcgcaag   120
agggatggga caaaacaatc tcagcacagc cagatatgat ggtatgtggt ggcgccgtcg   180
tttgcatgca ttgtctaggt gttgttggat ctctacaacg caagctgaag catttgcctc   240
accatagatg taatcaacag atccgtcatc aggattacgc cgatgtacag ttcgcagacc   300
gtgttactgc tcactggaag cggggtatgc tgtccttcgt tgcgcagatg cacgagatga   360
tgaatgacgt gtcgccagat gacctggatc gtgtgcgtac tgagggaggt tcactagtgg   420
agctgaaccg gcttcaggtt gacccaaatt caatgtttag atcaatacac tcaagttgga   480
cagatccttt gcaggtggtg gacgaccttg cactaagct ggatcagtac tggacagcct   540
taaacctgat gatcgactca tccgacttga tacccaactt tatgatgaga gacccatcac   600
acgcgttcaa tggtgtgaaa ctgaagggag atgctcgtca acccaattc tccaggactt   660
ttgattcgag atcgagtttg gaatggggtg tgatggttta tgattactct gagctggatc   720
atgatccatc gaagggccgt gcttacagaa aggaattggt gacgccagct cgagatttcg   780
gtcactttgg attatcccat tattctaggg cgactacccc aatccttgga aagatgccgg   840
ccgtattctc aggaatgttg actgggaact gtaaaatgta tccattcatt aaaggaacgg   900
ctaagctgaa gacagtgcgc aagctagtgg aagcagtcaa tcatgcttgg ggtgtcgaga   960
agattagata tgctcttggg ccaggtggca tgacgggatg gtacaatagg actatgcaac  1020
aggccccat tgtgctaact cctgctgctc tcacaatgtt cccagatacc atcaagtttg  1080
gggatttgaa ttatccagtg atgattggcg atccgatgat tcttggctaa cacccccat  1140
cttcacagcg ccgggcttga ccaacctggt gtgacgtggg acaggcttca ttcatc      1196
```

<210> SEQ ID NO 5
<211> LENGTH: 2304
<212> TYPE: DNA
<213> ORGANISM: Reovirus

<400> SEQUENCE: 5

```
gctattcgcg gtcatggctt acatcgcagt tcctgcggtg gtggattcac gttcgagtga    60
ggctattgga ctgctagaat cgtttggagt agacgctggg gctgacgcga atgacgtttc   120
atatcaagat catgactatg tgttggatca gttacagtac atgttagatg gatatgaggc   180
tggtgacgtt atcgatgcac tcgtccacaa gaattggtta catcactctg tctattgctt   240
gttgccaccc aaaagtcaac tattagagta ttggaaaagt aatccttcag cgataccgga   300
caacgttgat cgtcggcttc gtaaacgact aatgctaaag aaagatctca ggaaagatga   360
tgaatacaat cagctagcgc gtgctttcaa gatatcggat gtctacgcac ctctcatctc   420
atccacgacg tcaccgatga caatgataca gaacttgaat cgaggcgaga tcgtgtacac   480
cacgacggac agggtaatag gggctagaat cttgttatat gctcctagaa agtactatgc   540
gtcaactctg tcatttacta tgactaagtg catcattccg tttggtaaag aggtgggtcg   600
tgttcctcac tctcgattta atgttggcac atttccgtca attgctaccc cgaaatgttt   660
tgtcatgagt ggggttgata ttgagtccat cccaaatgaa tttatcaagt tgttttacca   720
gcgcgtcaag agtgttcacg ctaacatact aaatgacata tctcctcaga tcgtctctga   780
```

-continued

| | |
|---|---|
| catgataaac agaaagcgtc tgcgcgttca tactccatca gatcgtcgag ccgcgcagtt | 840 |
| gatgcatttg ccttaccatg ttaaacgagg agcgtctcac gtcgacgttt acaaggtgga | 900 |
| tgttgtagac atgttgttcg aggtagtgga tgtggccgat gggttgcgca acgtatctag | 960 |
| gaaactaact atgcataccg ttcctgtatg tattcttgaa atgttgggta ttgagattgc | 1020 |
| ggactattgc attcgtcaag aggatggaat gctcacagat tggttcctac ttttaaccat | 1080 |
| gctatctgat ggcttgactg atagaaggac gcattgtcaa tacttgatta atccgtcaag | 1140 |
| tgtgcctcct gatgtgatac ttaacatctc aattactgga tttataaata gacatacaat | 1200 |
| cgatgtcatg cctgacatat atgacttcgt taaacccatt ggcgctgtgc tgcctaaggg | 1260 |
| atcatttaaa tcaacaatta tgagagttct tgattcaata tcaatattag gaatccaaat | 1320 |
| catgccgcgc gcgcatgtag ttgactcaga tgaggtgggc gagcaaatgg agcctacgtt | 1380 |
| tgagcaggcg gttatggaga tatacaaagg gattgctggc gttgactcgc tggatgatct | 1440 |
| catcaagtgg gtgttgaact cggatctcat tccgcatgat gacaggcttg gtcaattatt | 1500 |
| tcaagcgttt ttgcctctcg caaaggactt attagctcca atggccagaa agttttatga | 1560 |
| taactcaatg agtgagggta gattgctaac attctctcat gccgacagtg agttgctgaa | 1620 |
| cgcaaattat tttggtcatt tattgcgact aaaaatacca tatattacag aggttaatct | 1680 |
| gatgattcgc aagaatcgtg agggtggaga gctatttcag cttgtgttat cttatctata | 1740 |
| taaaatgtat gctactagcg cgcagcctaa atggtttgga tcattattgc gattgttaat | 1800 |
| atgtccctgg ttacatatgg agaaattaat aggagaagca gacccggcat ctacgtcggc | 1860 |
| tgaaatttgg tggcatatcc ctcgtgaaca gctgatgcaa gatggatggt gtggatgtga | 1920 |
| agacggattc attccctatg ttagcatacg tgcgccaaga ctggttatag aggagttgat | 1980 |
| ggagaagaac tggggccaat atcatgccca agttattgtc actgatcagc ttgtcgtagg | 2040 |
| cgaaccgcgg agggtatctg ctaaggctgt gatcaagggt aaccacttac cagttaagtt | 2100 |
| agtttcacga tttgcatgtt tcacattgac ggcgaagtat gagatgaggc tttcgtgcgg | 2160 |
| ccatagcact ggacgtggag ctgcatacag tgcgagacta gctttccgat ctgacttggc | 2220 |
| gtgatccgtg acatgcgtag tgtgacacct gctcctaggt caatgggggt aggggcggg | 2280 |
| ctaagactac gtacgcgctt catc | 2304 |

<210> SEQ ID NO 6
<211> LENGTH: 2204
<212> TYPE: DNA
<213> ORGANISM: Reovirus

<400> SEQUENCE: 6

| | |
|---|---|
| ggctaatctg ctgaccgtta ctctgcaaag atggggaacg cttcctctat cgttcagacg | 60 |
| atcaacgtca ctggagatgg caatgtattt aaaccatcag ctgaaacttc atctaccgct | 120 |
| gtaccatcgt taagcttatc acctggaatg ctgaatcccg gaggggtacc atggattgct | 180 |
| gttggagatg agacatctgt gacttcacca ggcgcattac gtcgaatgac gtcaaaggac | 240 |
| atcccggaca cggcaataat caacacagac aattcatcag gcgccgtgcc aagcgaatca | 300 |
| gccttggtgc cctacatcga tgagccgctg gtagtggtta cagagcatgc tattaccaac | 360 |
| ttcaccaaag ctgagatggc acttgaattc aatcgtgagt tccttgacaa gatgcgtgtg | 420 |
| ctgtcagtgt caccaaaata ttcggatctt ctgacctatg ttgactgcta cgtcggtgtg | 480 |
| tctgctcgtc aggcttttaaa caattttcag aaacaagtgc ctgtgattac acctactagg | 540 |
| cagacgatgt atgtcgactc gatacaagcg gccttgaaag cttagaaaa gtgggagatt | 600 |

```
gatctgagag tggctcaaac gttgctgcct acgaacgttc cgattggaga agtctcttgt      660
ccaatgcagt cggtagtgaa actgctggat gatcagctgc cagatgacag cctgatacgg      720
aggtatccca aggaagccgc cgtcgctttg gctaaacgaa acgggggaat acaatggatg      780
gacgtatcag aaggcaccgt gatgaacgag gctgtcaacg ctgttgcagc tagtgcactg      840
gcaccttcag catcagcccc acccttagaa gagaagtcaa agttaaccga caagcgatg       900 gatctcgtga ccgcggctga gcctgagata attgcctcac tcgcgccagt tcccgcaccc      960
gtgtttgcca taccacctaa accagcagat tataatgtgc gtactctgag gatcgacgag     1020
gccacttggc tgcgaatgat tccaaaatca atgaacacac ctttcaaat ccaggtgact      1080 gataacacag gaactaattg gcatctcaat ttgaggggg ggactcgtgt agtgaatctg      1140
gaccaaatcg ctccgatgcg gtttgtatta gatctagggg gaaagagtta taagagacg      1200 agctgggatc caaacggcaa gaaggtcgga ttcatcgttt ttcaatcgaa gataccattc     1260
gaactttgga ctgctgcttc acagatcggt caagccacgg tggttaacta tgtccaacta     1320
tacgctgaag acagctcatt taccgcgcag tctatcattg ctactacctc tttggcttat     1380
aactatgagc ctgagcagtt gaataagact gaccctgaga tgaattatta tcttttggcg     1440 accttatag actcagccgc tataacgcca acgaatatga cacagcctga tgtttgggat      1500
gccttgctga cgatgtcccc actatcagct ggcgaggtga cagtgaaggg tgcggtagtg     1560
agtgaagtag tccctgcaga cttgataggt agctacactc cagaatccct aaacgcctca     1620
cttccgaatg atgctgctag atgcatgatc gatagagctt cgaagatagc cgaagcaatc     1680
aagattgatg atgatgctgg accagatgaa tattcccca actctgtacc aattcaaggt      1740
cagcttgcta tctcgcaact cgaaactgga tatggtgtgc gaatattcaa ccctaaaggg     1800 atccttttcta aaattgcatc tagggcaatg caggctttca ttggtgaccc gagcacaatc     1860
atcacgcagg cggcgccagt gttatcagac aagaataatt ggattgcatt ggcacaggga     1920
gtgaaaacta gtctgcgtac taaaagtcta tcagcgggag tgaagactgc agtgagtaag     1980
ctgagctcat ctgagtctat ccagaattgg actcaaggat tcttggataa agtgtcagcg     2040
cattttccag caccaaagcc cgattgtccg actagcggag atagtggtga atcgtctaat     2100
cgccgagtga agcgcgactc atacgcagga gtggtcaaac gtgggtacac acgttaggcc     2160
gctcgccctg gtgacgcggg gttaagggat gcaggcaaat catc                      2204

<210> SEQ ID NO 7
<211> LENGTH: 2241
<212> TYPE: DNA
<213> ORGANISM: Reovirus

<400> SEQUENCE: 7
gctaaagtga ccgtggtcat ggcttcattc aagggattct ccgccaacac tgttccagtt      60
tctaaggcca agcgtgacat atcatctctt gccgctactc ctggacttcg ttcacaatcc     120
ttcactccgt ctgtggatat gtctcaatcg cgtgaattcc tcacaaaggc aattgagcaa     180
gggtccatgt ctataccta tcagcatgtg aatgtaccga aagttgatcg taaagttgtt     240
agcctggtag tgcgacccct ctcttccaggt gctttctcta tctctggagt gatttcgcca     300
gcccatgcct atctactaga gtgtctaccc cagcttgagc aggcgatggc ttttgttgct     360
tcacctgagt ctttccaggc ttccgacgtc gcgaagcgct ttgccataaa gccaggtatg     420
agcctccagg atgccatcac tgcctttatt aactttgtgt ccgcgatgct gaaaatgacg     480
```

-continued

```
gtgactcgtc aaaactttga cgttattgtg gctgagatcg agaggcttgc ttcaaccagc        540
gtgtccgtca ggactgaaga agcgaaggtt gctgatgagg agctaatgct attcgggtta        600
gatcatagag ggccacagca gctggatgtt tctgacgcta aagggataat gaaggctgct        660
gatattcaga caactcatga tgtccatttg gcaccaggcg ttggtaatat tgatcctgaa        720
atctataacg aggggcggtt catgttcatg cagcacaagc cacttgcggc ggatcaatcg        780
tatttcacct tggagactgc ggattattte aagatttatc caacatacga tgaacatgat        840
ggcaggatgg ctgaccaaaa gcagtcggga ttgatactgt gtactaagga cgaggtattg        900
gctgagcaaa ctatatttaa actggacgcc cctgatgaca agactgttca tctgttggat        960
cgcgatgacg accacgttgt tgccagattt actaaggtat ttatagagga cgtggctccc       1020
gggcatcatg ctgctcaaag atcgggacaa cgctctgtgc ttgatgacct atatgcgaat       1080
acgcaagtga tttccattac ttctgctgct ttaaagtggg tggtcaagca cggcgtatct       1140 gatgaatcg tgaacaggaa gaatgtcaaa gtgtgtgttg gttttgaccc cctgtacacc        1200
ttgtctacac ataacggggt gtccttatgt gccctgctga tggacgaaaa actctctgtg       1260
ctgaacagtg cgtgtcgtat gacgttacgc tcactcatga agaccggacg cgacgttgat       1320
gcacacagag cttttcagcg agtcctctct caaggataca catcgctaat gtgctactat       1380
catccttcac ggaagttggc atatggtgag gtgctctttc tagaacgatc caatgacgtg       1440
acagatggga tcaagcttca gttggacgca tctagacagt gtcatgaatg tcctgtgttg       1500
cagcagaaag tggttgagtt agagaaacag attattatgc agaagtcaat ccagtcagac       1560
cctaccccag tggcgctgca accattgttg tctcagttgc gtgagttgtc tagtgaagtt       1620
actaggctac agatggagtt gagtcgagct cagtccctga atgctcagtt ggaggcggat       1680
gtcaagtcag ctcaatcatg tagcttggat atgtatctga gacaccacac ttgcattaat       1740
ggtcatgcta agaagatgaa attgcttgac gctgtgcgtg tcgcgccgga tgtgaggaga       1800
gaaatcatgg aaaagaggag tgaagtgaga caaggttggt gcgaacgtat ttctaaggaa       1860
gcagctgcca atgtcaaac tgttattgat gacctgactt tgatgaatgg aaagcaagca       1920
caagagataa cagaattacg tgattcggct gaaaaatatg agaaacagat tgcagagctg       1980
gtgagtacca tcacccaaaa ccagataacg tatcagcaag agctacaagc cttggtagcg       2040
aaaaatgtgg aattggacgc gttgaatcag cgtcaggcta agtctttgcg tattactccc       2100
tctcttctat cagccactcc tatcgattca gttgatgatg ttgctgactt aattgatttc       2160
tctgttccaa ctgatgagtt gtaaataatc cgtgatgcag tgttgcccta atcccttaag       2220
ccttcccgac ccccattcat c                                                 2241
```

<210> SEQ ID NO 8
<211> LENGTH: 3854
<212> TYPE: DNA
<213> ORGANISM: Reovirus

<400> SEQUENCE: 8

```
gctacacgtt ccacgacaat gtcatccatg atactgactc agtttggacc gttcattgag         60
agcatttcag gtatcactga tcaatcgaat gacgtgtttg aagatgcagc aaaagcattc        120
tctatgttta ctcgcagcga tgtctacaag gcgctggatg aaatacccttt ctctgatgat        180 gcgatgcttc caatccctcc aactatatat acgaaaccat ctcacgattc atattattac        240
attgatgctc taaccgtgt gcgtcgcaaa acatatcagg gccctgatga cgtgtacgta        300
cctaattgtt ctattgttga attgctggag ccacatgaga ctctgacatc ttatgggcgg        360
```

-continued

```
ttgtccgagg ccatcgagaa tcgtgccaag gatggggaca gccaagccag aatcgccaca      420
acgtatggta gaatcgctga atctcaagct cgacagatta aggctccatt ggagaagttt      480
gtgttggcac tattagtggc cgaagcaggg gggtctttat atgatccagt tttgcagaag      540
tatgatgaga ttccagatct atcgcataat tgcccttat ggtgttttag agagatctgt       600
cgtcacatat ctggtccatt accagatcgg gcaccttatc tttacttatc tgcaggggtt      660
ttctggttaa tgtcaccacg aatgacgtct gcaatccctc cgctactatc cgatcttgtt      720
aatttagcta ttttgcaaca aactgcgggt ttagatccat cattagtgaa attgggagta      780
cagatatgcc ttcatgcagc agctagctca agttatgcat ggtttatctt aaagactaag      840 tctattttc ctcaaaacac gttgcacagt atgtatgaat ctctagaagg gggatactgt       900
cctaatcttg aatggttaga gcctagatca gactataagt tcatgtacat gggagtcatg      960
ccattgtccg ctaagtatgc taggtcggcg ccgtccaatg ataagaaagc gcgggaactt     1020
ggcgagaaat atggactgag ctcagtcgtc ggtgagcttc gtaaacggac aaagacgtat     1080
gttaaacatg actttgcttc agtgaggtac attcgtgacg ctatggcatg tactagcggt     1140 atttcttgg taagaacacc caccgaaacg gtattgcaag aatatacgca gagtccggag      1200
attaaggttc ccattcccca gaaagactgg acaggcccaa taggtgaaat cagaattcta     1260
aaagatacaa caagttccat cgcgcgttac ttatatagaa catggtactt ggcagcggcg     1320
agaatggcgg ctcaaccacg tacgtgggat ccattgtttc aagcgattat gagatctcaa     1380
tacgtgacag ctaggggtgg atctggcgca gcactccgcg aatctttgta tgcaatcaat     1440
gtgtcgttac ctgatttcaa gggcttacca gtgaaggcag caactaagat attccaggcg     1500
gcacaattag cgaacttgcc gttctcccac acatcagtgg ctatactagc tgacacttca     1560
atgggattgc gaaatcaggt gcagaggcgg ccacgatcca ttatgccatt aaatgtgccc     1620
cagcagcagg tttcggcgcc ccatacattg acagcggatt acattaacta ccacatgaat     1680
ctatcaacca cgtctggtag tgcggtcatt gagaaggtga ttccttaagg tgtatacgct     1740
tcgagccctc ctaaccagtc gatcaacatt gacatatctg cgtgtgacgc tagtattact     1800
tgggatttct ttctgtcagt gattatggcg gctatacacg aaggtgtcgc tagtagctcc     1860
attggaaaac catttatggg ggttcctgca tccattgtaa atgatgagtc tgtcgttgga     1920
gtgagagctg ctaggccgat atcgggaatg cagaacatga ttcagcatct atcgaaacta     1980
tataaacgtg gattttcata tagagtaaac gattcttttt ctccaggtaa cgatttact     2040 catatgacta ccactttccc gtcaggttca acagccacct ctactgagca tactgctaat     2100
aatagtacga tgatggaaac tttcctgaca gtatggggac ccgaacatac tgacgaccct     2160
gacgtcttac gtttaatgaa gtctttaact attcaaagga attacgtatg tcaaggtgat     2220
gatggattaa tgattatcga tgggactact gctggtaagg tgaacagtga aactattcag     2280
aagatgctag aattaatctc aaaatatggt gaggaattcg gatggaaata tgacatagcg     2340
tacgatggga ctgccgaata cttaaagcta tacttcatat ttggctgtcg aattccaaat     2400
cttagtcgcc atccaatcgt ggggaaagaa cgggcgaatt cttcagcaga ggagccatgg     2460
ccagcaattc tagatcagat tatggtgtc ttctttaatg tgtgttcatga tgggttacag      2520 tggcagcggt ggatacgtta ttcatgggct ctatgctgtg cttcctcacg tcaaagaaca     2580
atgattggtg agagcgtggg ttaccttcaa tatcctatgt ggtcttttgt ctactgggga     2640
ttaccactgg ttaaagcgtt tgggtcagac ccatggatat tttcttggta catgcctact     2700
```

-continued

| | |
|---|---|
| ggagatctgg gaatgtatag ttggattagc ttgatacgcc ctctgatgac aagatggatg | 2760 |
| gtggctaatg gttacgtaac tgacagatgc tcacccgtat tcgggaacgc agattatcgc | 2820 |
| aggtgtttca atgaacttaa actatatcaa ggttattata tggcacaatt gcccaggaat | 2880 |
| cctaagaagt ctggacgagc ggcccctcgg gaggtaagag aacaattcac tcaggcatta | 2940 |
| tccgactatc tactgcaaaa tccagagctg aagtcacgtg tgctacgtgg tcgtagtgag | 3000 |
| tgggagaaat atggagcggg gataattcac aatcctccgt cattattcga tgtgccccat | 3060 |
| aaatggtatc agggtgcgca agaggcagca atcgctacga gagaagagct ggcagaaatg | 3120 |
| gatgagacat taatgcgcgc tcgaaggcac agatattcga gcttttcaaa gttattagag | 3180 |
| gcgtatctgc tcgtgaaatg gcgaatgtgc gaggcccgcg aaccgtcggt ggatttgcga | 3240 |
| ttaccattat gtgcgggtat tgacccatta aactcagatc ctttctcaa gatggtaagc | 3300 |
| gttggaccaa tgctccagag tacgagaaag tactttgctc agacactatt catggcaaag | 3360 |
| acggtgtcgg gtcttgacgt taacgcgatt gatagcgcgt tattacgact gcgaacatta | 3420 |
| ggtgctgata agaaagcatt aacggcgcag ttattaatgg tgggggcttca ggagtcagaa | 3480 |
| gcggacgcat tggccgggaa gataatgcta caggatgtga atactgtgca attagccaga | 3540 |
| gtggttaact tagctgtgcc agatacttgg atgtcgttag actttgactc tatgttcaaa | 3600 |
| caccacgtca agctgcttcc caaagatgga cgtcatctaa atactgatat tcctcctcga | 3660 |
| atgggatggt tacgggccat tttacgattc ttaggtgccg gaatggtaat gactgcgact | 3720 |
| ggagttgctg tcgacatcta tctgaggat atacatggcg gtggtcggtc acttggacag | 3780 |
| agattcatga cttggatgcg acaggaagga cggtcagcgt gagtctacca tgggtcgtgg | 3840 |
| tgcgtcaact catc | 3854 |

<210> SEQ ID NO 9
<211> LENGTH: 3916
<212> TYPE: DNA
<213> ORGANISM: Reovirus

<400> SEQUENCE: 9

| | |
|---|---|
| gctaaatggc gcgatggcga acgtttgggg ggtgagactt gcagactcgt tatcttcacc | 60 |
| cactattgag acacgaacgc gtcagtatac cttacacgat ctttgctcag acctagatgc | 120 |
| taatccgggg agggaaccgt ggaaacctct gcgtaatcag cgtactaata atattgtggc | 180 |
| tgtgcaatta ttcagaccat tgcagggttt agttttagat acccagcttt atggattcc | 240 |
| aggagcattt tgatgactggg agcgattcat gagagagaag ctgcgtgtgc taaagtatga | 300 |
| agtattgcgc atctatccaa tcagcaacta tagcaatgaa catgtcaacg tcttcgtggc | 360 |
| caatgctttg gtgggcgctt tcctgtcgaa tcaagctttc tatgacctgc taccgttgtt | 420 |
| gataattaat gacactatga ttggtgatct acttggcacg ggggcatcgc tatcacagtt | 480 |
| ctttcaatct catggagatg tgctggaagt cgcagctggt cgtaagtatc tgcagatgga | 540 |
| aaactactcc aacgatgacg atgatcctcc attatttgcg aaagacctgt cagattatgc | 600 |
| taaagcattc tacagtgaca catatgaagt gttggacagt tcttttgga cgcatgactc | 660 |
| ttcagcgggg gtcttagtgc attatgataa gccaacgaat ggtcatcact atctgctggg | 720 |
| tactttgact cagatggtca gtgcacctcc ttatattatt aacgctactg acgcaatgtt | 780 |
| gcttgaatcc tgtctagaac agttctcagc taatgtgcgt gcgagacctg cgcaacccgt | 840 |
| tacacgctta gaccaatgct atcatttaag atggggagca caatatgtag agaagattc | 900 |
| actgacatat cggttggggg tgttatcctt gctggctacc aatggatatc aattagctag | 960 |

-continued

```
accgattcca agacagttga cgaatcgatg gttgtcgagc tttgtgagtc aaattatgtc    1020
tgacggcgtc aacgagactc cactgtggcc ccaagaaagg tatgtgcaga tcgcttatga    1080
ttcaccatcc gttgttgatg gggctacgca atatggctat gtcaggaaga atcaactcag    1140
actcggcatg agaatatcgg cgctgcaatc gctgagtgat acgccctcgc cggtacagtg    1200
gcttccacaa tacaccatcg accaggcagc gatggacgaa ggcgatctga tggttagtcg    1260
gcttacgcaa ctcccgttac gtcctgatta tggtaatatc tgggtcggcg atgcgctatc    1320
ctattatgtg gactacaatc ggagtcatcg agtcgtgctt tcatcggaac ttcctcagct    1380
tccggacaca tattttgatg gcgatgaaca gtatgggcgc agcctgttct cactagctcg    1440
taagattggt gaccgctcgt tagtgaaaga tacggctgtc ttgaagcacg cttaccaagc    1500
catcgatcca aatactggta aggagtatct gagatctcgg caatctgtcg catattttgg    1560
tgcatcagcg ggtcattctg gtgccgacca gccgttagtc atagagccct ggattcaagg    1620
gaaaatcagt ggtgtgccgc caccctcctc agtgcgacag ttcggctatg atgttgcccg    1680
tggcgcgatc gtcgatctgg cgagaccatt tccttctgga gattatcaat ttgtctattc    1740
ggatgttgac caggtggtcg atggccatga cgatctgagt atatcatctg gactggtgga    1800
gagccttttg tcttcatgca tgcacgccac agcacccggg ggctcatttg ttgttaagat    1860
aaattttccg actagacccg tatggcacta catcgaacag aagatcttgc ccaatattac    1920
gtcatacatg ttgatcaagc ctttcgtcac caacaacgtc gaattgttct tcgtcgcttt    1980
cggtgtgcat caacactcat cacttacttg gacatctgga gtgtacttct tcttggtgga    2040
ccatttttat cgttatgaga ctttatctac gatctcacga caattgccgt cttttgggta    2100
tgttgatgat gggtcttccg tgactggtat cgagacaatt agtattgaga accctggctt    2160
ctcgaatatg acccaggccg ctcgcattgg tatctcagga ttgtgtgcta atgtaggtaa    2220
cgcgcgtaag tccattgcca tttacgaatc tcatggggcc agagtattaa ctatcacatc    2280
aaggagatct ccggcatcag ctagaagaaa gtctaggttg cgatatttgc cattaataga    2340
ccctaggtcg ttagaggtac aggcgcgcac tattctgcca gctgatccag tgttatttga    2400
aaacgtgagc ggagcgtcac cccatgtttg tctgacaatg atgtacaact cgaagtgtc     2460
gtcagcggta tatgatggag acgttgtgct agatcttggg acgggaccag aggctaaaat    2520
ccttgaactg atacccgcaa cctctccagt cacatgcgtg gacatacggc ctacagcgca    2580
gcctagtgga tgttggaacg ttcgtaccac gttccttgag ttagattatt tgagcgatgg    2640
atggatcact ggggtgcgtg gggacatagt tacttgtatg ttatctttgg gggccgctgc    2700
cgctggaaaa tcaatgactt ttgacgctgc gtttcagcaa ttaatcaaag tattatccaa    2760
gagtacggct aatgttgtgc tggtgcaggt taactgccct acagacgtgg tgaggagcat    2820
taagggctac ctagagatag attcgactaa caagaggtat aggttcccca aatttggtcg    2880
agacgagccg tactctgaca tggatgcgct ggagaaaata tgtcgtaccg cctggccaaa    2940
ctgctcaatt acctgggttc cattgtcata cgacttgcgg tggactagac tggcattatt    3000
agagtccacg acattgagta gcgcgtcgat tagaattgct gagctgatgt ataaatacat    3060
gcctattatg aggattgata ttcatggact acccatggaa aagcgaggta acttcatagt    3120
ggggcagaac tgctcattag taatccctgg ttttaatgcg caggatgtct ttaactgtta    3180
tttcaattcc gccctcgctt tctcgactga agatgtcaat gctgcgatga ttccccaagt    3240
gtctgcgcag tttgatgcga ctaagggtga gtggacgttg gatatggtct tctccgacgc    3300
```

-continued

```
aggaatctat accatgcagg ctctagtggg atctaatgct aatccagtct ctttgggttc      3360
ctttgtagtt gattctccag atgtagatat aactgacgct tggccagctc agttagactt      3420
tacgatcgcg ggaactgatg tcgatataac agttaatcct tattaccgtc tgatgacctt      3480
tgtaaggatc gatggacagt ggcagattgc caatccagac aaatttcaat tcttttcgtc      3540
ggcgtctggg acgttagtga tgaacgtcaa attagatatc gcagataaat atctactata      3600
ctatatacga gatgtccagt ctcgagatgt tggcttttac attcagcatc cacttcaact      3660
tttgaatacg atcacattgc caaccaacga ggacctttt ctgagcgcac ctgacatgcg       3720
agagtgggca gttaaggaaa gcggtaacac gatatgtata ctcaatagtc aagggtttgt      3780
gctacctcaa gattgggatg tgttaacaga taccataagt tggtccccat cgatacccac      3840
atacattgtg ccaccgggtg attataccttt gactcctctg taactcactg tccctcgtga    3900
gcgcgcctaa ttcatc                                                      3916

<210> SEQ ID NO 10
<211> LENGTH: 3901
<212> TYPE: DNA
<213> ORGANISM: Reovirus

<400> SEQUENCE: 10
gctaatcgtc aggatgaagc ggattccaag gaagacaaag gcaaatcca gcggaaaggg        60 caatgactca acagagagag cggacgatgg ctcgagccaa ttaagagaca agcaaaacaa      120
taaggctggc cccgccacta cggagcctgg cacatccaac cgagagcaat acaaagctcg      180
accaggtatt gcatctgtgc agagggccac tgaaagtgca gaaatgccca tgaagaataa      240
tgacgaaggg acgccagata agaaaggaaa tactaagggc gacctagtta atgagcatag      300
tgaggctaaa gacgaggcgg atgaagcgac gaagaagcag gcaaaggata cagacaaaag      360
taaagcgcaa gtcacatatt cagacactgg tatcaataat gctaatgaac tgtcaagatc      420
tgggaatgtg gataatgagg gtggaagtaa tcagaagccg atgtctacca gaatagctga      480
ggcaacgtct gctatagtgt cgaaacatcc tgcgcgtgtt gggctgccac ctaccgctag      540
cagtggtcat gggtatcagt gccatgtctg ttctgcagtc ctgtttagtc ctttagacct      600
agatgcccac gtcgcctcac atggtttgca tggtaacatg acattaacat cgagtgatat      660
ccagcgacat ataactgagt tcatcagctc atggcaaaat catcctattg ttcaagtttc      720
ggctgatgtc gaaaataaga aaactgctca attgcttcac gctgacactc ctcgactcgt      780
cacttgggat gctggtttgt gtacttcatt caaaatcgtc ccgattgtgc cagctcaggt      840
gccgcaggat gtactggcct atacgttttt cacctcttca tacgctatcc aatcaccgtt      900
tccagaggcg gcagtgtcta ggattgtggt gcatacgaga tgggcatcta atgttgactt      960
tgaccgagac tcgtctgtca tcatggcgcc acctacagaa aacaatatcc atttgtttaa     1020
acagttacta aatactgaaa ccctgtctgt aagggggct aatccgctaa tgttcagggc      1080
gaatgtgttg catatgttgc tagagttcgt attagataac ttgtatctga acagacatac      1140
gggattctct caagaccaca cgccatttac tgagggtgct aatttgcgtt cacttcctgg     1200
ccccgatgct gagaaatggt actcgattat gtatccaacg cgcatgggaa cgccgaatgt     1260
atccaaaata tgtaatttcg tcgcctcttg tgtgcgaaat cgggttggac ggttttgatcg    1320 agcacagatg atgaacggag ctatgtcaga gtgggtggat gtcttcgaga cttcagacgc     1380
gctaaccgtc tccattcgag gtcgatggat ggctagacta gctcgcatga acataaatcc     1440
aacagagatc gaatgggcat tgactgaatg tgcacaagga tatgtgactg tcacaagtcc     1500
```

```
ttacgctcct agcgtaaata gattgatgcc ctatcgtatc tccaacgctg agcggcaaat   1560
atcacagata atcaggatca tgaacattgg caataacgcg acggtgatac aacctgttct   1620
gcaagatatt tcggtactcc ttcaacgcat atcaccactc caaatagatc caactattat   1680
ttccaacact atgtcaacag tctcggagtc tactactcag accctcagcc ccgcgtcctc   1740
aattttgggt aaactacgac caagcaactc agattttcct agttttagag tcgcgttggc   1800
tggatggctt tataatgggg ttgtgacgac ggtgattgat gatagttcat atccaaaaga   1860
cggcggcagc gtgacctcac ttgaaaatct gtgggatttc ttcatccttg cgcttgctct   1920
accactgaca actgaccccct gtgcacctgt gaaagcattc atgaccctag ccaacatgat   1980
ggttggtttc gagacaatcc ctatggataa tcagatctat actcaatcga gacgcgcgag   2040
tgctttctca acgcctcaca cgtggccacg atgctttatg aacatccagt taatttctcc   2100
aatcgacgct cccatcttgc gacagtgggc tgaaattatt catagatact ggcctaaccc   2160
ttcacagatt cgttatggtg caccgaacgt tttcggctcg gcaaatttgt tcactccacc   2220
tgaggtgctg ttattgccaa tcgatcatca accagctaat gtaacaacgc caacgctgga   2280
cttcaccaat gagttaacta attggcgcgc tcgtgtctgt gagcttatga agaatctcgt   2340
tgataaccaa agatatcaac ctggatggac acaaagtcta gtctcgtcaa tgcgcggaac   2400
gctagacaaa ttgaagttga ttaaatcgat gacaccaatg tatctgcaac agctggctcc   2460
ggtagagtta gcagtgatag ctcccatgtt gccttttcca cctttccagg tgccatacgt   2520
ccgtctcgat cgtgacagag ttccaacaat ggttggagta acacgacatt cacgagatac   2580
tattactcag ccggcgctat cgctgtcgac aaccaatact actgttggcg tgccactagc   2640
tctagacgcg agggctatca ccgttgcgct gttgtcaggg aaatatccgc cggatttggt   2700
gacaaatgta tggtacgctg atgccattta cccaatgtat gcagacacgg aggtgttctc   2760
taatcttcag agagacatga ttacctgcga ggccgtgcag acattagtga ctctggtggc   2820
gcaaatatca gagacccagt atcctgtaga taggtatctt gattggatcc catcactgag   2880
agcatcggcg gcgacggcgg cgacatttgc tgagtgggtt aatacttcaa tgaagacggc   2940
gtttgatttg tctgatatgc tgttagagcc tctcctaagc ggtgatccga ggatgactca   3000
actagcgatt cagtatcagc agtacaatgg cagaacgttt aatatcatac ctgaaatgcc   3060
aggttcagta attgctgact gcgttcaatt aacagcagaa gtctttaatc acgaatataa   3120
cctgtttggg attgcgcggg gtgatatcat cattggccgt gttcagtcga cacatttgtg   3180
gtcaccgctg gctcctccac ctgacctggt gtttgatcgt gataccccctg tgttcacat   3240 cttcggacga gattgccgta tatcgtttgg aatgaatggc gccgcgccaa tgattagaga   3300
tgagactgga ctgatggtgc cttttgaagg aaattggatt ttcccactgg cgctttggca   3360
aatgaataca cgatattta atcaacagtt cgacgcgtgg attaagacag gagagttgcg   3420
aatccgcatt gagatgggcg cgtatccata tatgttgcat tactatgatc cacgtcagta   3480
cgctaatgca tggaatttaa catccgcctg gcttgaagaa attacgccga cgagcatccc   3540
atccgtgcct ttcatggtgc ccatttcaag tgatcatgac atttcctctg ccccagctgt   3600
ccaatatatc atttcaactg aatataatga tcggtctctg ttctgcacta actcatcatc   3660
tccccaaacc atcgctggac cagacaaaca cattccagtt gagagatata acattctgac   3720
caaccccgac gctccaccca cgcagataca actgcctgaa gtcgttgact tgtacaacgt   3780
cgtcacacgc tatgcgtatg agactccgcc tattaccgct gttgttatgg gtgttccttg   3840
```

```
atcctcatcc tcccaacagg tgctagagca ttgcgctcaa tgctagttgg gccgattcat    3900
c                                                                   3901
```

<210> SEQ ID NO 11
<211> LENGTH: 455
<212> TYPE: PRT
<213> ORGANISM: Reovirus

<400> SEQUENCE: 11

```
Met Asp Pro Arg Leu Arg Glu Glu Val Val Arg Leu Ile Ile Ala Leu
 1               5                  10                  15

Thr Ser Asp Asn Gly Ala Ser Leu Ser Lys Gly Leu Glu Ser Arg Val
             20                  25                  30

Ser Ala Leu Glu Lys Thr Ser Gln Ile His Ser Asp Thr Ile Leu Arg
         35                  40                  45

Ile Thr Gln Gly Leu Asp Asp Ala Asn Lys Arg Ile Ile Ala Leu Glu
     50                  55                  60

Gln Ser Arg Asp Asp Leu Val Ala Ser Val Ser Asp Ala Gln Leu Ala
 65                  70                  75                  80

Ile Ser Arg Leu Glu Ser Ser Ile Gly Ala Leu Gln Thr Val Val Asn
                 85                  90                  95

Gly Leu Asp Ser Ser Val Thr Gln Leu Gly Ala Arg Val Gly Gln Leu
            100                 105                 110

Glu Thr Gly Leu Ala Glu Leu Arg Val Asp His Asp Asn Leu Val Ala
        115                 120                 125

Arg Val Asp Thr Ala Glu Arg Asn Ile Gly Ser Leu Thr Thr Glu Leu
    130                 135                 140

Ser Thr Leu Thr Leu Arg Val Thr Ser Ile Gln Ala Asp Phe Glu Ser
145                 150                 155                 160

Arg Ile Ser Thr Leu Glu Arg Thr Ala Val Thr Ser Ala Gly Ala Pro
                165                 170                 175

Leu Ser Ile Arg Asn Asn Arg Met Thr Met Gly Leu Asn Asp Gly Leu
            180                 185                 190

Thr Leu Ser Gly Asn Asn Leu Ala Ile Arg Leu Pro Gly Asn Thr Gly
        195                 200                 205

Leu Asn Ile Gln Asn Gly Gly Leu Gln Phe Arg Phe Asn Thr Asp Gln
    210                 215                 220

Phe Gln Ile Val Asn Asn Asn Leu Thr Leu Lys Thr Thr Val Phe Asp
225                 230                 235                 240

Ser Ile Asn Ser Arg Ile Gly Ala Thr Glu Gln Ser Tyr Val Ala Ser
                245                 250                 255

Ala Val Thr Pro Leu Arg Leu Asn Ser Ser Thr Lys Val Leu Asp Met
            260                 265                 270

Leu Ile Asp Ser Ser Thr Leu Glu Ile Asn Ser Ser Gly Gln Leu Thr
        275                 280                 285

Val Arg Ser Thr Ser Pro Asn Leu Arg Tyr Pro Ile Ala Asp Val Ser
    290                 295                 300

Gly Gly Ile Gly Met Ser Pro Asn Tyr Arg Phe Arg Gln Ser Met Trp
305                 310                 315                 320

Ile Gly Ile Val Ser Tyr Ser Gly Ser Gly Leu Asn Trp Arg Val Gln
                325                 330                 335

Val Asn Ser Asp Ile Phe Ile Val Asp Asp Tyr Ile His Ile Cys Leu
            340                 345                 350

Pro Ala Phe Asp Gly Phe Ser Ile Ala Asp Gly Gly Asp Leu Ser Leu
```

-continued

```
               355                 360                 365
Asn Phe Val Thr Gly Leu Leu Pro Pro Leu Thr Gly Asp Thr Glu
        370                 375                 380
Pro Ala Phe His Asn Asp Val Val Thr Tyr Gly Ala Gln Thr Val Ala
385                 390                 395                 400
Ile Gly Leu Ser Ser Gly Ala Pro Gln Tyr Met Ser Lys Asn Leu
                405                 410                 415
Trp Val Glu Gln Trp Gln Asp Gly Val Leu Arg Leu Arg Val Glu Gly
            420                 425                 430
Gly Gly Ser Ile Thr His Ser Asn Ser Lys Trp Pro Ala Met Thr Val
        435                 440                 445
Ser Tyr Pro Arg Ser Phe Thr
        450             455

<210> SEQ ID NO 12
<211> LENGTH: 418
<212> TYPE: PRT
<213> ORGANISM: Reovirus

<400> SEQUENCE: 12

Met Ala Arg Ala Ala Phe Leu Phe Lys Thr Val Gly Phe Gly Gly Leu
1               5                   10                  15
Gln Asn Val Pro Ile Asn Asp Glu Leu Ser Ser His Leu Leu Arg Ala
            20                  25                  30
Gly Asn Ser Pro Trp Gln Leu Thr Gln Phe Leu Asp Trp Ile Ser Leu
        35                  40                  45
Gly Arg Gly Leu Ala Thr Ser Ala Leu Val Pro Thr Ala Gly Ser Arg
    50                  55                  60
Tyr Tyr Gln Met Ser Cys Leu Leu Ser Gly Thr Leu Gln Ile Pro Phe
65                  70                  75                  80
Arg Pro Asn His Arg Trp Gly Asp Ile Arg Phe Leu Arg Leu Val Trp
                85                  90                  95
Ser Ala Pro Thr Leu Asp Gly Leu Val Val Ala Pro Pro Gln Val Leu
            100                 105                 110
Ala Gln Pro Ala Leu Gln Ala Gln Ala Asp Arg Val Tyr Asp Cys Asp
        115                 120                 125
Asp Tyr Pro Phe Leu Ala Arg Asp Pro Arg Phe Lys His Arg Val Tyr
    130                 135                 140
Gln Gln Leu Ser Ala Val Thr Leu Leu Asn Leu Thr Gly Phe Gly Pro
145                 150                 155                 160
Ile Ser Tyr Val Arg Val Asp Glu Asp Met Trp Ser Gly Asp Val Asn
                165                 170                 175
Gln Leu Leu Met Asn Tyr Phe Gly His Thr Phe Ala Glu Ile Ala Tyr
            180                 185                 190
Thr Leu Cys Gln Ala Ser Ala Asn Arg Pro Trp Glu Tyr Asp Gly Thr
        195                 200                 205
Tyr Ala Arg Met Thr Gln Ile Val Leu Ser Leu Phe Trp Leu Ser Tyr
    210                 215                 220
Val Gly Val Ile His Gln Gln Asn Thr Tyr Arg Thr Phe Tyr Phe Gln
225                 230                 235                 240
Cys Asn Arg Arg Gly Asp Ala Ala Glu Val Trp Ile Leu Ser Cys Ser
                245                 250                 255
Leu Asn His Ser Ala Gln Ile Arg Pro Gly Asn Arg Ser Leu Phe Val
            260                 265                 270
```

```
Met Pro Thr Ser Pro Asp Trp Asn Met Asp Val Asn Leu Ile Leu Ser
        275                 280                 285

Ser Thr Leu Thr Gly Cys Leu Cys Ser Gly Ser Gln Leu Pro Leu Ile
        290                 295                 300

Asp Asn Asn Ser Val Pro Ala Val Ser Arg Asn Ile His Gly Trp Thr
305                 310                 315                 320

Gly Arg Ala Gly Asn Gln Leu His Gly Phe Gln Val Arg Arg Met Val
                325                 330                 335

Thr Glu Phe Cys Asp Arg Leu Arg Arg Asp Gly Val Met Thr Gln Ala
            340                 345                 350

Gln Gln Asn Gln Val Glu Ala Leu Ala Asp Gln Thr Gln Gln Phe Lys
        355                 360                 365

Arg Asp Lys Leu Glu Thr Trp Ala Arg Glu Asp Gln Tyr Asn Gln
370                 375                 380

Ala His Pro Asn Ser Thr Met Phe Arg Thr Lys Pro Phe Thr Asn Ala
385                 390                 395                 400

Gln Trp Gly Arg Gly Asn Thr Gly Ala Thr Ser Ala Ala Ile Ala Ala
                405                 410                 415

Leu Ile

<210> SEQ ID NO 13
<211> LENGTH: 254
<212> TYPE: PRT
<213> ORGANISM: Reovirus

<400> SEQUENCE: 13

Met Ala Ser Ser Leu Arg Ala Ala Ile Ser Lys Ile Lys Arg Asp Asp
  1               5                  10                  15

Val Gly Gln Gln Val Cys Pro Asn Tyr Val Met Leu Arg Ser Ser Val
                 20                  25                  30

Thr Thr Lys Val Val Arg Asn Val Val Glu Tyr Gln Ile Arg Thr Gly
             35                  40                  45

Gly Phe Phe Ser Cys Leu Ala Met Leu Arg Pro Leu Gln Tyr Ala Lys
         50                  55                  60

Arg Glu Arg Leu Leu Gly Gln Arg Asn Leu Glu Arg Ile Ser Thr Arg
 65                  70                  75                  80

Asp Ile Leu Gln Thr Arg Asp Leu His Ser Leu Cys Met Pro Thr Pro
                 85                  90                  95

Asp Ala Pro Met Ser Asn His Gln Ala Ser Thr Met Arg Glu Leu Ile
                100                 105                 110

Cys Ser Tyr Phe Lys Val Asp His Ala Asp Gly Leu Lys Tyr Ile Pro
            115                 120                 125

Met Asp Glu Arg Tyr Ser Pro Ser Ser Leu Ala Arg Leu Phe Thr Met
130                 135                 140

Gly Met Ala Gly Leu His Ile Thr Thr Glu Pro Ser Tyr Lys Arg Val
145                 150                 155                 160

Pro Ile Met His Leu Ala Ala Asp Leu Asp Cys Met Thr Leu Ala Leu
                165                 170                 175

Pro Tyr Met Ile Thr Leu Asp Gly Asp Thr Val Val Pro Val Ala Pro
            180                 185                 190

Thr Leu Ser Ala Glu Gln Leu Leu Asp Asp Gly Leu Lys Gly Leu Ala
        195                 200                 205

Cys Met Asp Met Asp Val Arg Trp Thr Arg Ile Ala Gly Arg Leu Val
210                 215                 220
```

```
Ile Arg Val Trp Thr Leu His Ala Ala Ser Thr Ser Cys Ile Ala Arg
225                 230                 235                 240

Arg Gln Gln Lys Pro Ser Val Cys Leu Arg His Ala Leu Cys
                245                 250

<210> SEQ ID NO 14
<211> LENGTH: 366
<212> TYPE: PRT
<213> ORGANISM: Reovirus

<400> SEQUENCE: 14

Met Ala Ser Ser Leu Arg Ala Ala Ile Ser Lys Ile Lys Arg Asp Asp
 1               5                  10                  15

Val Gly Gln Gln Val Cys Pro Asn Tyr Val Met Leu Arg Ser Ser Val
             20                  25                  30

Thr Thr Lys Val Val Arg Asn Val Val Glu Tyr Gln Ile Arg Thr Gly
         35                  40                  45

Gly Phe Phe Ser Cys Leu Ala Met Leu Arg Pro Leu Gln Tyr Ala Lys
     50                  55                  60

Arg Glu Arg Leu Leu Gly Gln Arg Asn Leu Glu Arg Ile Ser Thr Arg
 65                  70                  75                  80

Asp Ile Leu Gln Thr Arg Asp Leu His Ser Leu Cys Met Pro Thr Pro
                 85                  90                  95

Asp Ala Pro Met Ser Asn His Gln Ala Ser Thr Met Arg Glu Leu Ile
            100                 105                 110

Cys Ser Tyr Phe Lys Val Asp His Ala Asp Gly Leu Lys Tyr Ile Pro
        115                 120                 125

Met Asp Glu Arg Tyr Ser Pro Ser Ser Leu Ala Arg Leu Phe Thr Met
    130                 135                 140

Gly Met Ala Gly Leu His Ile Thr Thr Glu Pro Ser Tyr Lys Arg Val
145                 150                 155                 160

Pro Ile Met His Leu Ala Ala Asp Leu Asp Cys Met Thr Leu Ala Leu
                165                 170                 175

Pro Tyr Met Ile Thr Leu Asp Gly Asp Thr Val Val Pro Val Ala Pro
            180                 185                 190

Thr Leu Ser Ala Glu Gln Leu Leu Asp Asp Gly Leu Lys Gly Leu Ala
        195                 200                 205

Cys Met Asp Ile Ser Tyr Gly Cys Glu Val Asp Ala Asn Ser Arg Pro
    210                 215                 220

Ala Gly Asp Gln Ser Met Asp Ser Ser Arg Cys Ile Asn Glu Leu Tyr
225                 230                 235                 240

Cys Glu Glu Thr Ala Glu Ala Ile Cys Val Leu Lys Thr Cys Leu Val
                245                 250                 255

Leu Asn Cys Met Gln Phe Lys Leu Glu Met Asp Asp Leu Ala His Asn
            260                 265                 270

Ala Ala Glu Leu Asp Lys Ile Gln Met Met Ile Pro Phe Ser Glu Arg
        275                 280                 285

Val Phe Arg Met Ala Ser Ser Phe Ala Thr Ile Asp Ala Gln Cys Phe
    290                 295                 300

Arg Phe Cys Val Met Met Lys Asp Lys Asn Leu Lys Ile Asp Met Arg
305                 310                 315                 320

Glu Thr Thr Arg Leu Trp Thr Arg Ser Ala Ser Asp Ser Val Ala
                325                 330                 335

Thr Ser Ser Leu Ser Ile Ser Leu Asp Arg Gly Arg Trp Val Ala Ala
            340                 345                 350
```

```
Asp Ala Ser Asp Ala Arg Leu Leu Val Phe Pro Ile Arg Val
        355                 360                 365
```

<210> SEQ ID NO 15
<211> LENGTH: 365
<212> TYPE: PRT
<213> ORGANISM: Reovirus

<400> SEQUENCE: 15

```
Met Glu Val Cys Leu Pro Asn Gly His Gln Val Val Asp Leu Ile Asn
  1               5                  10                  15

Asn Ala Phe Glu Gly Arg Val Ser Ile Tyr Ser Ala Gln Glu Gly Trp
             20                  25                  30

Asp Lys Thr Ile Ser Ala Gln Pro Asp Met Met Val Cys Gly Gly Ala
         35                  40                  45

Val Val Cys Met His Cys Leu Gly Val Val Gly Ser Leu Gln Arg Lys
     50                  55                  60

Leu Lys His Leu Pro His His Arg Cys Asn Gln Gln Ile Arg His Gln
 65                  70                  75                  80

Asp Tyr Val Asp Val Gln Phe Ala Asp Arg Val Thr Ala His Trp Lys
                 85                  90                  95

Arg Gly Met Leu Ser Phe Val Ala Gln Met His Glu Met Met Asn Asp
            100                 105                 110

Val Ser Pro Asp Asp Leu Asp Arg Val Arg Thr Glu Gly Gly Ser Leu
        115                 120                 125

Val Glu Leu Asn Arg Leu Gln Val Asp Pro Asn Ser Met Phe Arg Ser
    130                 135                 140

Ile His Ser Ser Trp Thr Asp Pro Leu Gln Val Val Asp Asp Leu Asp
145                 150                 155                 160

Thr Lys Leu Asp Gln Tyr Trp Thr Ala Leu Asn Leu Met Ile Asp Ser
                165                 170                 175

Ser Asp Leu Ile Pro Asn Phe Met Met Arg Asp Pro Ser His Ala Phe
            180                 185                 190

Asn Gly Val Lys Leu Lys Gly Asp Ala Arg Gln Thr Gln Phe Ser Arg
        195                 200                 205

Thr Phe Asp Ser Arg Ser Ser Leu Glu Trp Gly Val Met Val Tyr Asp
    210                 215                 220

Tyr Ser Glu Leu Asp His Asp Pro Ser Lys Gly Arg Ala Tyr Arg Lys
225                 230                 235                 240

Glu Leu Val Thr Pro Ala Arg Asp Phe Gly His Phe Gly Leu Ser His
                245                 250                 255

Tyr Ser Arg Ala Thr Thr Pro Ile Leu Gly Lys Met Pro Ala Val Phe
            260                 265                 270

Ser Gly Met Leu Thr Gly Asn Cys Lys Met Tyr Pro Phe Ile Lys Gly
        275                 280                 285

Thr Ala Lys Leu Lys Thr Val Arg Lys Leu Val Glu Ala Val Asn His
    290                 295                 300

Ala Trp Gly Val Glu Lys Ile Arg Tyr Ala Leu Gly Pro Gly Gly Met
305                 310                 315                 320

Thr Gly Trp Tyr Asn Arg Thr Met Gln Gln Ala Pro Ile Val Leu Thr
                325                 330                 335

Pro Ala Ala Leu Thr Met Phe Pro Asp Thr Ile Lys Phe Gly Asp Leu
            340                 345                 350

Asn Tyr Pro Val Met Ile Gly Asp Pro Met Ile Leu Gly
        355                 360                 365
```

-continued 355                     360                     365

<210> SEQ ID NO 16
<211> LENGTH: 736
<212> TYPE: PRT
<213> ORGANISM: Reovirus

<400> SEQUENCE: 16

```
Met Ala Tyr Ile Ala Val Pro Ala Val Val Asp Ser Arg Ser Ser Glu
1               5                   10                  15

Ala Ile Gly Leu Leu Glu Ser Phe Gly Val Asp Ala Gly Ala Asp Ala
            20                  25                  30

Asn Asp Val Ser Tyr Gln Asp His Asp Tyr Val Leu Asp Gln Leu Gln
        35                  40                  45

Tyr Met Leu Asp Gly Tyr Glu Ala Gly Asp Val Ile Asp Ala Leu Val
    50                  55                  60

His Lys Asn Trp Leu His His Ser Val Tyr Cys Leu Leu Pro Pro Lys
65                  70                  75                  80

Ser Gln Leu Leu Glu Tyr Trp Lys Ser Asn Pro Ser Ala Ile Pro Asp
                85                  90                  95

Asn Val Asp Arg Arg Leu Arg Lys Arg Leu Met Leu Lys Lys Asp Leu
            100                 105                 110

Arg Lys Asp Asp Glu Tyr Asn Gln Leu Ala Arg Ala Phe Lys Ile Ser
        115                 120                 125

Asp Val Tyr Ala Pro Leu Ile Ser Ser Thr Thr Ser Pro Met Thr Met
    130                 135                 140

Ile Gln Asn Leu Asn Arg Gly Glu Ile Val Tyr Thr Thr Thr Asp Arg
145                 150                 155                 160

Val Ile Gly Ala Arg Ile Leu Leu Tyr Ala Pro Arg Lys Tyr Tyr Ala
                165                 170                 175

Ser Thr Leu Ser Phe Thr Met Thr Lys Cys Ile Ile Pro Phe Gly Lys
            180                 185                 190

Glu Val Gly Arg Val Pro His Ser Arg Phe Asn Val Gly Thr Phe Pro
        195                 200                 205

Ser Ile Ala Thr Pro Lys Cys Phe Val Met Ser Gly Val Asp Ile Glu
    210                 215                 220

Ser Ile Pro Asn Glu Phe Ile Lys Leu Phe Tyr Gln Arg Val Lys Ser
225                 230                 235                 240

Val His Ala Asn Ile Leu Asn Asp Ile Ser Pro Gln Ile Val Ser Asp
                245                 250                 255

Met Ile Asn Arg Lys Arg Leu Arg Val His Thr Pro Ser Asp Arg Arg
            260                 265                 270

Ala Ala Gln Leu Met His Leu Pro Tyr His Val Lys Arg Gly Ala Ser
        275                 280                 285

His Val Asp Val Tyr Lys Val Ala Val Asp Met Leu Phe Glu Val
    290                 295                 300

Val Asp Val Ala Asp Gly Leu Arg Asn Val Ser Arg Lys Leu Thr Met
305                 310                 315                 320

His Thr Val Pro Val Cys Ile Leu Glu Met Leu Gly Ile Glu Ile Ala
                325                 330                 335

Asp Tyr Cys Ile Arg Gln Glu Asp Gly Met Leu Thr Asp Trp Phe Leu
            340                 345                 350

Leu Leu Thr Met Leu Ser Asp Gly Leu Thr Asp Arg Arg Thr His Cys
        355                 360                 365
```

```
Gln Tyr Leu Ile Asn Pro Ser Ser Val Pro Pro Asp Val Ile Leu Asn
    370                 375                 380

Ile Ser Ile Thr Gly Phe Ile Asn Arg His Thr Ile Asp Val Met Pro
385                 390                 395                 400

Asp Ile Tyr Asp Phe Val Lys Pro Ile Gly Ala Val Leu Pro Lys Gly
                405                 410                 415

Ser Phe Lys Ser Thr Ile Met Arg Val Leu Asp Ser Ile Ser Ile Leu
                420                 425                 430

Gly Ile Gln Ile Met Pro Arg Ala His Val Val Asp Ser Asp Glu Val
                435                 440                 445

Gly Glu Gln Met Glu Pro Thr Phe Glu Gln Ala Val Met Glu Ile Tyr
            450                 455                 460

Lys Gly Ile Ala Gly Val Asp Ser Leu Asp Asp Leu Ile Lys Trp Val
465                 470                 475                 480

Leu Asn Ser Asp Leu Ile Pro His Asp Asp Arg Leu Gly Gln Leu Phe
                485                 490                 495

Gln Ala Phe Leu Pro Leu Ala Lys Asp Leu Leu Ala Pro Met Ala Arg
                500                 505                 510

Lys Phe Tyr Asp Asn Ser Met Ser Glu Gly Arg Leu Leu Thr Phe Ser
            515                 520                 525

His Ala Asp Ser Glu Leu Leu Asn Ala Asn Tyr Phe Gly His Leu Leu
530                 535                 540

Arg Leu Lys Ile Pro Tyr Ile Thr Glu Val Asn Leu Met Ile Arg Lys
545                 550                 555                 560

Asn Arg Glu Gly Gly Glu Leu Phe Gln Leu Val Leu Ser Tyr Leu Tyr
                565                 570                 575

Lys Met Tyr Ala Thr Ser Ala Gln Pro Lys Trp Phe Gly Ser Leu Leu
            580                 585                 590

Arg Leu Leu Ile Cys Pro Trp Leu His Met Glu Lys Leu Ile Gly Glu
            595                 600                 605

Ala Asp Pro Ala Ser Thr Ser Ala Glu Ile Gly Trp His Ile Pro Arg
610                 615                 620

Glu Gln Leu Met Gln Asp Gly Trp Cys Gly Cys Glu Asp Gly Phe Ile
625                 630                 635                 640

Pro Tyr Val Ser Ile Arg Ala Pro Arg Leu Val Ile Glu Glu Leu Met
                645                 650                 655

Glu Lys Asn Trp Gly Gln Tyr His Ala Gln Val Ile Val Thr Asp Gln
            660                 665                 670

Leu Val Val Gly Glu Pro Arg Arg Val Ser Ala Lys Ala Val Ile Lys
            675                 680                 685

Gly Asn His Leu Pro Val Lys Leu Val Ser Arg Phe Ala Cys Phe Thr
            690                 695                 700

Leu Thr Ala Lys Tyr Glu Met Arg Leu Ser Cys Gly His Ser Thr Gly
705                 710                 715                 720

Arg Gly Ala Ala Tyr Ser Ala Arg Leu Ala Phe Arg Ser Asp Leu Ala
                725                 730                 735

<210> SEQ ID NO 17
<211> LENGTH: 708
<212> TYPE: PRT
<213> ORGANISM: Reovirus

<400> SEQUENCE: 17

Met Gly Asn Ala Ser Ser Ile Val Gln Thr Ile Asn Val Thr Gly Asp
1               5                   10                  15
```

-continued

```
Gly Asn Val Phe Lys Pro Ser Ala Glu Thr Ser Ser Thr Ala Val Pro
             20                  25                  30

Ser Leu Ser Leu Ser Pro Gly Met Leu Asn Pro Gly Gly Val Pro Trp
         35                  40                  45

Ile Ala Val Gly Asp Glu Thr Ser Val Thr Ser Pro Gly Ala Leu Arg
     50                  55                  60

Arg Met Thr Ser Lys Asp Ile Pro Asp Thr Ala Ile Ile Asn Thr Asp
 65                  70                  75                  80

Asn Ser Ser Gly Ala Val Pro Ser Glu Ser Ala Leu Val Pro Tyr Ile
                 85                  90                  95

Asp Glu Pro Leu Val Val Val Thr Glu His Ala Ile Thr Asn Phe Thr
            100                 105                 110

Lys Ala Glu Met Ala Leu Glu Phe Asn Arg Glu Phe Leu Asp Lys Met
            115                 120                 125

Arg Val Leu Ser Val Ser Pro Lys Tyr Ser Asp Leu Leu Thr Tyr Val
            130                 135                 140

Asp Cys Tyr Val Gly Val Ser Ala Arg Gln Ala Leu Asn Asn Phe Gln
145                 150                 155                 160

Lys Gln Val Pro Val Ile Thr Pro Thr Arg Gln Thr Met Tyr Val Asp
                165                 170                 175

Ser Ile Gln Ala Ala Leu Lys Ala Leu Glu Lys Trp Glu Ile Asp Leu
            180                 185                 190

Arg Val Ala Gln Thr Leu Leu Pro Thr Asn Val Pro Ile Gly Glu Val
            195                 200                 205

Ser Cys Pro Met Gln Ser Val Val Lys Leu Leu Asp Asp Gln Leu Pro
            210                 215                 220

Asp Asp Ser Leu Ile Arg Arg Tyr Pro Lys Glu Ala Ala Val Ala Leu
225                 230                 235                 240

Ala Lys Arg Asn Gly Gly Ile Gln Trp Met Asp Val Ser Glu Gly Thr
                245                 250                 255

Val Met Asn Glu Ala Val Asn Ala Val Ala Ala Ser Ala Leu Ala Pro
            260                 265                 270

Ser Ala Ser Ala Pro Pro Leu Glu Glu Lys Ser Lys Leu Thr Glu Gln
        275                 280                 285

Ala Met Asp Leu Val Thr Ala Ala Glu Pro Glu Ile Ile Ala Ser Leu
        290                 295                 300

Ala Pro Val Pro Ala Pro Val Phe Ala Ile Pro Pro Lys Pro Ala Asp
305                 310                 315                 320

Tyr Asn Val Arg Thr Leu Arg Ile Asp Glu Ala Thr Trp Leu Arg Met
                325                 330                 335

Ile Pro Lys Ser Met Asn Thr Pro Phe Gln Ile Gln Val Thr Asp Asn
            340                 345                 350

Thr Gly Thr Asn Trp His Leu Asn Leu Arg Gly Gly Thr Arg Val Val
        355                 360                 365

Asn Leu Asp Gln Ile Ala Pro Met Arg Phe Val Leu Asp Leu Gly Gly
    370                 375                 380

Lys Ser Tyr Lys Glu Thr Ser Trp Asp Pro Asn Gly Lys Lys Val Gly
385                 390                 395                 400

Phe Ile Val Phe Gln Ser Lys Ile Pro Phe Glu Leu Trp Thr Ala Ala
                405                 410                 415

Ser Gln Ile Gly Gln Ala Thr Val Val Asn Tyr Val Gln Leu Tyr Ala
            420                 425                 430
```

```
Glu Asp Ser Ser Phe Thr Ala Gln Ser Ile Ile Ala Thr Thr Ser Leu
                435                 440                 445

Ala Tyr Asn Tyr Glu Pro Glu Gln Leu Asn Lys Thr Asp Pro Glu Met
    450                 455                 460

Asn Tyr Tyr Leu Leu Ala Thr Phe Ile Asp Ser Ala Ala Ile Thr Pro
465                 470                 475                 480

Thr Asn Met Thr Gln Pro Asp Val Trp Asp Ala Leu Leu Thr Met Ser
                485                 490                 495

Pro Leu Ser Ala Gly Glu Val Thr Val Lys Gly Ala Val Val Ser Glu
                500                 505                 510

Val Val Pro Ala Asp Leu Ile Gly Ser Tyr Thr Pro Glu Ser Leu Asn
            515                 520                 525

Ala Ser Leu Pro Asn Asp Ala Ala Arg Cys Met Ile Asp Arg Ala Ser
        530                 535                 540

Lys Ile Ala Glu Ala Ile Lys Ile Asp Asp Ala Gly Pro Asp Glu
545                 550                 555                 560

Tyr Ser Pro Asn Ser Val Pro Ile Gln Gly Gln Leu Ala Ile Ser Gln
                565                 570                 575

Leu Glu Thr Gly Tyr Gly Val Arg Ile Phe Asn Pro Lys Gly Ile Leu
                580                 585                 590

Ser Lys Ile Ala Ser Arg Ala Met Gln Ala Phe Ile Gly Asp Pro Ser
            595                 600                 605

Thr Ile Ile Thr Gln Ala Ala Pro Val Leu Ser Asp Lys Asn Asn Trp
        610                 615                 620

Ile Ala Leu Ala Gln Gly Val Lys Thr Ser Leu Arg Thr Lys Ser Leu
625                 630                 635                 640

Ser Ala Gly Val Lys Thr Ala Val Ser Lys Leu Ser Ser Ser Glu Ser
                645                 650                 655

Ile Gln Asn Trp Thr Gln Gly Phe Leu Asp Lys Val Ser Ala His Phe
                660                 665                 670

Pro Ala Pro Lys Pro Asp Cys Pro Thr Ser Gly Asp Ser Gly Glu Ser
            675                 680                 685

Ser Asn Arg Arg Val Lys Arg Asp Ser Tyr Ala Gly Val Val Lys Arg
        690                 695                 700

Gly Tyr Thr Arg
705

<210> SEQ ID NO 18
<211> LENGTH: 721
<212> TYPE: PRT
<213> ORGANISM: Reovirus

<400> SEQUENCE: 18

Met Ala Ser Phe Lys Gly Phe Ser Ala Asn Thr Val Pro Val Ser Lys
1               5                   10                  15

Ala Lys Arg Asp Ile Ser Ser Leu Ala Ala Thr Pro Gly Leu Arg Ser
                20                  25                  30

Gln Ser Phe Thr Pro Ser Val Asp Met Ser Gln Ser Arg Glu Phe Leu
            35                  40                  45

Thr Lys Ala Ile Glu Gln Gly Ser Met Ser Ile Pro Tyr Gln His Val
        50                  55                  60

Asn Val Pro Lys Val Asp Arg Lys Val Val Ser Leu Val Val Arg Pro
65                  70                  75                  80

Phe Ser Ser Gly Ala Phe Ser Ile Ser Gly Val Ile Ser Pro Ala His
                85                  90                  95
```

```
Ala Tyr Leu Leu Glu Cys Leu Pro Gln Leu Glu Gln Ala Met Ala Phe
            100                 105                 110

Val Ala Ser Pro Glu Ser Phe Gln Ala Ser Asp Val Ala Lys Arg Phe
        115                 120                 125

Ala Ile Lys Pro Gly Met Ser Leu Gln Asp Ala Ile Thr Ala Phe Ile
    130                 135                 140

Asn Phe Val Ser Ala Met Leu Lys Met Thr Val Thr Arg Gln Asn Phe
145                 150                 155                 160

Asp Val Ile Val Ala Glu Ile Glu Arg Leu Ala Ser Thr Ser Val Ser
                165                 170                 175

Val Arg Thr Glu Glu Ala Lys Val Ala Asp Glu Glu Leu Met Leu Phe
            180                 185                 190

Gly Leu Asp His Arg Gly Pro Gln Gln Leu Asp Val Ser Asp Ala Lys
        195                 200                 205

Gly Ile Met Lys Ala Ala Asp Ile Gln Thr Thr His Asp Val His Leu
    210                 215                 220

Ala Pro Gly Val Gly Asn Ile Asp Pro Glu Ile Tyr Asn Glu Gly Arg
225                 230                 235                 240

Phe Met Phe Met Gln His Lys Pro Leu Ala Ala Asp Gln Ser Tyr Phe
                245                 250                 255

Thr Leu Glu Thr Ala Asp Tyr Phe Lys Ile Tyr Pro Thr Tyr Asp Glu
            260                 265                 270

His Asp Gly Arg Met Ala Asp Gln Lys Gln Ser Gly Leu Ile Leu Cys
        275                 280                 285

Thr Lys Asp Glu Val Leu Ala Glu Gln Thr Ile Phe Lys Leu Asp Ala
    290                 295                 300

Pro Asp Asp Lys Thr Val His Leu Leu Asp Arg Asp Asp His Val
305                 310                 315                 320

Val Ala Arg Phe Thr Lys Val Phe Ile Glu Asp Val Ala Pro Gly His
                325                 330                 335

His Ala Ala Gln Arg Ser Gly Gln Arg Ser Val Leu Asp Asp Leu Tyr
            340                 345                 350

Ala Asn Thr Gln Val Ile Ser Ile Thr Ser Ala Ala Leu Lys Trp Val
        355                 360                 365

Val Lys His Gly Val Ser Asp Gly Ile Val Asn Arg Lys Asn Val Lys
    370                 375                 380

Val Cys Val Gly Phe Asp Pro Leu Tyr Thr Leu Ser Thr His Asn Gly
385                 390                 395                 400

Val Ser Leu Cys Ala Leu Leu Met Asp Glu Lys Leu Ser Val Leu Asn
                405                 410                 415

Ser Ala Cys Arg Met Thr Leu Arg Ser Leu Met Lys Thr Gly Arg Asp
            420                 425                 430

Val Asp Ala His Arg Ala Phe Gln Arg Val Leu Ser Gln Gly Tyr Thr
        435                 440                 445

Ser Leu Met Cys Tyr Tyr His Pro Ser Arg Lys Leu Ala Tyr Gly Glu
    450                 455                 460

Val Leu Phe Leu Glu Arg Ser Asn Asp Val Thr Asp Gly Ile Lys Leu
465                 470                 475                 480

Gln Leu Asp Ala Ser Arg Gln Cys His Glu Cys Pro Val Leu Gln Gln
                485                 490                 495

Lys Val Val Glu Leu Glu Lys Gln Ile Ile Met Gln Lys Ser Ile Gln
            500                 505                 510
```

```
Ser Asp Pro Thr Pro Val Ala Leu Gln Pro Leu Leu Ser Gln Leu Arg
        515                 520                 525

Glu Leu Ser Ser Glu Val Thr Arg Leu Gln Met Glu Leu Ser Arg Ala
        530                 535                 540

Gln Ser Leu Asn Ala Gln Leu Glu Ala Asp Val Lys Ser Ala Gln Ser
545                 550                 555                 560

Cys Ser Leu Asp Met Tyr Leu Arg His His Thr Cys Ile Asn Gly His
                565                 570                 575

Ala Lys Glu Asp Glu Leu Leu Asp Ala Val Arg Val Ala Pro Asp Val
        580                 585                 590

Arg Arg Glu Ile Met Glu Lys Arg Ser Glu Val Arg Gln Gly Trp Cys
        595                 600                 605

Glu Arg Ile Ser Lys Glu Ala Ala Lys Cys Gln Thr Val Ile Asp
        610                 615                 620

Asp Leu Thr Leu Met Asn Gly Lys Gln Ala Gln Glu Ile Thr Glu Leu
625                 630                 635                 640

Arg Asp Ser Ala Glu Lys Tyr Glu Lys Gln Ile Ala Glu Leu Val Ser
                645                 650                 655

Thr Ile Thr Gln Asn Gln Ile Thr Tyr Gln Gln Glu Leu Gln Ala Leu
        660                 665                 670

Val Ala Lys Asn Val Glu Leu Asp Ala Leu Asn Gln Arg Gln Ala Lys
        675                 680                 685

Ser Leu Arg Ile Thr Pro Ser Leu Leu Ser Ala Thr Pro Ile Asp Ser
        690                 695                 700

Val Asp Asp Val Ala Asp Leu Ile Asp Phe Ser Pro Thr Asp Glu
705                 710                 715                 720

Leu

<210> SEQ ID NO 19
<211> LENGTH: 1267
<212> TYPE: PRT
<213> ORGANISM: Reovirus

<400> SEQUENCE: 19

Met Ser Ser Met Ile Leu Thr Gln Phe Gly Pro Phe Ile Glu Ser Ile
1               5                   10                  15

Ser Gly Ile Thr Asp Gln Ser Asn Asp Val Phe Glu Asp Ala Ala Lys
                20                  25                  30

Ala Phe Ser Met Phe Thr Arg Ser Asp Val Tyr Lys Ala Leu Asp Glu
            35                  40                  45

Ile Pro Phe Ser Asp Asp Ala Met Leu Pro Ile Pro Pro Thr Ile Tyr
        50                  55                  60

Thr Lys Pro Ser His Asp Ser Tyr Tyr Ile Asp Ala Leu Asn Arg
65                  70                  75                  80

Val Arg Arg Lys Thr Tyr Gln Gly Pro Asp Asp Val Tyr Val Pro Asn
                85                  90                  95

Cys Ser Ile Val Glu Leu Leu Glu Pro His Glu Thr Leu Thr Ser Tyr
            100                 105                 110

Gly Arg Leu Ser Glu Ala Ile Glu Asn Arg Ala Lys Asp Gly Asp Ser
        115                 120                 125

Gln Ala Arg Ile Ala Thr Thr Tyr Gly Arg Ile Ala Glu Ser Gln Ala
130                 135                 140

Arg Gln Ile Lys Ala Pro Leu Glu Lys Phe Val Leu Ala Leu Leu Val
145                 150                 155                 160
```

```
Ala Glu Ala Gly Gly Ser Leu Tyr Asp Pro Val Leu Gln Lys Tyr Asp
                165                 170                 175

Glu Ile Pro Asp Leu Ser His Asn Cys Pro Leu Trp Cys Phe Arg Glu
            180                 185                 190

Ile Cys Arg His Ile Ser Gly Pro Leu Pro Asp Arg Ala Pro Tyr Leu
        195                 200                 205

Tyr Leu Ser Ala Gly Val Phe Trp Leu Met Ser Pro Arg Met Thr Ser
    210                 215                 220

Ala Ile Pro Pro Leu Leu Ser Asp Leu Val Asn Leu Ala Ile Leu Gln
225                 230                 235                 240

Gln Thr Ala Gly Leu Asp Pro Ser Leu Val Lys Leu Gly Val Gln Ile
                245                 250                 255

Cys Leu His Ala Ala Ser Ser Tyr Ala Trp Phe Ile Leu Lys
            260                 265                 270

Thr Lys Ser Ile Phe Pro Gln Asn Thr Leu His Ser Met Tyr Glu Ser
    275                 280                 285

Leu Glu Gly Gly Tyr Cys Pro Asn Leu Glu Trp Leu Glu Pro Arg Ser
    290                 295                 300

Asp Tyr Lys Phe Met Tyr Met Gly Val Met Pro Leu Ser Ala Lys Tyr
305                 310                 315                 320

Ala Arg Ser Ala Pro Ser Asn Asp Lys Lys Ala Arg Glu Leu Gly Glu
                325                 330                 335

Lys Tyr Gly Leu Ser Ser Val Val Gly Glu Leu Arg Lys Arg Thr Lys
            340                 345                 350

Thr Tyr Val Lys His Asp Phe Ala Ser Val Arg Tyr Ile Arg Asp Ala
    355                 360                 365

Met Ala Cys Thr Ser Gly Ile Phe Leu Val Arg Thr Pro Thr Glu Thr
370                 375                 380

Val Leu Gln Glu Tyr Thr Gln Ser Pro Glu Ile Lys Val Pro Ile Pro
385                 390                 395                 400

Gln Lys Asp Trp Thr Gly Pro Ile Gly Glu Ile Arg Ile Leu Lys Asp
                405                 410                 415

Thr Thr Ser Ser Ile Ala Arg Tyr Leu Tyr Arg Thr Trp Tyr Leu Ala
            420                 425                 430

Ala Ala Arg Met Ala Ala Gln Pro Arg Thr Trp Asp Pro Leu Phe Gln
    435                 440                 445

Ala Ile Met Arg Ser Gln Tyr Val Thr Ala Arg Gly Gly Ser Gly Ala
450                 455                 460

Ala Leu Arg Glu Ser Leu Tyr Ala Ile Asn Val Ser Leu Pro Asp Phe
465                 470                 475                 480

Lys Gly Leu Pro Val Lys Ala Thr Lys Ile Phe Gln Ala Ala Gln
                485                 490                 495

Leu Ala Asn Leu Pro Phe Ser His Thr Ser Val Ala Ile Leu Ala Asp
            500                 505                 510

Thr Ser Met Gly Leu Arg Asn Gln Val Gln Arg Arg Pro Arg Ser Ile
    515                 520                 525

Met Pro Leu Asn Val Pro Gln Gln Val Ser Ala Pro His Thr Leu
530                 535                 540

Thr Ala Asp Tyr Ile Asn Tyr His Met Asn Leu Ser Thr Thr Ser Gly
545                 550                 555                 560

Ser Ala Val Ile Glu Lys Val Ile Pro Leu Gly Val Tyr Ala Ser Ser
                565                 570                 575

Pro Pro Asn Gln Ser Ile Asn Ile Asp Ile Ser Ala Cys Asp Ala Ser
```

-continued

```
            580                 585                 590
Ile Thr Trp Asp Phe Phe Leu Ser Val Ile Met Ala Ala Ile His Glu
            595                 600                 605
Gly Val Ala Ser Ser Ser Ile Gly Lys Pro Phe Met Gly Val Pro Ala
            610                 615                 620
Ser Ile Val Asn Asp Glu Ser Val Val Gly Val Arg Ala Ala Arg Pro
625                 630                 635                 640
Ile Ser Gly Met Gln Asn Met Ile Gln His Leu Ser Lys Leu Tyr Lys
                    645                 650                 655
Arg Gly Phe Ser Tyr Arg Val Asn Asp Ser Phe Ser Pro Gly Asn Asp
                660                 665                 670
Phe Thr His Met Thr Thr Thr Phe Pro Ser Gly Ser Thr Ala Thr Ser
                675                 680                 685
Thr Glu His Thr Ala Asn Asn Ser Thr Met Met Glu Thr Phe Leu Thr
            690                 695                 700
Val Trp Gly Pro Glu His Thr Asp Asp Pro Asp Val Leu Arg Leu Met
705                 710                 715                 720
Lys Ser Leu Thr Ile Gln Arg Asn Tyr Val Cys Gln Gly Asp Asp Gly
                    725                 730                 735
Leu Met Ile Ile Asp Gly Thr Thr Ala Gly Lys Val Asn Ser Glu Thr
                740                 745                 750
Ile Gln Lys Met Leu Glu Leu Ile Ser Lys Tyr Gly Glu Glu Phe Gly
                755                 760                 765
Trp Lys Tyr Asp Ile Ala Tyr Asp Gly Thr Ala Glu Tyr Leu Lys Leu
        770                 775                 780
Tyr Phe Ile Phe Gly Cys Arg Ile Pro Asn Leu Ser Arg His Pro Ile
785                 790                 795                 800
Val Gly Lys Glu Arg Ala Asn Ser Ser Ala Glu Pro Trp Pro Ala
                805                 810                 815
Ile Leu Asp Gln Ile Met Gly Val Phe Phe Asn Gly Val His Asp Gly
                820                 825                 830
Leu Gln Trp Gln Arg Trp Ile Arg Tyr Ser Trp Ala Leu Cys Cys Ala
        835                 840                 845
Phe Ser Arg Gln Arg Thr Met Ile Gly Glu Ser Val Gly Tyr Leu Gln
850                 855                 860
Tyr Pro Met Trp Ser Phe Val Tyr Trp Gly Leu Pro Leu Val Lys Ala
865                 870                 875                 880
Phe Gly Ser Asp Pro Trp Ile Phe Ser Trp Tyr Met Pro Thr Gly Asp
                    885                 890                 895
Leu Gly Met Tyr Ser Trp Ile Ser Leu Ile Arg Pro Leu Met Thr Arg
                900                 905                 910
Trp Met Val Ala Asn Gly Tyr Val Thr Asp Arg Cys Ser Pro Val Phe
            915                 920                 925
Gly Asn Ala Asp Tyr Arg Arg Cys Phe Asn Glu Leu Lys Leu Tyr Gln
        930                 935                 940
Gly Tyr Tyr Met Ala Gln Leu Pro Arg Asn Pro Lys Lys Ser Gly Arg
945                 950                 955                 960
Ala Ala Pro Arg Glu Val Arg Glu Gln Phe Thr Gln Ala Leu Ser Asp
                    965                 970                 975
Tyr Leu Leu Gln Asn Pro Glu Leu Lys Ser Arg Val Leu Arg Gly Arg
                980                 985                 990
Ser Glu Trp Glu Lys Tyr Gly Ala Gly Ile Ile His Asn Pro Pro Ser
            995                 1000                1005
```

```
Leu Phe Asp Val Pro His Lys Trp Tyr Gln Gly Ala Gln Glu Ala Ala
        1010                1015                1020

Ile Ala Thr Arg Glu Glu Leu Ala Glu Met Asp Glu Thr Leu Met Arg
1025                1030                1035                1040

Ala Arg Arg His Arg Tyr Ser Ser Phe Ser Lys Leu Leu Glu Ala Tyr
            1045                1050                1055

Leu Leu Val Lys Trp Arg Met Cys Glu Ala Arg Glu Pro Ser Val Asp
        1060                1065                1070

Leu Arg Leu Pro Leu Cys Ala Gly Ile Asp Pro Leu Asn Ser Asp Pro
    1075                1080                1085

Phe Leu Lys Met Val Ser Val Gly Pro Met Leu Gln Ser Thr Arg Lys
1090                1095                1100

Tyr Phe Ala Gln Thr Leu Phe Met Ala Lys Thr Val Ser Gly Leu Asp
1105                1110                1115                1120

Val Asn Ala Ile Asp Ser Ala Leu Leu Arg Leu Arg Thr Leu Gly Ala
            1125                1130                1135

Asp Lys Lys Ala Leu Thr Ala Gln Leu Leu Met Val Gly Leu Gln Glu
        1140                1145                1150

Ser Glu Ala Asp Ala Leu Ala Gly Lys Ile Met Leu Gln Asp Val Asn
    1155                1160                1165

Thr Val Gln Leu Ala Arg Val Val Asn Leu Ala Val Pro Asp Thr Trp
    1170                1175                1180

Met Ser Leu Asp Phe Asp Ser Met Phe Lys His His Val Lys Leu Leu
1185                1190                1195                1200

Pro Lys Asp Gly Arg His Leu Asn Thr Asp Ile Pro Pro Arg Met Gly
            1205                1210                1215

Trp Leu Arg Ala Ile Leu Arg Phe Leu Gly Ala Gly Met Val Met Thr
        1220                1225                1230

Ala Thr Gly Val Ala Val Asp Ile Tyr Leu Glu Asp Ile His Gly Gly
        1235                1240                1245

Gly Arg Ser Leu Gly Gln Arg Phe Met Thr Trp Met Arg Gln Glu Gly
    1250                1255                1260

Arg Ser Ala
1265

<210> SEQ ID NO 20
<211> LENGTH: 1289
<212> TYPE: PRT
<213> ORGANISM: Reovirus

<400> SEQUENCE: 20

Met Ala Asn Val Trp Gly Val Arg Leu Ala Asp Ser Leu Ser Ser Pro
  1               5                  10                  15

Thr Ile Glu Thr Arg Thr Arg Gln Tyr Thr Leu His Asp Leu Cys Ser
            20                  25                  30

Asp Leu Asp Ala Asn Pro Gly Arg Glu Pro Trp Lys Pro Leu Arg Asn
        35                  40                  45

Gln Arg Thr Asn Asn Ile Val Ala Val Gln Leu Phe Arg Pro Leu Gln
    50                  55                  60

Gly Leu Val Leu Asp Thr Gln Leu Tyr Gly Phe Pro Gly Ala Phe Asp
65                  70                  75                  80

Asp Trp Glu Arg Phe Met Arg Glu Lys Leu Arg Val Leu Lys Tyr Glu
                85                  90                  95

Val Leu Arg Ile Tyr Pro Ile Ser Asn Tyr Ser Asn Glu His Val Asn
```

-continued

```
                100                 105                 110
Val Phe Val Ala Asn Ala Leu Val Gly Ala Phe Leu Ser Asn Gln Ala
            115                 120                 125
Phe Tyr Asp Leu Leu Pro Leu Leu Ile Ile Asn Asp Thr Met Ile Gly
130                 135                 140
Asp Leu Leu Gly Thr Gly Ala Ser Leu Ser Gln Phe Phe Gln Ser His
145                 150                 155                 160
Gly Asp Val Leu Glu Val Ala Ala Gly Arg Lys Tyr Leu Gln Met Glu
                165                 170                 175
Asn Tyr Ser Asn Asp Asp Asp Pro Pro Leu Phe Ala Lys Asp Leu
            180                 185                 190
Ser Asp Tyr Ala Lys Ala Phe Tyr Ser Asp Thr Tyr Glu Val Leu Asp
            195                 200                 205
Arg Phe Phe Trp Thr His Asp Ser Ser Ala Gly Val Leu Val His Tyr
210                 215                 220
Asp Lys Pro Thr Asn Gly His His Tyr Leu Leu Gly Thr Leu Thr Gln
225                 230                 235                 240
Met Val Ser Ala Pro Pro Tyr Ile Ile Asn Ala Thr Asp Ala Met Leu
                245                 250                 255
Leu Glu Ser Cys Leu Glu Gln Phe Ser Ala Asn Val Arg Ala Arg Pro
            260                 265                 270
Ala Gln Pro Val Thr Arg Leu Asp Gln Cys Tyr His Leu Arg Trp Gly
            275                 280                 285
Ala Gln Tyr Val Gly Glu Asp Ser Leu Thr Tyr Arg Leu Gly Val Leu
            290                 295                 300
Ser Leu Leu Ala Thr Asn Gly Tyr Gln Leu Ala Arg Pro Ile Pro Arg
305                 310                 315                 320
Gln Leu Thr Asn Arg Trp Leu Ser Ser Phe Val Ser Gln Ile Met Ser
                325                 330                 335
Asp Gly Val Asn Glu Thr Pro Leu Trp Pro Gln Glu Arg Tyr Val Gln
                340                 345                 350
Ile Ala Tyr Asp Ser Pro Ser Val Val Asp Gly Ala Thr Gln Tyr Gly
            355                 360                 365
Tyr Val Arg Lys Asn Gln Leu Arg Leu Gly Met Arg Ile Ser Ala Leu
            370                 375                 380
Gln Ser Leu Ser Asp Thr Pro Ser Pro Val Gln Trp Leu Pro Gln Tyr
385                 390                 395                 400
Thr Ile Asp Gln Ala Ala Met Asp Glu Gly Asp Leu Met Val Ser Arg
                405                 410                 415
Leu Thr Gln Leu Pro Leu Arg Pro Asp Tyr Gly Asn Ile Trp Val Gly
            420                 425                 430
Asp Ala Leu Ser Tyr Tyr Val Asp Tyr Asn Arg Ser His Arg Val Val
            435                 440                 445
Leu Ser Ser Glu Leu Pro Gln Leu Pro Asp Thr Tyr Phe Asp Gly Asp
            450                 455                 460
Glu Gln Tyr Gly Arg Ser Leu Phe Ser Leu Ala Arg Lys Ile Gly Asp
465                 470                 475                 480
Arg Ser Leu Val Lys Asp Thr Ala Val Leu Lys His Ala Tyr Gln Ala
                485                 490                 495
Ile Asp Pro Asn Thr Gly Lys Glu Tyr Leu Arg Ser Arg Gln Ser Val
            500                 505                 510
Ala Tyr Phe Gly Ala Ser Ala Gly His Ser Gly Ala Asp Gln Pro Leu
            515                 520                 525
```

-continued

```
Val Ile Glu Pro Trp Ile Gln Gly Lys Ile Ser Gly Val Pro Pro
    530                 535                 540
Ser Ser Val Arg Gln Phe Gly Tyr Asp Val Ala Arg Gly Ala Ile Val
545                 550                 555                 560
Asp Leu Ala Arg Pro Phe Pro Ser Gly Asp Tyr Gln Phe Val Tyr Ser
                565                 570                 575
Asp Val Asp Gln Val Val Asp Gly His Asp Asp Leu Ser Ile Ser Ser
            580                 585                 590
Gly Leu Val Glu Ser Leu Leu Ser Ser Cys Met His Ala Thr Ala Pro
        595                 600                 605
Gly Gly Ser Phe Val Val Lys Ile Asn Phe Pro Thr Arg Pro Val Trp
    610                 615                 620
His Tyr Ile Glu Gln Lys Ile Leu Pro Asn Ile Thr Ser Tyr Met Leu
625                 630                 635                 640
Ile Lys Pro Phe Val Thr Asn Asn Val Glu Leu Phe Phe Val Ala Phe
                645                 650                 655
Gly Val His Gln His Ser Ser Leu Thr Trp Thr Ser Gly Val Tyr Phe
            660                 665                 670
Phe Leu Val Asp His Phe Tyr Arg Tyr Glu Thr Leu Ser Thr Ile Ser
        675                 680                 685
Arg Gln Leu Pro Ser Phe Gly Tyr Val Asp Asp Gly Ser Ser Val Thr
    690                 695                 700
Gly Ile Glu Thr Ile Ser Ile Glu Asn Pro Gly Phe Ser Asn Met Thr
705                 710                 715                 720
Gln Ala Ala Arg Ile Gly Ile Ser Gly Leu Cys Ala Asn Val Gly Asn
                725                 730                 735
Ala Arg Lys Ser Ile Ala Ile Tyr Glu Ser His Gly Ala Arg Val Leu
            740                 745                 750
Thr Ile Thr Ser Arg Arg Ser Pro Ala Ser Ala Arg Arg Lys Ser Arg
        755                 760                 765
Leu Arg Tyr Leu Pro Leu Ile Asp Pro Arg Ser Leu Glu Val Gln Ala
    770                 775                 780
Arg Thr Ile Leu Pro Ala Asp Pro Val Leu Phe Glu Asn Val Ser Gly
785                 790                 795                 800
Ala Ser Pro His Val Cys Leu Thr Met Met Tyr Asn Phe Glu Val Ser
                805                 810                 815
Ser Ala Val Tyr Asp Gly Asp Val Val Leu Asp Leu Gly Thr Gly Pro
            820                 825                 830
Glu Ala Lys Ile Leu Glu Leu Ile Pro Ala Thr Ser Pro Val Thr Cys
        835                 840                 845
Val Asp Ile Arg Pro Thr Ala Gln Pro Ser Gly Cys Trp Asn Val Arg
    850                 855                 860
Thr Thr Phe Leu Glu Leu Asp Tyr Leu Ser Asp Gly Trp Ile Thr Gly
865                 870                 875                 880
Val Arg Gly Asp Ile Val Thr Cys Met Leu Ser Leu Gly Ala Ala Ala
                885                 890                 895
Ala Gly Lys Ser Met Thr Phe Asp Ala Ala Phe Gln Gln Leu Ile Lys
            900                 905                 910
Val Leu Ser Lys Ser Thr Ala Asn Val Val Leu Val Gln Val Asn Cys
        915                 920                 925
Pro Thr Asp Val Val Arg Ser Ile Lys Gly Tyr Leu Glu Ile Asp Ser
    930                 935                 940
```

-continued

Thr Asn Lys Arg Tyr Arg Phe Pro Lys Phe Gly Arg Asp Glu Pro Tyr
945                 950                 955                 960

Ser Asp Met Asp Ala Leu Glu Lys Ile Cys Arg Thr Ala Trp Pro Asn
            965                 970                 975

Cys Ser Ile Thr Trp Val Pro Leu Ser Tyr Asp Leu Arg Trp Thr Arg
            980                 985                 990

Leu Ala Leu Leu Glu Ser Thr Thr Leu Ser Ser Ala Ser Ile Arg Ile
            995                 1000                1005

Ala Glu Leu Met Tyr Lys Tyr Met Pro Ile Met Arg Ile Asp Ile His
        1010                1015                1020

Gly Leu Pro Met Glu Lys Arg Gly Asn Phe Ile Val Gly Gln Asn Cys
1025                1030                1035                1040

Ser Leu Val Ile Pro Gly Phe Asn Ala Gln Asp Val Phe Asn Cys Tyr
                1045                1050                1055

Phe Asn Ser Ala Leu Ala Phe Ser Thr Glu Asp Val Asn Ala Ala Met
                1060                1065                1070

Ile Pro Gln Val Ser Ala Gln Phe Asp Ala Thr Lys Gly Glu Trp Thr
            1075                1080                1085

Leu Asp Met Val Phe Ser Asp Ala Gly Ile Tyr Thr Met Gln Ala Leu
        1090                1095                1100

Val Gly Ser Asn Ala Asn Pro Val Ser Leu Gly Ser Phe Val Val Asp
1105                1110                1115                1120

Ser Pro Asp Val Asp Ile Thr Asp Ala Trp Pro Ala Gln Leu Asp Phe
                1125                1130                1135

Thr Ile Ala Gly Thr Asp Val Asp Ile Thr Val Asn Pro Tyr Tyr Arg
            1140                1145                1150

Leu Met Thr Phe Val Arg Ile Asp Gly Gln Trp Gln Ile Ala Asn Pro
        1155                1160                1165

Asp Lys Phe Gln Phe Phe Ser Ser Ala Ser Gly Thr Leu Val Met Asn
        1170                1175                1180

Val Lys Leu Asp Ile Ala Asp Lys Tyr Leu Leu Tyr Ile Arg Asp
1185                1190                1195                1200

Val Gln Ser Arg Asp Val Gly Phe Tyr Ile Gln His Pro Leu Gln Leu
            1205                1210                1215

Leu Asn Thr Ile Thr Leu Pro Thr Asn Glu Asp Leu Phe Leu Ser Ala
            1220                1225                1230

Pro Asp Met Arg Glu Trp Ala Val Lys Glu Ser Gly Asn Thr Ile Cys
        1235                1240                1245

Ile Leu Asn Ser Gln Gly Phe Val Leu Pro Gln Asp Trp Asp Val Leu
        1250                1255                1260

Thr Asp Thr Ile Ser Trp Ser Pro Ser Ile Pro Thr Tyr Ile Val Pro
1265                1270                1275                1280

Pro Gly Asp Tyr Thr Leu Thr Pro Leu
                1285

<210> SEQ ID NO 21
<211> LENGTH: 1275
<212> TYPE: PRT
<213> ORGANISM: Reovirus

<400> SEQUENCE: 21

Met Lys Arg Ile Pro Arg Lys Thr Lys Gly Lys Ser Ser Gly Lys Gly
1               5                   10                  15

Asn Asp Ser Thr Glu Arg Ala Asp Gly Ser Ser Gln Leu Arg Asp
            20                  25                  30

-continued

Lys Gln Asn Asn Lys Ala Gly Pro Ala Thr Thr Glu Pro Gly Thr Ser
                35                  40                  45

Asn Arg Glu Gln Tyr Lys Ala Arg Pro Gly Ile Ala Ser Val Gln Arg
 50                  55                  60

Ala Thr Glu Ser Ala Glu Met Pro Met Lys Asn Asn Asp Glu Gly Thr
 65                  70                  75                  80

Pro Asp Lys Lys Gly Asn Thr Lys Gly Asp Leu Val Asn Glu His Ser
                85                  90                  95

Glu Ala Lys Asp Glu Ala Asp Glu Ala Thr Lys Lys Gln Ala Lys Asp
                100                 105                 110

Thr Asp Lys Ser Lys Ala Gln Val Thr Tyr Ser Asp Thr Gly Ile Asn
                115                 120                 125

Asn Ala Asn Glu Leu Ser Arg Ser Gly Asn Val Asp Asn Glu Gly Gly
    130                 135                 140

Ser Asn Gln Lys Pro Met Ser Thr Arg Ile Ala Glu Ala Thr Ser Ala
145                 150                 155                 160

Ile Val Ser Lys His Pro Ala Arg Val Gly Leu Pro Pro Thr Ala Ser
                165                 170                 175

Ser Gly His Gly Tyr Gln Cys His Val Cys Ser Ala Val Leu Phe Ser
                180                 185                 190

Pro Leu Asp Leu Asp Ala His Val Ala Ser His Gly Leu His Gly Asn
                195                 200                 205

Met Thr Leu Thr Ser Ser Asp Ile Gln Arg His Ile Thr Glu Phe Ile
    210                 215                 220

Ser Ser Trp Gln Asn His Pro Ile Val Gln Val Ser Ala Asp Val Glu
225                 230                 235                 240

Asn Lys Lys Thr Ala Gln Leu Leu His Ala Asp Thr Pro Arg Leu Val
                245                 250                 255

Thr Trp Asp Ala Gly Leu Cys Thr Ser Phe Lys Ile Val Pro Ile Val
                260                 265                 270

Pro Ala Gln Val Pro Gln Asp Val Leu Ala Tyr Thr Phe Phe Thr Ser
                275                 280                 285

Ser Tyr Ala Ile Gln Ser Pro Phe Pro Glu Ala Ala Val Ser Arg Ile
    290                 295                 300

Val Val His Thr Arg Trp Ala Ser Asn Val Asp Phe Asp Arg Asp Ser
305                 310                 315                 320

Ser Val Ile Met Ala Pro Pro Thr Glu Asn Asn Ile His Leu Phe Lys
                325                 330                 335

Gln Leu Leu Asn Thr Glu Thr Leu Ser Val Arg Gly Ala Asn Pro Leu
                340                 345                 350

Met Phe Arg Ala Asn Val Leu His Met Leu Leu Glu Phe Val Leu Asp
                355                 360                 365

Asn Leu Tyr Leu Asn Arg His Thr Gly Phe Ser Gln Asp His Thr Pro
    370                 375                 380

Phe Thr Glu Gly Ala Asn Leu Arg Ser Leu Pro Gly Pro Asp Ala Glu
385                 390                 395                 400

Lys Trp Tyr Ser Ile Met Tyr Pro Thr Arg Met Gly Thr Pro Asn Val
                405                 410                 415

Ser Lys Ile Cys Asn Phe Val Ala Ser Cys Val Arg Asn Arg Val Gly
                420                 425                 430

Arg Phe Asp Arg Ala Gln Met Met Asn Gly Ala Met Ser Glu Trp Val
    435                 440                 445

-continued

```
Asp Val Phe Glu Thr Ser Asp Ala Leu Thr Val Ser Ile Arg Gly Arg
    450                 455                 460

Trp Met Ala Arg Leu Ala Arg Met Asn Ile Asn Pro Thr Glu Ile Glu
465                 470                 475                 480

Trp Ala Leu Thr Glu Cys Ala Gln Gly Tyr Val Thr Val Thr Ser Pro
                485                 490                 495

Tyr Ala Pro Ser Val Asn Arg Leu Met Pro Tyr Arg Ile Ser Asn Ala
                500                 505                 510

Glu Arg Gln Ile Ser Gln Ile Ile Arg Ile Met Asn Ile Gly Asn Asn
                515                 520                 525

Ala Thr Val Ile Gln Pro Val Leu Gln Asp Ile Ser Val Leu Leu Gln
    530                 535                 540

Arg Ile Ser Pro Leu Gln Ile Asp Pro Thr Ile Ile Ser Asn Thr Met
545                 550                 555                 560

Ser Thr Val Ser Glu Ser Thr Thr Gln Thr Leu Ser Pro Ala Ser Ser
                565                 570                 575

Ile Leu Gly Lys Leu Arg Pro Ser Asn Ser Asp Phe Ser Ser Phe Arg
                580                 585                 590

Val Ala Leu Ala Gly Trp Leu Tyr Asn Gly Val Val Thr Thr Val Ile
                595                 600                 605

Asp Asp Ser Ser Tyr Pro Lys Asp Gly Gly Ser Val Thr Ser Leu Glu
    610                 615                 620

Asn Leu Trp Asp Phe Phe Ile Leu Ala Leu Ala Leu Pro Leu Thr Thr
625                 630                 635                 640

Asp Pro Cys Ala Pro Val Lys Ala Phe Met Thr Leu Ala Asn Met Met
                645                 650                 655

Val Gly Phe Glu Thr Ile Pro Met Asp Asn Gln Ile Tyr Thr Gln Ser
                660                 665                 670

Arg Arg Ala Ser Ala Phe Ser Thr Pro His Thr Trp Pro Arg Cys Phe
    675                 680                 685

Met Asn Ile Gln Leu Ile Ser Pro Ile Asp Ala Pro Ile Leu Arg Gln
690                 695                 700

Trp Ala Glu Ile Ile His Arg Tyr Trp Pro Asn Pro Ser Gln Ile Arg
705                 710                 715                 720

Tyr Gly Ala Pro Asn Val Phe Gly Ser Ala Asn Leu Phe Thr Pro Pro
                725                 730                 735

Glu Val Leu Leu Leu Pro Ile Asp His Gln Pro Ala Asn Val Thr Thr
                740                 745                 750

Pro Thr Leu Asp Phe Thr Asn Glu Leu Thr Asn Trp Arg Ala Arg Val
    755                 760                 765

Cys Glu Leu Met Lys Asn Leu Val Asp Asn Gln Arg Tyr Gln Pro Gly
770                 775                 780

Trp Thr Gln Ser Leu Val Ser Ser Met Arg Gly Thr Leu Asp Lys Leu
785                 790                 795                 800

Lys Leu Ile Lys Ser Met Thr Pro Met Tyr Leu Gln Gln Leu Ala Pro
                805                 810                 815

Val Glu Leu Ala Val Ile Ala Pro Met Leu Pro Phe Pro Pro Phe Gln
                820                 825                 830

Val Pro Tyr Val Arg Leu Asp Arg Asp Arg Val Pro Thr Met Val Gly
                835                 840                 845

Val Thr Arg His Ser Arg Asp Thr Ile Thr Gln Pro Ala Leu Ser Leu
    850                 855                 860

Ser Thr Thr Asn Thr Thr Val Gly Val Pro Leu Ala Leu Asp Ala Arg
```

-continued

```
                865                 870                 875                 880
Ala Ile Thr Val Ala Leu Leu Ser Gly Lys Tyr Pro Pro Asp Leu Val
                    885                 890                 895

Thr Asn Val Trp Tyr Ala Asp Ala Ile Tyr Pro Met Tyr Ala Asp Thr
                900                 905                 910

Glu Val Phe Ser Asn Leu Gln Arg Asp Met Ile Thr Cys Glu Ala Val
                915                 920                 925

Gln Thr Leu Val Thr Leu Val Ala Gln Ile Ser Glu Thr Gln Tyr Pro
                930                 935                 940

Val Asp Arg Tyr Leu Asp Trp Ile Pro Ser Leu Arg Ala Ser Ala Ala
945                 950                 955                 960

Thr Ala Ala Thr Phe Ala Glu Trp Val Asn Thr Ser Met Lys Thr Ala
                965                 970                 975

Phe Asp Leu Ser Asp Met Leu Leu Glu Pro Leu Leu Ser Gly Asp Pro
                980                 985                 990

Arg Met Thr Gln Leu Ala Ile Gln Tyr Gln Tyr Asn Gly Arg Thr
                995                 1000                1005

Phe Asn Ile Ile Pro Glu Met Pro Gly Ser Val Ile Ala Asp Cys Val
1010                1015                1020

Gln Leu Thr Ala Glu Val Phe Asn His Glu Tyr Asn Leu Phe Gly Ile
1025                1030                1035                1040

Ala Arg Gly Asp Ile Ile Ile Gly Arg Val Gln Ser Thr His Leu Trp
                1045                1050                1055

Ser Pro Leu Ala Pro Pro Asp Leu Val Phe Asp Arg Asp Thr Pro
                1060                1065                1070

Gly Val His Ile Phe Gly Arg Asp Cys Arg Ile Ser Phe Gly Met Asn
                1075                1080                1085

Gly Ala Ala Pro Met Ile Arg Asp Glu Thr Gly Leu Met Val Pro Phe
1090                1095                1100

Glu Gly Asn Trp Ile Phe Pro Leu Ala Leu Trp Gln Met Asn Thr Arg
1105                1110                1115                1120

Tyr Phe Asn Gln Gln Phe Asp Ala Trp Ile Lys Thr Gly Glu Leu Arg
                1125                1130                1135

Ile Arg Ile Glu Met Gly Ala Tyr Pro Tyr Met Leu His Tyr Tyr Asp
                1140                1145                1150

Pro Arg Gln Tyr Ala Asn Ala Trp Asn Leu Thr Ser Ala Trp Leu Glu
                1155                1160                1165

Glu Ile Thr Pro Thr Ser Ile Pro Ser Val Pro Phe Met Val Pro Ile
                1170                1175                1180

Ser Ser Asp His Asp Ile Ser Ser Ala Pro Ala Val Gln Tyr Ile Ile
1185                1190                1195                1200

Ser Thr Glu Tyr Asn Asp Arg Ser Leu Phe Cys Thr Asn Ser Ser Ser
                1205                1210                1215

Pro Gln Thr Ile Ala Gly Pro Asp Lys His Ile Pro Val Glu Arg Tyr
                1220                1225                1230

Asn Ile Leu Thr Asn Pro Asp Ala Pro Pro Thr Gln Ile Gln Leu Pro
                1235                1240                1245

Glu Val Val Asp Leu Tyr Asn Val Val Thr Arg Tyr Ala Tyr Glu Thr
                1250                1255                1260

Pro Pro Ile Thr Ala Val Val Met Gly Val Pro
1265                1270                1275

<210> SEQ ID NO 22
```

<211> LENGTH: 3854
<212> TYPE: DNA
<213> ORGANISM: Reovirus

<400> SEQUENCE: 22

```
gctacacgtt ccacgacaat gtcatccatg atactgactc agtttggacc gttcattgag     60
agcatttcag gtatcactga tcaatcgaat gacgtgtttg aagatgcagc aaaagcattc    120
tctatgttta ctcgcagcga tgtctacaag gcgctggatg aaataccttt ctctgatgat    180
gcgatgcttc caatccctcc aactatatat acgaaaccat ctcacgattc atattattac    240
attgatgctc taaaccgtgt gcgtcgcaaa acatatcagg gccctgatga cgtgtacgta    300
cctaattgtt ctattgttga attgctggag ccacatgaga ctctgacatc ttatgggcgg    360
ttgtccgagg ccatcgagaa tcgtgccaag gatgggacag ccaagccag aatcgccaca    420
acgtatggta gaatcgctga atctcaagct cgacagatta aggctccatt ggagaagttt    480
gtgttggcac tattagtggc cgaagcaggg gggtctttat atgatccagt tttgcagaag    540
tatgatgaga ttccagatct atcgcataat tgccctttat ggtgttttag agagatctgt    600
cgtcacatat ctggtccatt accagatcgg gcaccttatc tttacttatc tgcaggggta    660
ttctggttaa tgtcaccacg aatgacgtct gcaatccctc cgctactatc cgatcttgtt    720
aatttagcta ttttgcaaca aactgcgggt ttagatccat cattagtgaa attgggagta    780
cagatatgcc ttcatgcagc agctagctca agttattcat ggtttatctt aaagactaag    840
tctattttc ctcaaaacac gttgcacagt atgtatgaat ctctagaagg gggatactgt    900
cctaatcttg aatggttaga gcctagatca gactataagt tcatgtacat gggagtcatg    960
ccattgtccg ctaagtatgc taggtcggcg ccgtccaatg ataagaaagc gcgggaactt   1020
ggcgagaaat atggactgag ctcagtcgtc ggtgagcttc gtaaacggac aaagacgtat   1080
gttaaacatg actttgcttc agtgaggtac attcgtgacg ctatggcatg tactagcggt   1140
attttcttgg taagaacacc caccgaaacg gtattgcaag aatatacgca gagtccggag   1200
attaaggttc ccattcccca gaaagactgg acaggcccaa taggtgaaat cagaattcta   1260
aaagatacaa caagttccat cgcgcgttac ttatatagaa catggtactt ggcagcggcg   1320
agaatggcgg ctcaaccacg tacgtgggat ccattgtttc aagcgattat gagatctcaa   1380
tacgtgacag ctaggggtgg atctggcgca gcactccgcg aatctttgta tgcaatcaat   1440
gtgtcgttac ctgatttcaa gggcttacca gtgaaggcag caactaagat attccaggcg   1500
gcacaattag cgaacttgcc gttctcccac acatcagtgg ctatactagc tgacacttca   1560
atgggattgc gaaatcaggt gcagaggcgg ccacgatcca ttatgccatt aaatgtgccc   1620
cagcagcagg tttcggcgcc ccatacattg acagcggatt acattaacta ccacatgaat   1680
ctatcaccca gtctggtag tgcggtcatt gagaaggtga ttcctttagg tgtatacgct   1740
tcgagccctc ctaaccagtc gatcaacatt gacatatctg cgtgtgacgc tagtattact   1800
tgggatttct ttctgtcagt gattatggcg gctatacacg aaggtgtcgc tagtagctcc   1860
attggaaaac catttatggg ggttcctgca tccattgtaa atgatgagtc tgtcgttgga   1920
gtgagagctg ctaggccgat atcgggaatg cagaacatga ttcagcatct atcgaaacta   1980
tataaacgtg gattttcata tagagtaaac gattctttt ctccaggtaa cgattttact   2040
catatgacta ccactttccc gtcaggttca acagccacct ctactgagca tactgctaat   2100
aatagtacga tgatgaaaac tttcctgaca gtatggggac ccgaacatac tgacgaccct   2160
gacgtcttac gtttaatgaa gtctttaact attcaaagga attacgtatg tcaaggtgat   2220
```

-continued

```
gatggattaa tgattatcga tgggactact gctggtaagg tgaacagtga aactattcag    2280
aacgatctag aattaatctc aaaatatggt gaggaattcg gatggaaata tgacatagcg    2340
tacgatggga ctgccgaata cttaaagcta tacttcatat ttggctgtcg aattccaaat    2400
cttagtcgcc atccaatcgt ggggaaagaa cgggcgaatt cttcagcaga ggagccatgg    2460
ccagcaattc tagatcagat tatgggtgtc ttctttaatg tgttcatga tgggttacag     2520 tggcagcggt ggatacgtta ttcatgggct ctatgctgtg ctttctcacg tcaaagaaca    2580
atgattggtg agagcgtggg ttaccttcaa atcctatgt ggtcttttgt ctactgggga    2640
ttaccactgg ttaaagcgtt tgggtcagac ccatggatat tttcttggta catgcctact    2700
ggagatctgg gaatgtatag ttggattagc ttgatacgcc ctctgatgac aagatggatg    2760
gtggctaatg gttacgtaac tgacagatgc tcaaccgtat tcgggaacgc agattatcgc    2820
aggtgtttca atgaacttaa actatatcaa ggttattata tggcacaatt gcccaggaat    2880
cctaagaagt ctggacgagc ggcctctcgg gaggtaagag aacaattcac tcaggcatta    2940
tccgactatc taatgcaaaa tccagagctg aagtcacgtg tgctacgtgg tcgtagtgag    3000
tgggagaaat atggagcggg gataattcac aatcctccgt cattattcga tgtgccccat    3060
aaatggtatc agggtgcgca agaggcagca atcgctacga gaagagct ggcagaaatg     3120 gatgagacat taatgcgcgc tcgaaggcac agctattcga gcttttcaaa gttattagag    3180
gcgtatctgc tcgtgaaatg gcgaatgtgc gaggcccgcg aaccgtcggt tgatttgcga    3240
ttaccattat gtgcgggtat tgacccatta aactcagatc ctttctcaa gatggtaagc     3300 gttggaccaa tgctccagag tacgagaaag tactttgctc agacactatt catggcaaag    3360
acggtgtcgg tcttgacgt taacgcgatt gatagcgcgt tattacgact gcgaacatta    3420
ggtgctgata agaaagcatt aacggcgcag ttattaatgg tggggcttca ggagtcagaa    3480
gcggacgcat tggccgggaa gataatgcta caggatgtga atactgtgca attagccaga    3540
gtggttaact tagctgtgcc agatacttgg atgtcgttag actttgactc tatgttcaaa    3600
caccacgtca agctgcttcc caaagatgga cgtcatctaa atactgatat tcctcctcga    3660
atgggatggt tacgggccat tttacgattc ttaggtgccg aatggtaat gactgcgact     3720 ggagttgctg tcgacatcta tctggaggat atacatggcg tggtcggtc acttggacag    3780 agattcatga cttggatgcg acaggaagga cggtcagcgt gagtctacca tgggtcgtgg    3840
tgcgtcaact catc                                                      3854
```

<210> SEQ ID NO 23
<211> LENGTH: 1267
<212> TYPE: PRT
<213> ORGANISM: Reovirus

<400> SEQUENCE: 23

```
Met Ser Ser Met Ile Leu Thr Gln Phe Gly Pro Phe Ile Glu Ser Ile
  1               5                  10                  15

Ser Gly Ile Thr Asp Gln Ser Asn Asp Val Phe Glu Asp Ala Ala Lys
             20                  25                  30

Ala Phe Ser Met Phe Thr Arg Ser Asp Val Tyr Lys Ala Leu Asp Glu
         35                  40                  45

Ile Pro Phe Ser Asp Asp Ala Met Leu Pro Ile Pro Thr Ile Tyr
     50                  55                  60

Thr Lys Pro Ser His Asp Ser Tyr Tyr Tyr Ile Asp Ala Leu Asn Arg
 65                  70                  75                  80
```

-continued

```
Val Arg Arg Lys Thr Tyr Gln Gly Pro Asp Asp Val Tyr Val Pro Asn
                85                  90                  95
Cys Ser Ile Val Glu Leu Leu Glu Pro His Glu Thr Leu Thr Ser Tyr
            100                 105                 110
Gly Arg Leu Ser Glu Ala Ile Glu Asn Arg Ala Lys Asp Gly Asp Ser
        115                 120                 125
Gln Ala Arg Ile Ala Thr Thr Tyr Gly Arg Ile Ala Glu Ser Gln Ala
    130                 135                 140
Arg Gln Ile Lys Ala Pro Leu Glu Lys Phe Val Leu Ala Leu Leu Val
145                 150                 155                 160
Ala Glu Ala Gly Gly Ser Leu Tyr Asp Pro Val Leu Gln Lys Tyr Asp
                165                 170                 175
Glu Ile Pro Asp Leu Ser His Asn Cys Pro Leu Trp Cys Phe Arg Glu
            180                 185                 190
Ile Cys Arg His Ile Ser Gly Pro Leu Pro Asp Arg Ala Pro Tyr Leu
        195                 200                 205
Tyr Leu Ser Ala Gly Val Phe Trp Leu Met Ser Pro Arg Met Thr Ser
    210                 215                 220
Ala Ile Pro Pro Leu Leu Ser Asp Leu Val Asn Leu Ala Ile Leu Gln
225                 230                 235                 240
Gln Thr Ala Gly Leu Asp Pro Ser Leu Val Lys Leu Gly Val Gln Ile
                245                 250                 255
Cys Leu His Ala Ala Ala Ser Ser Tyr Ser Trp Phe Ile Leu Lys
            260                 265                 270
Thr Lys Ser Ile Phe Pro Gln Asn Thr Leu His Ser Met Tyr Glu Ser
        275                 280                 285
Leu Glu Gly Gly Tyr Cys Pro Asn Leu Glu Trp Leu Glu Pro Arg Ser
    290                 295                 300
Asp Tyr Lys Phe Met Tyr Met Gly Val Met Pro Leu Ser Ala Lys Tyr
305                 310                 315                 320
Ala Arg Ser Ala Pro Ser Asn Asp Lys Lys Ala Arg Glu Leu Gly Glu
                325                 330                 335
Lys Tyr Gly Leu Ser Ser Val Val Gly Glu Leu Arg Lys Arg Thr Lys
            340                 345                 350
Thr Tyr Val Lys His Asp Phe Ala Ser Val Arg Tyr Ile Arg Asp Ala
        355                 360                 365
Met Ala Cys Thr Ser Gly Ile Phe Leu Val Arg Thr Pro Thr Glu Thr
    370                 375                 380
Val Leu Gln Glu Tyr Thr Gln Ser Pro Glu Ile Lys Val Pro Ile Pro
385                 390                 395                 400
Gln Lys Asp Trp Thr Gly Pro Ile Gly Glu Ile Arg Ile Leu Lys Asp
                405                 410                 415
Thr Thr Ser Ser Ile Ala Arg Tyr Leu Tyr Arg Thr Trp Tyr Leu Ala
            420                 425                 430
Ala Ala Arg Met Ala Ala Gln Pro Arg Thr Trp Asp Pro Leu Phe Gln
        435                 440                 445
Ala Ile Met Arg Ser Gln Tyr Val Thr Ala Arg Gly Gly Ser Gly Ala
    450                 455                 460
Ala Leu Arg Glu Ser Leu Tyr Ala Ile Asn Val Ser Leu Pro Asp Phe
465                 470                 475                 480
Lys Gly Leu Pro Val Lys Ala Ala Thr Lys Ile Phe Gln Ala Ala Gln
                485                 490                 495
```

-continued

```
Leu Ala Asn Leu Pro Phe Ser His Thr Ser Val Ala Ile Leu Ala Asp
            500                 505                 510
Thr Ser Met Gly Leu Arg Asn Gln Val Gln Arg Arg Pro Arg Ser Ile
        515                 520                 525
Met Pro Leu Asn Val Pro Gln Gln Gln Val Ser Ala Pro His Thr Leu
    530                 535                 540
Thr Ala Asp Tyr Ile Asn Tyr His Met Asn Leu Ser Pro Thr Ser Gly
545                 550                 555                 560
Ser Ala Val Ile Glu Lys Val Ile Pro Leu Gly Val Tyr Ala Ser Ser
                565                 570                 575
Pro Pro Asn Gln Ser Ile Asn Ile Asp Ile Ser Ala Cys Asp Ala Ser
            580                 585                 590
Ile Thr Trp Asp Phe Phe Leu Ser Val Ile Met Ala Ala Ile His Glu
        595                 600                 605
Gly Val Ala Ser Ser Ser Ile Gly Lys Pro Phe Met Gly Val Pro Ala
    610                 615                 620
Ser Ile Val Asn Asp Glu Ser Val Val Gly Val Arg Ala Ala Arg Pro
625                 630                 635                 640
Ile Ser Gly Met Gln Asn Met Ile Gln His Leu Ser Lys Leu Tyr Lys
                645                 650                 655
Arg Gly Phe Ser Tyr Arg Val Asn Asp Ser Phe Ser Pro Gly Asn Asp
            660                 665                 670
Phe Thr His Met Thr Thr Thr Phe Pro Ser Gly Ser Thr Ala Thr Ser
        675                 680                 685
Thr Glu His Thr Ala Asn Asn Ser Thr Met Met Glu Thr Phe Leu Thr
    690                 695                 700
Val Trp Gly Pro Glu His Thr Asp Asp Pro Asp Val Leu Arg Leu Met
705                 710                 715                 720
Lys Ser Leu Thr Ile Gln Arg Asn Tyr Val Cys Gln Gly Asp Asp Gly
                725                 730                 735
Leu Met Ile Ile Asp Gly Thr Thr Ala Gly Lys Val Asn Ser Glu Thr
            740                 745                 750
Ile Gln Asn Asp Leu Glu Leu Ile Ser Lys Tyr Gly Glu Glu Phe Gly
        755                 760                 765
Trp Lys Tyr Asp Ile Ala Tyr Asp Gly Thr Ala Glu Tyr Leu Lys Leu
    770                 775                 780
Tyr Phe Ile Phe Gly Cys Arg Ile Pro Asn Leu Ser Arg His Pro Ile
785                 790                 795                 800
Val Gly Lys Glu Arg Ala Asn Ser Ser Ala Glu Pro Trp Pro Ala
                805                 810                 815
Ile Leu Asp Gln Ile Met Gly Val Phe Phe Asn Gly Val His Asp Gly
            820                 825                 830
Leu Gln Trp Gln Arg Trp Ile Arg Tyr Ser Trp Ala Leu Cys Cys Ala
        835                 840                 845
Phe Ser Arg Gln Arg Thr Met Ile Gly Glu Ser Val Gly Tyr Leu Gln
    850                 855                 860
Tyr Pro Met Trp Ser Phe Val Tyr Trp Gly Leu Pro Leu Val Lys Ala
865                 870                 875                 880
Phe Gly Ser Asp Pro Trp Ile Phe Ser Trp Tyr Met Pro Thr Gly Asp
                885                 890                 895
Leu Gly Met Tyr Ser Trp Ile Ser Leu Ile Arg Pro Leu Met Thr Arg
            900                 905                 910
Trp Met Val Ala Asn Gly Tyr Val Thr Asp Arg Cys Ser Thr Val Phe
```

```
                915                 920                 925
Gly Asn Ala Asp Tyr Arg Arg Cys Phe Asn Glu Leu Lys Leu Tyr Gln
        930                 935                 940

Gly Tyr Tyr Met Ala Gln Leu Pro Arg Asn Pro Lys Lys Ser Gly Arg
945                 950                 955                 960

Ala Ala Ser Arg Glu Val Arg Glu Gln Phe Thr Gln Ala Leu Ser Asp
                965                 970                 975

Tyr Leu Met Gln Asn Pro Glu Leu Lys Ser Arg Val Leu Arg Gly Arg
            980                 985                 990

Ser Glu Trp Glu Lys Tyr Gly Ala Gly Ile Ile His Asn Pro Pro Ser
        995                 1000                1005

Leu Phe Asp Val Pro His Lys Trp Tyr Gln Gly Ala Gln Glu Ala Ala
    1010                1015                1020

Ile Ala Thr Arg Glu Glu Leu Ala Glu Met Asp Glu Thr Leu Met Arg
1025                1030                1035                1040

Ala Arg Arg His Ser Tyr Ser Ser Phe Ser Lys Leu Leu Glu Ala Tyr
                1045                1050                1055

Leu Leu Val Lys Trp Arg Met Cys Glu Ala Arg Glu Pro Ser Val Asp
            1060                1065                1070

Leu Arg Leu Pro Leu Cys Ala Gly Ile Asp Pro Leu Asn Ser Asp Pro
        1075                1080                1085

Phe Leu Lys Met Val Ser Val Gly Pro Met Leu Gln Ser Thr Arg Lys
    1090                1095                1100

Tyr Phe Ala Gln Thr Leu Phe Met Ala Lys Thr Val Ser Gly Leu Asp
1105                1110                1115                1120

Val Asn Ala Ile Asp Ser Ala Leu Leu Arg Leu Arg Thr Leu Gly Ala
                1125                1130                1135

Asp Lys Lys Ala Leu Thr Ala Gln Leu Leu Met Val Gly Leu Gln Glu
            1140                1145                1150

Ser Glu Ala Asp Ala Leu Ala Gly Lys Ile Met Leu Gln Asp Val Asn
        1155                1160                1165

Thr Val Gln Leu Ala Arg Val Val Asn Leu Ala Val Pro Asp Thr Trp
    1170                1175                1180

Met Ser Leu Asp Phe Asp Ser Met Phe Lys His His Val Lys Leu Leu
1185                1190                1195                1200

Pro Lys Asp Gly Arg His Leu Asn Thr Asp Ile Pro Pro Arg Met Gly
                1205                1210                1215

Trp Leu Arg Ala Ile Leu Arg Phe Leu Gly Ala Gly Met Val Met Thr
            1220                1225                1230

Ala Thr Gly Val Ala Val Asp Ile Tyr Leu Glu Asp Ile His Gly Gly
        1235                1240                1245

Gly Arg Ser Leu Gly Gln Arg Phe Met Thr Trp Met Arg Gln Glu Gly
    1250                1255                1260

Arg Ser Ala
1265

<210> SEQ ID NO 24
<211> LENGTH: 1196
<212> TYPE: DNA
<213> ORGANISM: Reovirus

<400> SEQUENCE: 24
gctatttttg cctcttccca gacgttgtcg caatggaggt gtgcttgccc aacggtcatc    60
aggtcgtgga cttgattaac aacgcttttg aaggtcgtgt atcaatctac agcgcgcaag   120
```

```
agggatggga caaacaatc tcagcacagc cagatatgat ggtatgtggt ggcgccgtcg    180
tttgcatgca ttgtctaggt gttgttggat ctctacaacg caagctgaag catttgcctc    240
accatagatg taatcaacag atccgtcatc aggattacgt cgatgtacag ttcgcagacc    300
gtgttactgc tcactggaag cggggtatgc tgtccttcgt tgcgcagatg cacgagatga    360
tgaatgacgt gtcgccagat gacctggatc gtgtgcgtac tgaggaggt tcactagtgg    420 agctgaaccg gcttcaggtt gacccaaatt caatgtttag atcaatacac tcaagttgga    480
cagatccttt gcaggtggtg gacgaccttg acactaagct ggatcagtac tggacagcct    540
taaacctgat gatcgactca tccgacttga tacccaactt tatgatgaga gacccatcac    600
acgcgttcaa tggtgtgaaa ctggagggag atgctcgtca aacccaattc tccaggactt    660
ttgattcgag atcgagtttg aatgggggtg tgatggttta tgattactct gagctggagc    720
atgatccatc gaagggccgt gcttacagaa aggaattggt gacgccagct cgagatttcg    780
gtcactttgg attatcccat tattctaggg cgactacccc aatccttgga agatgccgg    840 ccgtattctc aggaatgttg actgggaact gtaaaatgta tccattcatt aaaggaacgg    900
ctaagctgaa gacagtgcgc aagctagtgg aggcagtcaa tcatgcttgg ggtgtcgaga    960
agattagata tgctcttggg ccaggtggca tgacgggatg gtacaatagg actatgcaac    1020 aggccccat tgtgctaact cctgctgctc tcacaatgtt cccagatacc atcaagtttg    1080
gggatttgaa ttatccagtg atgattggcg atccgatgat tcttggctaa caccccccat    1140
cttcacagcg ccgggcttga ccaacctggt gtgacgtggg acaggcttca ttcatc    1196
```

<210> SEQ ID NO 25
<211> LENGTH: 365
<212> TYPE: PRT
<213> ORGANISM: Reovirus

<400> SEQUENCE: 25

```
Met Glu Val Cys Leu Pro Asn Gly His Gln Val Val Asp Leu Ile Asn
 1               5                  10                  15

Asn Ala Phe Glu Gly Arg Val Ser Ile Tyr Ser Ala Gln Glu Gly Trp
            20                  25                  30

Asp Lys Thr Ile Ser Ala Gln Pro Asp Met Met Val Cys Gly Gly Ala
        35                  40                  45

Val Val Cys Met His Cys Leu Gly Val Val Gly Ser Leu Gln Arg Lys
    50                  55                  60

Leu Lys His Leu Pro His His Arg Cys Asn Gln Gln Ile Arg His Gln
65                  70                  75                  80

Asp Tyr Val Asp Val Gln Phe Ala Asp Arg Val Thr Ala His Trp Lys
                85                  90                  95

Arg Gly Met Leu Ser Phe Val Ala Gln Met His Glu Met Met Asn Asp
            100                 105                 110

Val Ser Pro Asp Asp Leu Asp Arg Val Arg Thr Glu Gly Gly Ser Leu
        115                 120                 125

Val Glu Leu Asn Arg Leu Gln Val Asp Pro Asn Ser Met Phe Arg Ser
    130                 135                 140

Ile His Ser Ser Trp Thr Asp Pro Leu Gln Val Val Asp Asp Leu Asp
145                 150                 155                 160

Thr Lys Leu Asp Gln Tyr Trp Thr Ala Leu Asn Leu Met Ile Asp Ser
                165                 170                 175

Ser Asp Leu Ile Pro Asn Phe Met Met Arg Asp Pro Ser His Ala Phe
```

```
                180             185             190
Asn Gly Val Lys Leu Glu Gly Asp Ala Arg Gln Thr Gln Phe Ser Arg
            195                 200                 205

Thr Phe Asp Ser Arg Ser Ser Leu Glu Trp Gly Val Met Val Tyr Asp
        210                 215                 220

Tyr Ser Glu Leu Glu His Asp Pro Ser Lys Gly Arg Ala Tyr Arg Lys
225                 230                 235                 240

Glu Leu Val Thr Pro Ala Arg Asp Phe Gly His Gly Leu Ser His
                245                 250                 255

Tyr Ser Arg Ala Thr Thr Pro Ile Leu Gly Lys Met Pro Ala Val Phe
            260                 265                 270

Ser Gly Met Leu Thr Gly Asn Cys Lys Met Tyr Pro Phe Ile Lys Gly
                275                 280                 285

Thr Ala Lys Leu Lys Thr Val Arg Lys Leu Val Glu Ala Val Asn His
        290                 295                 300

Ala Trp Gly Val Glu Lys Ile Arg Tyr Ala Leu Gly Pro Gly Gly Met
305                 310                 315                 320

Thr Gly Trp Tyr Asn Arg Thr Met Gln Gln Ala Pro Ile Val Leu Thr
                325                 330                 335

Pro Ala Ala Leu Thr Met Phe Pro Asp Thr Ile Lys Phe Gly Asp Leu
            340                 345                 350

Asn Tyr Pro Val Met Ile Gly Asp Pro Met Ile Leu Gly
                355                 360                 365

<210> SEQ ID NO 26
<211> LENGTH: 2203
<212> TYPE: DNA
<213> ORGANISM: Reovirus

<400> SEQUENCE: 26
gctaatctgc tgaccgttac tctgcaaaga tggggaacgc ttcctctatc gttcagacga      60
tcaacgtcac tggagatggc aatgtattta accatcagc tgaaacttca tctaccgctg     120
taccatcgtt aagcttatca cctggaatgc tgaatcccgg aggggtacca tggattgctg     180
ttggagatga cacatctgtg acttcaccag gcgcattacg tcgaatgacg tcaaaggaca     240
tcccggaaac ggcaataatc aacacagaca attcatcagg cgccgtgcca agcgaatcag     300
cgcttgtgcc ctacatcgat gagccgctgg tagtggttac agagcatgct attaccaact     360
tcaccaaagc tgagatggca cttgaattca atcgtgagtt ccttgacaag atgcgtgtgc     420
tgtcagtgtc accaaaatat tcggatcttc tgacctatgt tgactgctac gtcggtgtgt     480
ctgctcgtca ggctttaaac aattttcaga aacaagtgcc tgtgattaca cctactaggc     540
agacgatgta tgtcgactcg atacaagcgg ccttgaaagc tttagaaaag tgggagattg     600
atctgagagt ggctcaaacg ttgctgccta cgaacgttcc gattggagaa gtctcttgtc     660
caatgcagtc ggtagtgaaa ctgctggatg atcagctgcc agatgacacg ctgatacgga     720
ggtatcccaa ggaagccgcc gtcgctttgg ctaaacgaaa cggggaata caatggatgg     780
acgtatcaga aggcaccgtg atgaacgagg ctgtcaacgc tgttgcagct agtgcactgg     840
caccttcagc atcagcccca cccttagaag agaagtcaaa gttaaccgaa caagcgatgg     900
atctcgtgac cgcggctgag cctgagataa ttgcctcact cgcgccagtt cccgcacccg     960
tgtttgccat accacctaaa ccagcagatt ataatgtgcg tactctgagg atcgacgagg    1020
ccacttggct gcgaatgatt ccaaaatcaa tgaacacacc ttttcaaatc caggtgactg    1080
```

-continued

```
ataacacagg aactaattgg catctcaatt tgagggggggg gactcgtgta gtgaatctgg   1140
accaaatcgc tccgatgcgg tttgtattag atttaggggg aaagagttat aaagagacga   1200
gctgggatcc aaacggcaag aaggtcggat tcatcgtttt tcaatcgaag ataccattcg   1260
aactttggac tgctgcttca cagatcggtc aagccacggt ggttaactat gtccaactat   1320
acgctgaaga cagctcattt accgcgcagt ctatcattgc tactacctct ttggcttata   1380
actatgagcc tgagcagttg aataagactg accctgagat gaattattat cttttggcga   1440
cctttataga ctcagccgct ataacgccaa cgaatatgac acagcctgat gtttgggatg   1500
ccttgctgac gatgtcccca ctatcagctg gcgaggtgac agtgaagggt gcggtagtga   1560
gtgaagtagt ccctgcagac ttgataggta gctacactcc agaatcccta acgcctcac    1620 ttccgaatga tgctgctaga tgcatgatcg atagagcttc gaagatagcc gaagcaatca   1680
agattgatga tgatgctgga ccagatgaat attccccaaa ctctgtacca attcaaggtc   1740
agcttgctat ctcgcaactc gaaactggat atggtgtgcg aatattcaac cctaaaggga   1800
tcctttctaa aattgcatct agggcaatgc aggctttcat tggtgacccg agcacaatca   1860
tcacgcaggc ggcgcagtg ttatcagaca agaataattg gattgcattg cacagggag     1920 tgaaaactag tctgcgtact aaaagtctat cagcgggagt gaagactgca gtgagtaagc   1980
tgagctcatc tgagtctatc cagaattgga ctcaaggatt cttggataaa gtgtcagcgc   2040
attttccagc accaaagccc gattgtccga ctagcggaga tagtggtgaa tcgtctaatc   2100
gccgagtgaa gcgcgactca tacgcaggag tggtcaaacg tgggtacaca cgttaggccg   2160
ctcgccctgg tgacgcgggg ttaagggatg caggcaaatc atc                     2203
```

<210> SEQ ID NO 27
<211> LENGTH: 708
<212> TYPE: PRT
<213> ORGANISM: Reovirus

<400> SEQUENCE: 27

```
Met Gly Asn Ala Ser Ser Ile Val Gln Thr Ile Asn Val Thr Gly Asp
 1               5                  10                  15

Gly Asn Val Phe Lys Pro Ser Ala Glu Thr Ser Ser Thr Ala Val Pro
            20                  25                  30

Ser Leu Ser Leu Ser Pro Gly Met Leu Asn Pro Gly Gly Val Pro Trp
        35                  40                  45

Ile Ala Val Gly Asp Glu Thr Ser Val Thr Ser Pro Gly Ala Leu Arg
    50                  55                  60

Arg Met Thr Ser Lys Asp Ile Pro Glu Thr Ala Ile Ile Asn Thr Asp
65                  70                  75                  80

Asn Ser Ser Gly Ala Val Pro Ser Glu Ser Ala Leu Val Pro Tyr Ile
                85                  90                  95

Asp Glu Pro Leu Val Val Thr Glu His Ala Ile Thr Asn Phe Thr
            100                 105                 110

Lys Ala Glu Met Ala Leu Glu Phe Asn Arg Glu Phe Leu Asp Lys Met
        115                 120                 125

Arg Val Leu Ser Val Ser Pro Lys Tyr Ser Asp Leu Leu Thr Tyr Val
    130                 135                 140

Asp Cys Tyr Val Gly Val Ser Ala Arg Gln Ala Leu Asn Asn Phe Gln
145                 150                 155                 160

Lys Gln Val Pro Val Ile Thr Pro Thr Arg Gln Thr Met Tyr Val Asp
                165                 170                 175
```

-continued

```
Ser Ile Gln Ala Ala Leu Lys Ala Leu Glu Lys Trp Glu Ile Asp Leu
            180                 185                 190

Arg Val Ala Gln Thr Leu Leu Pro Thr Asn Val Pro Ile Gly Glu Val
        195                 200                 205

Ser Cys Pro Met Gln Ser Val Val Lys Leu Leu Asp Asp Gln Leu Pro
210                 215                 220

Asp Asp Thr Leu Ile Arg Arg Tyr Pro Lys Glu Ala Ala Val Ala Leu
225                 230                 235                 240

Ala Lys Arg Asn Gly Gly Ile Gln Trp Met Asp Val Ser Glu Gly Thr
                245                 250                 255

Val Met Asn Glu Ala Val Asn Ala Val Ala Ala Ser Ala Leu Ala Pro
            260                 265                 270

Ser Ala Ser Ala Pro Pro Leu Glu Glu Lys Ser Lys Leu Thr Glu Gln
        275                 280                 285

Ala Met Asp Leu Val Thr Ala Ala Glu Pro Glu Ile Ile Ala Ser Leu
290                 295                 300

Ala Pro Val Pro Ala Pro Val Phe Ala Ile Pro Pro Lys Pro Ala Asp
305                 310                 315                 320

Tyr Asn Val Arg Thr Leu Arg Ile Asp Glu Ala Thr Trp Leu Arg Met
                325                 330                 335

Ile Pro Lys Ser Met Asn Thr Pro Phe Gln Ile Gln Val Thr Asp Asn
            340                 345                 350

Thr Gly Thr Asn Trp His Leu Asn Leu Arg Gly Gly Thr Arg Val Val
        355                 360                 365

Asn Leu Asp Gln Ile Ala Pro Met Arg Phe Val Leu Asp Leu Gly Gly
370                 375                 380

Lys Ser Tyr Lys Glu Thr Ser Trp Asp Pro Asn Gly Lys Lys Val Gly
385                 390                 395                 400

Phe Ile Val Phe Gln Ser Lys Ile Pro Phe Glu Leu Trp Thr Ala Ala
                405                 410                 415

Ser Gln Ile Gly Gln Ala Thr Val Val Asn Tyr Val Gln Leu Tyr Ala
            420                 425                 430

Glu Asp Ser Ser Phe Thr Ala Gln Ser Ile Ile Ala Thr Thr Ser Leu
        435                 440                 445

Ala Tyr Asn Tyr Glu Pro Glu Gln Leu Asn Lys Thr Asp Pro Glu Met
450                 455                 460

Asn Tyr Tyr Leu Leu Ala Thr Phe Ile Asp Ser Ala Ala Ile Thr Pro
465                 470                 475                 480

Thr Asn Met Thr Gln Pro Asp Val Trp Asp Ala Leu Leu Thr Met Ser
                485                 490                 495

Pro Leu Ser Ala Gly Glu Val Thr Val Lys Gly Ala Val Val Ser Glu
            500                 505                 510

Val Val Pro Ala Asp Leu Ile Gly Ser Tyr Thr Pro Glu Ser Leu Asn
        515                 520                 525

Ala Ser Leu Pro Asn Asp Ala Ala Arg Cys Met Ile Asp Arg Ala Ser
530                 535                 540

Lys Ile Ala Glu Ala Ile Lys Ile Asp Asp Ala Gly Pro Asp Glu
545                 550                 555                 560

Tyr Ser Pro Asn Ser Val Pro Ile Gln Gly Gln Leu Ala Ile Ser Gln
                565                 570                 575

Leu Glu Thr Gly Tyr Gly Val Arg Ile Phe Asn Pro Lys Gly Ile Leu
            580                 585                 590

Ser Lys Ile Ala Ser Arg Ala Met Gln Ala Phe Ile Gly Asp Pro Ser
```

```
                    595                 600                 605
Thr Ile Ile Thr Gln Ala Ala Pro Val Leu Ser Asp Lys Asn Asn Trp
    610                 615                 620

Ile Ala Leu Ala Gln Gly Val Lys Thr Ser Leu Arg Thr Lys Ser Leu
625                 630                 635                 640

Ser Ala Gly Val Lys Thr Ala Val Ser Lys Leu Ser Ser Ser Glu Ser
                645                 650                 655

Ile Gln Asn Trp Thr Gln Gly Phe Leu Asp Lys Val Ser Ala His Phe
            660                 665                 670

Pro Ala Pro Lys Pro Asp Cys Pro Thr Ser Gly Asp Ser Gly Glu Ser
        675                 680                 685

Ser Asn Arg Arg Val Lys Arg Asp Ser Tyr Ala Gly Val Val Lys Arg
    690                 695                 700

Gly Tyr Thr Arg
705

<210> SEQ ID NO 28
<211> LENGTH: 2304
<212> TYPE: DNA
<213> ORGANISM: Reovirus

<400> SEQUENCE: 28
gctattcgcg gtcatggctt acatcgcagt tcctgcggtg gtggattcac gttcgagtga      60
ggctattgga ctgctagaat cgtttggagt agacgctggg gctgacgcga atgacgtttc     120
atatcaagat catgactatg tgttggatca gttacagtac atgttagatg gatatgaggc     180
tggtgacgtt atcgatgcac tcgtccacaa gaattggtta catcactctg tctattgctt     240
gttgccaccc aaaagtcaac tattagagta ttggaaaagt aatccttcag cgataccgga     300
caacgttgat cgtcggcttc gtaaacgact aatgctaaag aaagatctca ggaaagatga     360
tgaatacaat cagctagcgc gtgctttcaa gatatcggat gtctacgcac ctctcatctc     420
atccacgacg tcaccgatga caatgataca gaacttgaat cgaggcgaga tcgtgtacac     480
cacgacggac agggtaatag gggctagaat cttgttatat gctcctagaa agtactatgc     540
gtcaactctg tcatttacta tgactaagtg catcattccg tttggtaaag aggtgggtcg     600
tgttcctcac tctcgattta atgttggcac atttccgtca attgctaccc cgaaatgttt     660
tgtcatgagt ggggttgata ttgagtccat cccaaatgaa tttatcaagt tgttttacca     720
gcgcgtcaag agtgttcacg ctaacatact aaatgacata tcctcagat cgtctctga     780 catgataaac agaaagcgtc tgcgcgttca tactccatca gatcgtcgag ccgcgcagtt     840
gatgcatttg ccttaccatg ttaaacgagg agcgtctcac gtcgacgttt acaaggtgga     900
tgttgtagac atgttgttcg aggtagtgga tgtggccgat gggttgcgca acgtatctag     960
gaaactaact atgcataccg ttcctgtatg tattcttgaa atgttgggta ttgagattgc    1020
ggactattgc attcgtcaag aggatggaat gctcacagat tggttcctac tttttaaccat   1080 gctatctgat ggcttgactg atagaaggac gcattgtcaa tacttgatga atccgtcaag    1140
tgtgcctcct gatgtgatac ttaacatctc aattactgga tttataaata gacatacaat    1200
cgatgtcatg cctgacatat atgacttcgt taaacccatt ggcgctgtgc tgcctaaggg    1260
atcatttaaa tcaacaatta tgagagttct tgattcaata tcaatattag aatccaaat    1320 catgccgcgc gcgcatgtag ttgactcaga tgaggtgggc gagcaaatgg agcctacgtt    1380
tgagcaggcg gttatggaga tatacaaagg gattgctggc gttgactcgc tggatgatct    1440
```

-continued

```
catcaagtgg gtgttgaact cggatctcat tccgcatgat gacaggcttg gtcaattatt    1500
tcaagcgttt ttgcctctcg caaaggactt attagctcca atggccagaa agttttatga    1560
taactcaatg agtgagggta gattgctaac attcgctcat gccgacagtg agttgctgaa    1620
cgcaaattat tttggtcatt tattgcgact aaaaatacca tatattacag aggttaatct    1680
gatgattcgc aagaatcgtg agggtggaga gctatttcag cttgtgttat cttatctata    1740
taaaatgtat gctactagcg cgcagcctaa atggtttgga tcattattgc gattgttaat    1800
atgtccctgg ttacatatgg agaaattaat aggagaagca gacccggcat ctacgtcggc    1860
tgaaattggg tggcatatcc ctcgtgaaca gctgatgcaa gatggatggt gtggatgtga    1920
agacggattc attccctatg ttagcatacg tgcgccaaga ctggttatag aggagttgat    1980
ggagaagaac tggggccaat atcatgccca agttattgtc actgatcagc ttgtcgtagg    2040
cgaaccgcgg agggtatctg ctaaggctgt gatcaagggt aaccacttac cagttaagtt    2100
agtttcacga tttgcatgtt tcacattgac ggcgaagtat gagatgaggc tttcgtgcgg    2160
ccatagcact ggacgtggag ctgcatacag tgcgagacta gctttccgat ctgacttggc    2220
gtgatccgtg acatgcgtag tgtgacacct gctcctaggt caatgggggt agggggcggg    2280
ctaagactac gtacgcgctt catc                                           2304
```

<210> SEQ ID NO 29
<211> LENGTH: 736
<212> TYPE: PRT
<213> ORGANISM: Reovirus

<400> SEQUENCE: 29

```
Met Ala Tyr Ile Ala Val Pro Ala Val Val Asp Ser Arg Ser Ser Glu
 1               5                  10                  15

Ala Ile Gly Leu Leu Glu Ser Phe Gly Val Asp Ala Gly Ala Asp Ala
             20                  25                  30

Asn Asp Val Ser Tyr Gln Asp His Asp Tyr Val Leu Asp Gln Leu Gln
         35                  40                  45

Tyr Met Leu Asp Gly Tyr Glu Ala Gly Asp Val Ile Asp Ala Leu Val
     50                  55                  60

His Lys Asn Trp Leu His His Ser Val Tyr Cys Leu Leu Pro Pro Lys
 65                  70                  75                  80

Ser Gln Leu Leu Glu Tyr Trp Lys Ser Asn Pro Ser Ala Ile Pro Asp
                 85                  90                  95

Asn Val Asp Arg Arg Leu Arg Lys Arg Leu Met Leu Lys Lys Asp Leu
            100                 105                 110

Arg Lys Asp Asp Glu Tyr Asn Gln Leu Ala Arg Ala Phe Lys Ile Ser
        115                 120                 125

Asp Val Tyr Ala Pro Leu Ile Ser Ser Thr Thr Ser Pro Met Thr Met
    130                 135                 140

Ile Gln Asn Leu Asn Arg Gly Glu Ile Val Tyr Thr Thr Thr Asp Arg
145                 150                 155                 160

Val Ile Gly Ala Arg Ile Leu Leu Tyr Ala Pro Arg Lys Tyr Tyr Ala
                165                 170                 175

Ser Thr Leu Ser Phe Thr Met Thr Lys Cys Ile Ile Pro Phe Gly Lys
            180                 185                 190

Glu Val Gly Arg Val Pro His Ser Arg Phe Asn Val Gly Thr Phe Pro
        195                 200                 205

Ser Ile Ala Thr Pro Lys Cys Phe Val Met Ser Gly Val Asp Ile Glu
    210                 215                 220
```

```
Ser Ile Pro Asn Glu Phe Ile Lys Leu Phe Tyr Gln Arg Val Lys Ser
225                 230                 235                 240

Val His Ala Asn Ile Leu Asn Asp Ile Ser Pro Gln Ile Val Ser Asp
                245                 250                 255

Met Ile Asn Arg Lys Arg Leu Arg Val His Thr Pro Ser Asp Arg Arg
            260                 265                 270

Ala Ala Gln Leu Met His Leu Pro Tyr His Val Lys Arg Gly Ala Ser
        275                 280                 285

His Val Asp Val Tyr Lys Val Asp Val Asp Met Leu Phe Glu Val
    290                 295                 300

Val Asp Val Ala Asp Gly Leu Arg Asn Val Ser Arg Lys Leu Thr Met
305                 310                 315                 320

His Thr Val Pro Val Cys Ile Leu Glu Met Leu Gly Ile Glu Ile Ala
                325                 330                 335

Asp Tyr Cys Ile Arg Gln Glu Asp Gly Met Leu Thr Asp Trp Phe Leu
            340                 345                 350

Leu Leu Thr Met Leu Ser Asp Gly Leu Thr Asp Arg Arg Thr His Cys
        355                 360                 365

Gln Tyr Leu Met Asn Pro Ser Ser Val Pro Pro Asp Val Ile Leu Asn
370                 375                 380

Ile Ser Ile Thr Gly Phe Ile Asn Arg His Thr Ile Asp Val Met Pro
385                 390                 395                 400

Asp Ile Tyr Asp Phe Val Lys Pro Ile Gly Ala Val Leu Pro Lys Gly
                405                 410                 415

Ser Phe Lys Ser Thr Ile Met Arg Val Leu Asp Ser Ile Ser Ile Leu
            420                 425                 430

Gly Ile Gln Ile Met Pro Arg Ala His Val Val Asp Ser Asp Glu Val
        435                 440                 445

Gly Glu Gln Met Glu Pro Thr Phe Glu Gln Ala Val Met Glu Ile Tyr
    450                 455                 460

Lys Gly Ile Ala Gly Val Asp Ser Leu Asp Asp Leu Ile Lys Trp Val
465                 470                 475                 480

Leu Asn Ser Asp Leu Ile Pro His Asp Asp Arg Leu Gly Gln Leu Phe
                485                 490                 495

Gln Ala Phe Leu Pro Leu Ala Lys Asp Leu Leu Ala Pro Met Ala Arg
            500                 505                 510

Lys Phe Tyr Asp Asn Ser Met Ser Glu Gly Arg Leu Leu Thr Phe Ala
        515                 520                 525

His Ala Asp Ser Glu Leu Leu Asn Ala Asn Tyr Phe Gly His Leu Leu
    530                 535                 540

Arg Leu Lys Ile Pro Tyr Ile Thr Glu Val Asn Leu Met Ile Arg Lys
545                 550                 555                 560

Asn Arg Glu Gly Gly Glu Leu Phe Gln Leu Val Leu Ser Tyr Leu Tyr
                565                 570                 575

Lys Met Tyr Ala Thr Ser Ala Gln Pro Lys Trp Phe Gly Ser Leu Leu
            580                 585                 590

Arg Leu Leu Ile Cys Pro Trp Leu His Met Glu Lys Leu Ile Gly Glu
        595                 600                 605

Ala Asp Pro Ala Ser Thr Ser Ala Glu Ile Gly Trp His Ile Pro Arg
    610                 615                 620

Glu Gln Leu Met Gln Asp Gly Trp Cys Gly Cys Glu Asp Gly Phe Ile
625                 630                 635                 640
```

```
Pro Tyr Val Ser Ile Arg Ala Pro Arg Leu Val Ile Glu Glu Leu Met
                645                 650                 655

Glu Lys Asn Trp Gly Gln Tyr His Ala Gln Val Ile Val Thr Asp Gln
            660                 665                 670

Leu Val Val Gly Glu Pro Arg Arg Val Ser Ala Lys Ala Val Ile Lys
        675                 680                 685

Gly Asn His Leu Pro Val Lys Leu Val Ser Arg Phe Ala Cys Phe Thr
    690                 695                 700

Leu Thr Ala Lys Tyr Glu Met Arg Leu Ser Cys Gly His Ser Thr Gly
705                 710                 715                 720

Arg Gly Ala Ala Tyr Ser Ala Arg Leu Ala Phe Arg Ser Asp Leu Ala
                725                 730                 735

<210> SEQ ID NO 30
<211> LENGTH: 418
<212> TYPE: PRT
<213> ORGANISM: Reovirus

<400> SEQUENCE: 30

Met Ala Arg Ala Ala Phe Leu Phe Lys Thr Val Gly Phe Gly Gly Leu
  1               5                  10                  15

Gln Asn Val Pro Ile Asn Asp Glu Leu Ser Ser His Leu Leu Arg Ala
             20                  25                  30

Gly Asn Ser Pro Trp Gln Leu Thr Gln Phe Leu Asp Trp Ile Ser Leu
         35                  40                  45

Gly Arg Gly Leu Ala Thr Ser Ala Leu Val Pro Thr Ala Gly Ser Arg
     50                  55                  60

Tyr Tyr Gln Met Ser Cys Leu Leu Ser Gly Thr Leu Gln Ile Pro Phe
 65                  70                  75                  80

Arg Pro Asn His Arg Trp Gly Asp Ile Arg Phe Leu Arg Leu Val Trp
                 85                  90                  95

Ser Ala Pro Thr Leu Asp Gly Leu Val Val Ala Pro Pro Gln Val Leu
            100                 105                 110

Ala Gln Pro Ala Leu Gln Ala Gln Ala Asp Arg Val Tyr Asp Cys Asp
        115                 120                 125

Asp Tyr Pro Phe Leu Ala Arg Asp Pro Arg Phe Lys His Arg Val Tyr
    130                 135                 140

Gln Gln Leu Ser Ala Val Thr Leu Leu Asn Leu Thr Gly Phe Gly Pro
145                 150                 155                 160

Ile Ser Tyr Val Arg Val Asp Glu Asp Met Trp Ser Gly Asp Val Asn
                165                 170                 175

Gln Leu Leu Met Asn Tyr Phe Gly His Thr Phe Ala Glu Ile Ala Tyr
            180                 185                 190

Thr Leu Cys Gln Ala Ser Ala Asn Arg Pro Trp Glu Tyr Asp Gly Thr
        195                 200                 205

Tyr Ala Arg Met Thr Gln Ile Val Leu Ser Leu Phe Trp Leu Ser Tyr
    210                 215                 220

Val Gly Val Ile His Gln Gln Asn Thr Tyr Arg Thr Phe Tyr Phe Gln
225                 230                 235                 240

Cys Asn Arg Arg Gly Asp Ala Ala Glu Val Trp Ile Leu Ser Cys Ser
                245                 250                 255

Leu Asn His Ser Ala Gln Ile Arg Pro Gly Asn Arg Ser Leu Phe Val
            260                 265                 270

Met Pro Thr Ser Pro Asp Trp Asn Met Asp Val Asn Leu Ile Leu Ser
        275                 280                 285
```

-continued

```
Ser Thr Leu Thr Gly Cys Leu Cys Ser Gly Ser Gln Leu Pro Leu Ile
    290                 295                 300

Asp Asn Asn Ser Val Pro Ala Val Ser Arg Asn Ile His Gly Trp Thr
305                 310                 315                 320

Gly Arg Ala Gly Asn Gln Leu His Gly Phe Gln Val Arg Arg Met Val
                325                 330                 335

Thr Glu Phe Cys Asp Arg Leu Arg Arg Asp Gly Val Met Thr Gln Ala
            340                 345                 350

Gln Gln Asn Gln Val Glu Ala Leu Ala Asp Gln Thr Gln Gln Phe Lys
        355                 360                 365

Arg Asp Lys Leu Glu Thr Trp Ala Arg Glu Asp Asp Gln Tyr Asn Gln
    370                 375                 380

Ala His Pro Asn Ser Thr Met Phe Arg Thr Lys Pro Phe Thr Asn Ala
385                 390                 395                 400

Gln Trp Gly Arg Gly Asn Thr Gly Ala Thr Ser Ala Ala Ile Ala Ala
                405                 410                 415

Leu Ile
```